United States Patent
Lauffer et al.

(10) Patent No.: US 6,652,835 B1
(45) Date of Patent: Nov. 25, 2003

(54) TARGETING MULTIMERIC IMAGING AGENTS THROUGH MULTILOCUS BINDING

(75) Inventors: Randall B. Lauffer, Brookline, MA (US); Thomas J. McMurry, Winchester, MA (US); Stephane Dumas, Cambridge, MA (US); Andrew Kolodziej, Winchester, MA (US); John Amedio, Franklin, MA (US); Peter Caravan, Cambridge, MA (US); Zhaoda Zhang, Andover, MA (US)

(73) Assignee: Epix Medical, Inc., Cambridge, MA (US)

( * ) Notice: Subject to any disclaimer, the term of this patent is extended or adjusted under 35 U.S.C. 154(b) by 0 days.

(21) Appl. No.: 09/627,719

(22) Filed: Jul. 28, 2000

Related U.S. Application Data

(60) Provisional application No. 60/163,650, filed on Nov. 4, 1999, and provisional application No. 60/146,414, filed on Jul. 29, 1999.

(51) Int. Cl.[7] .................................................. A61B 5/055
(52) U.S. Cl. ................ 424/9.36; 424/9.361; 424/9.363; 424/9.364
(58) Field of Search .......................... 424/9.36, 9.361, 424/9.363, 9.364, 9.365

(56) References Cited

U.S. PATENT DOCUMENTS

| | | | |
|---|---|---|---|
| 4,880,008 A | 11/1989 | Lauffer et al. ............... | 128/654 |
| 5,401,493 A | 3/1995 | Lohrmann et al. ............. | 424/9 |
| 5,573,752 A | 11/1996 | Ranganathan et al. ... | 424/9.363 |
| 5,637,759 A | 6/1997 | Hearst et al. ................ | 560/159 |
| 5,650,133 A | 7/1997 | Carvalho et al. .......... | 424/1.65 |
| 5,914,095 A | 6/1999 | Watson ...................... | 424/1.65 |
| 5,977,064 A | 11/1999 | Dean et al. .................... | 514/9 |

FOREIGN PATENT DOCUMENTS

| | | | | |
|---|---|---|---|---|
| DE | 196 41 197 A1 | 5/1998 | ......... | C07C/237/46 |
| NZ | 28 44 13 | 8/1998 | | |
| NZ | 29 68 23 | 10/1999 | | |
| WO | WO 88/01178 | 2/1988 | .......... | A61K/49/02 |
| WO | WO 88/01179 | 2/1988 | .......... | A61K/49/02 |
| WO | WO 88/01180 | 2/1988 | .......... | A61K/49/02 |
| WO | WO 91/05762 | 5/1991 | ......... | C07C/237/10 |
| WO | WO 93/06868 | 4/1993 | .......... | A61K/49/00 |
| WO | WO 95/07270 | 3/1995 | ......... | C07D/357/02 |
| WO | WO 95/09848 | 4/1995 | ......... | C07D/257/02 |
| WO | WO 95/17451 | 6/1995 | ........... | C08G/85/00 |
| WO | WO 95/25763 | 9/1995 | ........... | C08G/65/32 |
| WO | WO 95/28966 | 11/1995 | .......... | A61K/49/00 |
| WO | WO 96/01655 | 1/1996 | .......... | A61K/49/00 |
| WO | WO 96/22321 | 7/1996 | ........... | C08G/69/00 |
| WO | WO 96/23526 | 8/1996 | .......... | A61K/49/00 |
| WO | WO 96/35456 | 11/1996 | .......... | A61K/49/00 |
| WO | WO 96/41830 | 12/1996 | ........... | C08G/73/02 |
| WO | WO 97/02051 | 1/1997 | .......... | A61K/49/00 |
| WO | WO 97/06833 | 2/1997 | .......... | A61K/51/02 |
| WO | WO 97/10281 | 3/1997 | .......... | C08G/65/34 |
| WO | WO 97/32862 | 9/1997 | ......... | C07D/257/02 |
| WO | WO 97/36619 | 10/1997 | | |
| WO | WO 97/41856 | 11/1997 | .......... | A61K/31/44 |
| WO | WO 98/41241 | 12/1998 | | |
| WO | WO 99/02193 | 1/1999 | .......... | A61K/49/00 |
| WO | WO 99/25389 | 5/1999 | .......... | A61K/49/00 |
| WO | WO 99/64595 | 12/1999 | ........... | C12N/15/12 |
| WO | WO 00/34231 | 6/2000 | ......... | C07C/217/16 |
| WO | WO 00/34296 | 6/2000 | ......... | C07H/15/08 |
| WO | WO 01/08712 A2 | 2/2001 | .......... | A61K/49/00 |
| WO | WO 01/09188 A1 | 2/2001 | .......... | C07K/16/00 |

OTHER PUBLICATIONS

Aime et al., 1992, "Synthesis, Characterization and 1/$T_1$ NMRD Profiles of Gadolinium (III) Complexes of Monoamide Derivatives of DOTA–like Ligands. X–ray Structure of the 10-[-2-[2-Hydroxy-1-(hydroxymethyl)ethyl]-1-[(phenylmethoxy)methyl]-2-oxo-ethyl]-1,4,7,10-tetraazacyclododecane-1,4,7,10-triacetic Acid-Gadolinium(III) Complex", *Inorg. Chem.*, 31:2422–2428.

Aime et al., 2000, "Multinuclear and multifrequency NMR study of gadolinium(III) complexes with bis–amide derivatives of ethylenedioxydiethylene–dinitrilotetraacetic acid", *J. Chem. Soc., Dalton Trans.* 2000(19):3435–3440.

Amedio et al., 1999, "A Practical Manufacturing Synthesis of 1–(R)–Hydroxymethyl–DPTA: An Important Intermediate in the Synthesis of MRI Contrast Agents", *Synthetic Communications*, 29(14):2377–2391.

Amedio et al., 2000, "Preparation of N,N–BIS2–[N',N'–BIS[(Tert–Butoxycarbonyl)Methyl]–Amino]Ethyl–L–Aspartic Acid: An Intermediate in the Synthesis of MRI Contrast Agents", *Synthetic Communications*, 30(20):3755–3763.

Augustijns et al., 1995, "Peptidyl Dipeptidase A–Catalyzed Metabolism of Delta Sleep–Inducing Peptide in Bovine Brain Microvessel Endothelial Cells: A Cell Culture Model of the Blood Brain Barrier", *Biochem. and Biophysical Research Comm.*, 210:987–994.

(List continued on next page.)

*Primary Examiner*—Michael G. Hartley
(74) *Attorney, Agent, or Firm*—Fish & Richardson P.C.

(57) ABSTRACT

The present invention relates to contrast agents for diagnostic imaging. In particular, this invention relates to novel multimeric compounds which exhibit improved relaxivity properties upon binding to endogenous proteins or other physiologically relevant sites. The compounds consist of:

a) two or more Image Enhancing Moieties (IEMs) (or signal-generating moiety) comprising multiple subunits;

b) two or more Target Binding Moieties (TBMs), providing for in vivo localization and multimer rigidification; and c) a scaffold framework for attachment of the above moieties.

d) optional linkers for attachment of the IEMs to scaffold.

This invention also relates to pharmaceutical compositions comprising these compounds and to methods of using the compounds and compositions for contrast enhancement of diagnostic imaging.

15 Claims, 15 Drawing Sheets

OTHER PUBLICATIONS

Bard et al., 1993, "BisMSH–DTPA: A Potential Imaging Agent for Malignant Melanoma", *Ann NY Acad Sci,* 680:451–453.

Bligh et al., 1994, "Neutral Gadolinium(III) Complexes of Bulky Octadentate dtpa Derivatives as Potential Contrast Agents for Magnetic Resonance Imaging", *Polyhedron* 14:567–569.

Brasch, Robert C., 1991, "Rationale and Applications for Macromolecular Gd–Based Contrast Agents", *Magnetic Resonance in Medicine,* 22:282–287.

Caravan et al., 1999, "Gadolinium(III) Chelates as MRI Contrast Agents: Structure, Dynamics and Applications", *Chem. Rev.* 99:2293–2352.

Deacon et al., 1995, "Degradation of Glucagon–Like Peptide–1 by Human Plasma in Vitro Yields an N–Terminally Truncated Peptide that is a Major Endogenous Metabolite in Vivo", *Journal of Clinical Endocrinology and Metabolism,* 80:952–957.

Kolc, J., 1969, Amino Acids and Peptides. LXXXIX. Synthesis of L–4–Azalysine, D–4–Azalysine, and L–4–Azalysine–[6–$^{14}$C], *Collection Czechoslov. Chem. Commun.,* 34:630–634.

Konings et al., 1990, "Gadolinium Complexation by a New DPTA–Amide Ligand. Amide Oxygen Coordination", *Inorg. Chem.* 29:1488–1491.

Krieter et al., 1989, "In Vivo Metabolism of Atrial Natriuretic Peptide: Identification of Plasma Metabolites and Enzymes Responsible for Their Generation", *The Journal of Pharmacology and Experimental Therapeutics,* 249:411–417.

Lauffer, R. B., 1987, "Paramagnetic Metal Complexes as Water Proton Relaxation Agents for NMR Imaging: Theory and Design", *Chem. Rev.* 87:901–927.

Liu et al., 1999, "Tc–Labeled Small Peptides as Diagnostic Radiopharmaceuticals", *Chem. Rev.* 99:2235–2268.

Moats et al., 1997, "A 'Smart ' Magnetic Resonance Imaging Agent That Reports on Specific Enzymatic Activity", *Angew. Chem. Int. Ed. Engl.* 36:726–728.

Muller et al., 1995, "Metabolism of Dynorphin A 1–13 in Human Blood and Plasma", *Pharmaceutical Research,* 12:1165–1170.

Muller et al., 1999, "Assessment of Complex Peptide Degradation Pathways via Structured Multicompartmental Modeling Approaches: The Metabolism of Dynorphin A1–13 and Related Fragments in Human Plasma", *Journal of Pharmaceutical Sciences,* 88:938–944.

Muller et al., 1999, "Physicochemical Characterization of MS–325, a New Gadolinium Complex, by Multinuclear Reaxaxometry", *Eur. J. Inorg. Chem.,* 1999:1949–1955.

Muller et al., 1996, "Interspecies comparison of in vitro plasma degradation of dynorphin A 1–13", *Pharmazie* 51:581–585.

Murphey et al., 2000, "Metabolism of Bradykinin In Vivo in Humans: Identification of BK1–5 as a Stable Plasma Peptide Metabolite", *Journal of Pharmacology and Experimental Therapeutics,* 29(1)4:263–269.

Peltier et al., 1993, "Radioimmunodetection of Medullary Thyroid Cancer Using a Bispecific Anti–CEA/Anti–Indium–DTPA Antibody and an Indium–111–Labeled DTPA Dimer", *J. Nuc. Med.,* 34:1267–1273.

Powell et al., 1996, "Structural and Dynamic Parameters Obtained from $^{17}$O NMR, EPR, and NMRD Studies of Monomeric and Dimeric Gd$^{3+}$ Complexes of Interest in Magnetic Resonance Imaging: An Integrated and Theoretically Self–Consistent Approach", *J. Am. Chem. Soc.,* 118:9333–9346.

Powell et al., 1993, "Peptide Stability in Drug Development. II. Effect of Single Amino Acid Substitution and Glycosylation on Peptide Reactivity in Human Serum", *Pharmaceutical Research,* 10(9):1268–1273.

Powell, M.F., 1993, "Peptide Stability in Drug Development: In Vitro Peptide Degradation in Plasma and Serum", *Annual Reports in Medicinal Chemistry,* 28:285–294.

Ranganathan et al., 1998, "New Multimeric Magnetic Resonance Imaging Agents", *Investigative Radiology,* 33(11):779–797.

Swanson et al., 1993, "Laminin Peptide Fragments for Malignant Tumor Detection", *J. Nucl. Med.* 34(5 suppl.)231P.

Toth et al., 1997, "Tuning water–exchange rates on (carboxymethyl)iminobis–ethyleneitrilo)tetraacetate (dtpa)–type gadolinium (III) complexes", *J. Chem. Soc., Dalton Trans.* 1997(9):1587–1594.

Villringer et al., 1988, "Dynamic Imaging with Lanthanide Chelates in Normal Brain: Contrast Due to Magnetic Susceptibility Effects", *Magnetic Resonance in Medicine,* 6:164–174.

Wettergren et al., 1998, "Amidated and non–amidated glucagon–like peptide–1 (GLP–1): non–pancreatic effects (cephalic phase acid secretion) and stability in plasma in humans", *Regulatory Peptides,* 77:83–87.

Zhao et al., 1999, "Oxidation of Primary Alcohols to Carboxylic Acids with Sodium Chlorite Catalyzed by TEMPO and Bleach", *J. Org. Chem.* 64:2564–2566.

Clackson et al., 1998, "Redesigning an FKBP–ligand interface to generate chemical dimerizers with novel specificity", *Proc. Natl. Acad. Sci. USA,* 95:10437–10442.

Huber et al., 1998, "Fluorescently Detectable Magnetic Resonance Imaging Agents", *Bioconjugate Chem.,* 9:242–249.

Kramer, R. H. and Karpen, J. W., 1998, "Spanning binding sites on allosteric proteins with polymer–linked ligand dimers", *Nature,* 395:710–713.

Lee et al., 1992, "Multivalent Ligand Binding by Serum Mannose–Binding Protein", *Arch. Biochem. Biophys.,* 299:129–136.

Mann et al., 1998, "Probing Low Affinity and Multivalent Interactions with Surface Plasmon Resonance: Ligands for Concanavalin A", *J. Am. Chem. Soc.,* 120:10575–10582.

Rao et al., 1998, "A Trivalent System from Vancomycin•D–Ala–D–Ala with Higher Affinity Than Avidin•Biotin", *Science,* 280:708–711.

Shukla et al., 1997, "Alteration Of Electronic Relaxation In MR Contrast Agetns Through De–Novo Ligand Design", *Acta Radiologica,* 38 Suppl. 412:121–123.

Shukla et al., 1996, "Design of Conformationally Rigid Dimeric MRI Agents", *Mag. Reson. Med.,* 35:928–931.

Spevak et al., 1996, "Carbohydrates in an Acidic Multivalent Assembly: Nanomolar P–Selectin Inhibitors", *J. Med. Chem.,* 39:1018–1020.

Figure 6

| Examples of Scaffolds | Corresponding multimeric contrast agents |
|---|---|
| (hexamine scaffold) | (hexamine with TBM/IEM substituents) |
| (tetramine scaffold) | (tetramine with TBM/IEM substituents) |
| | (variant with linkers L) |
| | (variant with TBM in middle) |
| (diamine scaffold) | (diamine with TBM/IEM/L substituents) |
| (triamide scaffold with X groups) | (triamide with X-TBM and IEM substituents) |

X = N, O, S      L = Linker

Figure 7
| Examples of scaffolds | Corresponding multimeric contrast agents |
|---|---|
| 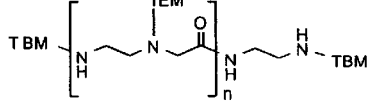 | 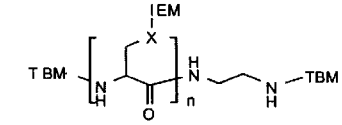 |
| 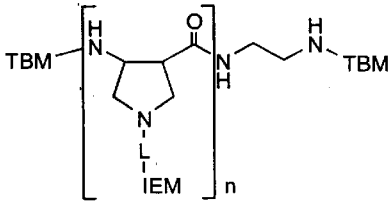 | 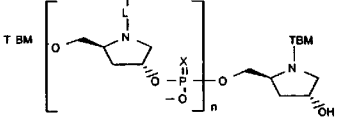 |
| | 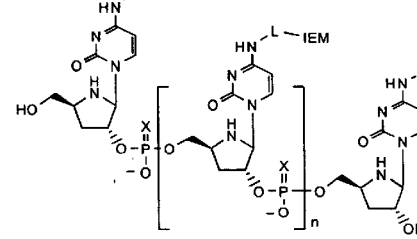 |
X = N, O, S        L = Linker Figure 10, Part A
| Examples of Scaffolds - Polyamines | Corresponding multimeric contrast agents |
|---|---|
| 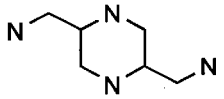 | 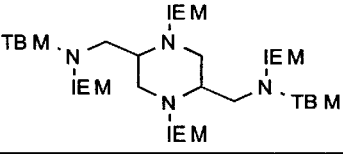 |
| 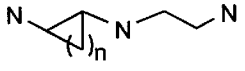 | 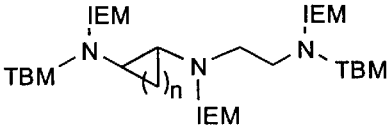 |
| 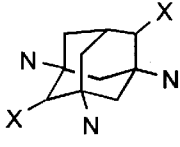 | 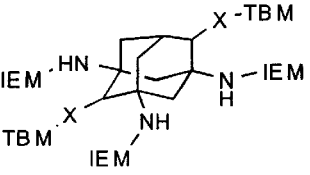 |
|  | 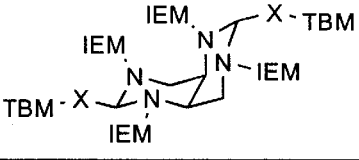 |
| 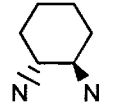 | 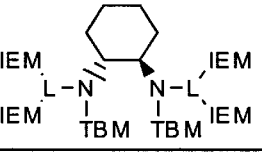 |
| 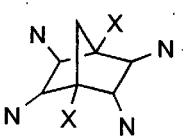 | 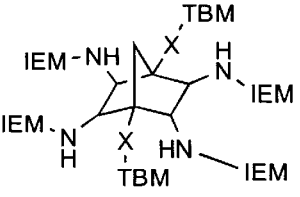 |
| 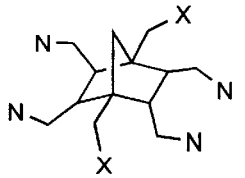 | 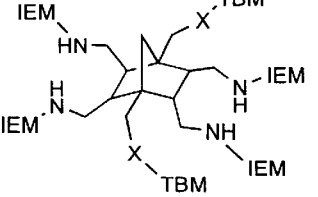 |

Figure 10, Part B

| Polyaminoalcohol or ether derivatives | Corresponding multimeric contrast agents |
|---|---|
| [structure: morpholine-like ring with N, O] | [structure with IEM, TBM substituents] |
| [structure: piperazine with CH2O groups] | [structure with IEM, TBM substituents] |
| [structure: cyclopentane with N, N, O, O] | [structure with IEM, TBM substituents] |
| Carbohydrate derivatives | Corresponding multimeric contrast agents |
| [disaccharide structure] | [disaccharide structure with IEM, TBM substituents] |

$X = N, O, S, CH_2$
$n = 1-8$

X = N, O, S

M8-11

TARGETING MULTIMERIC IMAGING AGENTS THROUGH MULTILOCUS BINDING

RELATED U.S. APPLICATION DATA

This application claims the benefit of U.S. Provisional Application No.: 60/146,414, filed Jul. 29, 1999, and No. 60/163,650, filed Nov. 4, 1999.

TECHNICAL FIELD OF THE INVENTION

The present invention relates to contrast agents for diagnostic imaging. In particular, this invention relates to novel multimeric compounds which exhibit improved affinity for physiologically relevant targets, such as proteins, and surprisingly improved relaxivity properties upon binding. The compounds comprise:

a) two or more Image Enhancing Moieties ("IEMs")

b) two or more Target Binding Moieties ("TBMs"), providing for in vivo localization and multimer rigidification;

c) a scaffold framework for attachment of the above moieties ("scaffold");

d) optional linkers for attachment of IEMs to the scaffold ("linker").

This invention also relates to pharmaceutical compositions comprising these compounds and to methods of using the compounds and compositions for contrast enhancement during imaging.

BACKGROUND OF THE INVENTION

Diagnostic imaging techniques, such as magnetic resonance imaging (MRI), X-ray, nuclear radiopharmaceutical imaging, ultraviolet-visible-infrared light imaging, and ultrasound, have been used in medical diagnosis for a number of years. Contrast media additionally have been used to improve or increase the resolution of the image or to provide specific diagnostic information. In some cases, such as imaging with ultrasound, the introduction of contrast media has been recent.

To be effective, the contrast media must interfere with the wavelength of electromagnetic radiation used in the imaging technique, alter the physical properties of tissue to yield an altered signal, or, as in the case of radiopharmaceuticals, provide the source of radiation itself. MRI and optical imaging methods are unique among imaging modalities in that they yield complex signals that are sensitive to the chemical environment. While the signal from X-ray or radionuclide agents remains the same whether the agents are free in plasma, bound to proteins or other targets, or trapped inside bone, certain contrast agents for MRI and optical imaging will have different signal characteristics in differing physiological environments. An optical dye may exhibit changes in its absorbance, reflectance, fluorescence, phosphorescence, chemiluminescence, scattering, or other spectral properties upon binding. It is important that the contrast agent be sufficiently sensitive and present at high enough concentration so that signal changes can be observed.

Attempts to Improve Contrast by Increasing the Number of IEMs

Targeted agents should deliver meaningful concentrations of the imaging moiety to the target so that sufficient improvement in the signal is observed during the course of imaging. Achieving sufficient sensitivity is a significant problem for MRI in particular, where concentrations in the range of 10–1000 micromolar ($\mu$M) of the image enhancing moiety are required to produce an adequate signal. The problem can be further complicated for targeted agents if the desired target is present at low concentrations. For example, in order to image biological receptor targets that are present at less than $\mu$M concentrations, greater signal enhancement is required at the target site to provide sufficient image contrast. Increased contrast has been approached by using (1) drug delivery vehicles to provide high local concentrations of the contrast agent, (2) multiple IEMs in a single contrast agent, [see, for example, Martin V. V., et al., *Bioconjug. Chem.*, 6: pp. 616–23 (1995); Shukla, R. et al., *Mag. Reson. Med.*, 35: pp. 928–931 (1996); Ranganathan, R. S., et al., *Invest. Radiol.*, 33: pp. 779–797 (1998)], or (3) particular IEMs of defined structure with improved signal enhancement properties. The ideal targeted contrast agent should efficiently combine IEMs and improved signal enhancement properties.

To incorporate a high number of image enhancing moieties into a contrast agent, large concentrations of low molecular weight contrast agents have been packaged within suitable drug delivery vehicles, such as polymerized vehicles or liposomes [Bulte J. W., et al., *J. Magn. Reson. Imaging*, 9: pp. 329–335 (1999)]. Unfortunately, these materials are difficult to direct to a target.

To increase the number of the image enhancing moieties, investigators have, for example, created polymers, dendrimers, and organic compounds in association with multiple IEMs. High numbers of IEMs, such as Gd(III) chelates for MRI, can be covalently attached to polymers [Schuhmann-Giampieri, G. et al. *J. Invest. Rad.*, 26: pp. 969–974 (1991); Corot, C. et al. *Acta Rad.*, 38:S412 pp. 91–99 (1997)] and dendrimers [Jacques, V., et al., *J. Alloys Cmpd.*, 249: pp. 173–177 (1997); Margerum, L. D., et al.,*J. Alloys Compd.*, 249: pp. 185–190 (1997); Toth, E., et al., *Chem. Eur. J.*, 2: pp. 1607–1615 (1996)]. Polymeric agents typically comprise a mixture of species with a broad and complex molecular weight distribution. These heterogeneous properties adversely affect agent performance and make characterization difficult. Furthermore, it is synthetically difficult to selectively introduce TBMs along with multiple IEMs. Therefore there exists a need for well-defined, homogeneous molecules for use as contrast agents that can provide adequate image enhancement at a target.

Dendrimers (such as "Starburst dendrimers", or "cascade polymers") theoretically offer a single high molecular weight species onto which many IEMs can be covalently attached. [Fischer, M. et al. *Angew. Chem., Int. Ed. Eng.*, 38/7: pp. 884–905 (1999); Weiner, E. C. et al., *Mag. Reson. Med.*, 31: pp. 1–8 (1994)]. However, dendrimers, like polymeric agents, present significant synthetic problems, especially when selectively introducing tissue-specific targeting groups.

Organic molecules have been synthesized with multiple image enhancing moieties. MRI contrast agents of this type are referred to herein as "multimeric chelates" or "multimers" and typically comprise 2–12 IEMs. [Shukla, R. et al., *Mag. Reson. Med.*, 35: pp. 928–931 (1996); Shukla, R. B., et al.,*Acta Radiol.*, 412: pp. 121–123 (1997); Ranganathan, R. S., et al., *Invest. Radiol.*, 33: pp. 779–797 (1998)]. Advantages of multimeric chelates include: (1) they are homogeneous molecules in that they have a single size and structure, unlike polymers and dendrimers, (2) they can be readily synthesized and purified, and (3) targeting groups can be readily incorporated. Unfortunately, the ability of multimeric chelates to improve the MRI signal intensity has been disappointingly low. This is because the proton relaxation rate enhancement (or "relaxivity"), which correlates with signal enhancement, has decreased as the number of IEMs was increased. Therefore, contrast agents wherein the relaxivity does not decrease when the number of IEMs increases are needed to achieve greater signal enhancement at a target.

Attempts to Improve Contrast by Decreasing the Rotational of the Contrast Agent

Attempts have been made to increase the relaxivity of non-targeted multimeric MRI contrast agents by restricting rotational motion. Attempts to restrict rotational motion have focused on (1) decreasing the flexibility of the molecule or (2) restricting rotational motion through binding to a target.

For example, non-targeted agents have been synthesized with rigid frameworks to which multiple Gd(III) chelates are attached [Shukla, R. et al., *Mag. Reson. Med.*, 35: pp. 928–931 (1996); Shukla, R. B., et al., *Acta Radiol.*, 412: pp. 121–123 (1997); Ranganathan, R. S., et al., *Invest. Radiol.*, 33: pp. 779–797 (1998); Jacques, V., et al., *J. Alloys Cmpd.*, 249: pp. 173–177 (1997)]. However, these structures have several drawbacks. First, the relaxivities per Gd(III) ion that have been achieved for agents containing more than two chelates has been less than that observed for single chelates, such as MS-325. Therefore, local chelate motion could still be further reduced. Second, these agent are not targeted. More importantly, even if they were targeted, rigid multimer frameworks would greatly increase the unwanted background signal because the signal enhancement is significant regardless of whether the contrast agent is bound to a target or not. Therefore, there exists a need for contrast agents that enhance an image of a target only when bound to the target.

Rotational motion of a single IEM can be effectively limited upon non-covalent target binding, resulting in a relaxivity increase for the target-bound forms of as much as 5–10 fold [U.S. Pat. No. 4,880,008]. This relaxivity increase is as good as or better than that observed for IEMs that are covalently linked to the target [Schmiedl, U., Ogan, M., Paajanen, H., Marotti, M., Crooks, L. E., Brito, A. C., and Brasch, R. C. *Radiology* (1987) 162: pp.205–210; Ogan, M. D., Schmiedl, U., Moseley, M. E., Grodd, W., Paajanen, H., and Brasch, R. C. *Invest. Radiol.* (1987) 22: pp. 665–71]. Examples of agents which exploit this effect are the liver protein-targeted contrast agents Gd-EOB DTPA [Runge V. M. *Crit. Rev. Diagn. Imaging* 38: pp. 207–30 (1997)] and Gd-BOPTA [Kirchin M. A., et al., *Invest. Radiol.*, 33: pp. 798–809 (1998)] or the albumin-targeted agents MS-325 [Lauffer, R. B., et al., *Radiology*, 207: pp. 529–538 (1998)] and MP-2269 [Hofman Mark B. M. et al. *Acadademic Radiology*, 5(suppl 1): S206–S209 (1998)]. Relaxivity increases of approximately 7-fold were reported for MS-325 (47 mM$^{-1}$s$^{-1}$) as a result of non-covalent binding to serum albumin [Lauffer, R. B., et al., *Radiology*, 207: pp. 529–538 (1998)].

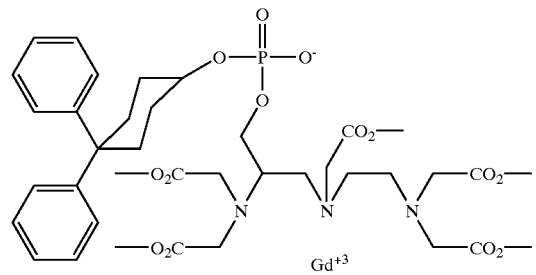
(I)

Upon binding to albumin, the monomeric contrast agent MS-325, having the chemical structure shown by Formula (I), exhibits an increase in signal enhancement. When bound, the complex tumbles at a slower rate than in the unbound state which results in greater relaxivity.

Surprisingly, however, the addition of multiple IEMs to targeted contrast agents, such as MS-325, has failed to enhance contrast further because relaxivity decreases at the individual gadolinium centers in the multimeric structure. For example, an albumin-targeted multimer with four Gd(III) ions exhibited molecular relaxivities per Gd(III) of only 9–13 mm$^{-1}$s$^{-1}$ compared to a relaxivity of 47 mM$^{-1}$s$^{-1}$ for MS-325, which contains a single Gd(III) [Martin V. V., et al., *Bioconjug. Chem.*, 6: pp. 616–23 (1995)]. Thus, the relaxivity of a targeted multimeric chelate is typically much less per Gd (III) than that observed for the analogous targeted single chelate.

Rationale

Table 1 demonstrates that merely increasing the number of IEMs is insufficient to improve total relaxivity because the relaxivity per IEM decreases as the number of IEMs increases despite the presence of the target binding group comprising two phenyl rings. To understand Table 1, it is important to define the extent to which a target-binding MRI contrast agent can achieve its maximum possible relaxivity. This maximum relaxivity for a particular contrast agent is approximately equal to the relaxivity of the molecule when bound to a target (R1$_{bound}$), such as Human Serum Albumin (HSA). The average $\mathbb{R1}_{bound}$ is a normalized measure of the average relaxivity for all bound species under a standard set of conditions (such as a specific target or protein concentration, drug concentration, temperature, etc.) that is weighted by the bound population of each species. Therefore, since the value of $\mathbb{R1}_{bound}$ is a normalized quantity, comparisons of relaxivities can be made among different molecules in the bound state by comparing values for $\mathbb{R1}_{bound}$. Comparison of the calculated $\mathbb{R1}_{bound}$ values provides a convenient method for comparing compounds irrespective of their affinities for a target.

Calculating the average ($\mathbb{R1}_{bound}$) requires measuring the relaxivity of the free chelate (R1$_{free}$) as well as the observed relaxivity (R1$_{obs}$) and percent binding of the agent to a target solution typically containing 4.5% of the target, e.g., HSA. The R1$_{obs}$ is a mole fraction (x) weighted average of R1$_{free}$ and R1$_{bound}$:

$$R1_{obs} = x_{free} R1_{free} + \sum_1 x_i R1_{bound,i}$$

where $x_{free} + \sum_1 x_i = 1$ and $$\sum_1 x_i = x_{bound}$$

Thus:

$$\mathbb{R1}_{bound} = \frac{R1_{ts} - x_{free} R1_{free}}{x_{bound}}$$

The chemical structures and bound relaxivities of a series of albumin-targeted contrast agents are shown in Table 1. In this set of compounds, a compound with a single IEM (i.e., MS-325) is compared with a series of multimers comprising multiple IEMs, but the same diphenylcyclohexyl albumin TBM and the methylene phosphate group are present in all compounds.

TABLE 1

Chemical structures and bound relaxivities of a series of albumin-targeted contrast agents. The diphenylcyclohexyl target binding moiety (TBM) remains constant.

| Compound # | Chemical Structure | Ave. R1$_{bound}$ per Gd(III) (20 MHz) | Total R1bound (20 MHz) |
|---|---|---|---|
| MS-325 | 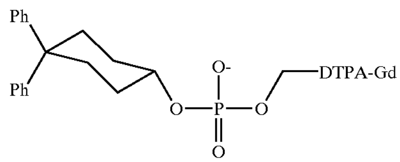 | 47 | 47 |
| M8-01 | 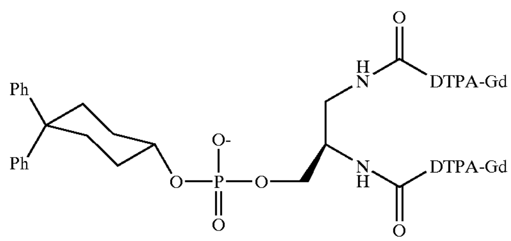 | 38.1 | 76.2 |
| M8-02 | 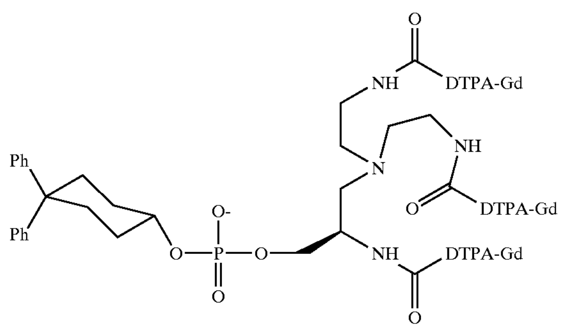 | 23.6 | 70.7 |
| M8-03 | 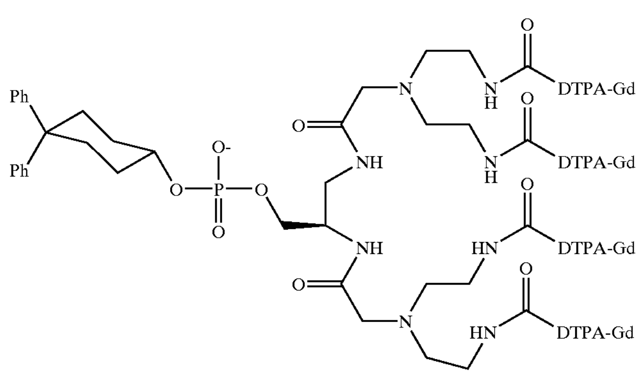 | 14.9 | 59.6 |

FIG. 1 is a graphical representation of the same data shown in Table 1. The average $RI_{bound}$ per IEM, in this case a Gd(III) chelate, at 20 MHz is plotted against the number of IEMs for a series of multimeric contrast agents containing the a single diphenylcyclohexyl protein binding group.

In the molecules of Table 1 and FIG. 1, both the structure of the gadolinium chelate (IEM), the methylene phosphate group, and the diphenylcyclohexyl group (TBM) remain constant. The data in Table 1 and FIG. 1 show that as the number of chelated paramagnetic metal ions increases, the relaxivity per metal ion is reduced. The number of Gd(III) chelates varies from one (MS-325) to four, but despite this four-fold increase in the number of IEMs, the total relaxivity increases by only about 50%. This modest increase in total relaxivity is a consequence of the decreasing relaxivity per Gd(III) ion. Note that the average $RI_{bound}$ per Gd(III) decreases from 47 mM$^{-1}$ s$^{-1}$ to 14.9 mM$^{-1}$s$^{-1}$ despite the contrast agent being bound. This decrease is due to local chelate motion which surprisingly increases with the number of IEMs despite multiple aromatic rings in the single TBM.

Apparently, increasing the number of chelating moieties also increases the rotational freedom of the molecule, at least near the sites of gadolinium chelation. The decrease in relaxivity is especially notable as the size increases beyond two chelated gadolinium ions per multimer molecule. For example, in the case of M8-03 the total relaxivity per gadolinium is only about 15 mM$^{-1}$s$^{-1}$, approximately one third that observed for MS-325. The total relaxivity for the compound M8-03 is therefore only 60 $mM^{-1}s^{-1}$, just 1.3 times that of MS-325 although four times as many IEMs are present. Obviously, such a modest increase in relaxivity does not justify the added synthetic complexity and cost to develop such agents for in vivo MR imaging. Thus, the simple combination of multiple image enhancing moieties with a single target binding moiety does not generate a commensurate increase in relaxivity. Thus, there exists a need to synthesize multimeric MRI contrast agents wherein the relaxivity at each chelate is maintained even as the number of IEMs increases.

Overall, immobilization of a target-bound contrast agent can be remarkably effective at increasing the relaxivity for a single chelate (e.g. MS-325) but is rather ineffective for multimeric chelates. That is, in order to increase the relaxivity at each chelate site, it is necessary to both reduce the overall rotational correlation time for the molecule and to reduce the local chelate motion at each chelation site. There remains a need for a mechanism to efficiently immobilize target-binding multimeric contrast agents so that more effective signal enhancement is produced during imaging.

A method is needed to improve signal contrast at specific targets. The problem has been approached by (1) increasing the number of IEMs, or (2) decreasing the flexibility of the molecule. Increasing the number of IEMs has been unsuccessful because the contrast agents are not of homogeneous size and structure, pose synthetic difficulties, are difficult to target, or fail to increase contrast proportionately with the increase in IEM number. Decreasing the flexibility has been unsuccessful because rigid contrast agents create high background when unbound. Binding of a multimer to a target through a single TBM is not sufficient to both decrease flexibility and increase relaxivity significantly. Therefore, a need exists to improve contrast at specific targets by increasing the number of IEMs while simultaneously decreasing the flexibility of the molecule only when bound to the target.

SUMMARY OF THE INVENTION

The current invention provides a mechanism to greatly improve the efficacy of in vivo contrast agents. Great improvements in contrast (signal to noise) at the target are possible if multimeric contrast agents are flexible in the unbound state (resulting in low relaxivity and a weak signal) and less flexible in the bound state (resulting in high relaxivity and a strong signal). That is, it is more important to rigidify the multimeric contrast agent in the bound state than in the unbound state since this minimizes background in the unbound state while high relaxivity is maintained in the bound state. Such agents are bound to proteins or other specific targets by non-covalent interactions at two or more separate loci. Multilocus binding is achieved by incorporating two or more TBMs into the agent, each of which has some affinity for one or more sites on the target.

More specifically, the invention relates to the use of "multilocus," non-covalent interactions between a contrast agent with multiple IEMs (a "multimer") and a target to simultaneously 1) induce binding to the target (thus giving specificity), 2) anchor several IEMs to the target and 3) thereby rigidify the multiple IEM structure. A key aspect of the invention is that the contrast agent is less flexible in the bound state than in the unbound state. Binding of the contrast agent to the target increases the relaxivity and signal intensity of a metal chelate IEM by increasing the overall rotational correlation time of the metal ion—imaging atom vector, i.e., by limiting rotational motion. Multilocus binding enables further relaxivity enhancement by decreasing the flexibility of the multiple chelate structure in the bound state both in general and at the local sites where chelate motion occurs. The flexibility of the molecule in the unbound state provides particular advantages over previously described multimeric MRI agents with rigid structures linking the chelates and with no difference in rigidity between a bound and unbound state. [Ranganathan, R. S., et al., *Invest. Radiol.*, 33: pp. 779–797 (1998)]. The multilocus binding concept for multimeric chelates is shown schematically in FIG. 2. Specifically, FIG. 2 shows the key components of an example multimeric contrast agent bound to a target through multilocus interactions. Three important features of the contrast agent illustrated by the drawing are: (1) multiple separate TBMs, which may be the same or different, promote binding to the target (thus giving specificity and improved affinity); (2) when bound to the target, TBMs anchor the multimer structure at several positions along the scaffold, thus rigidifying the multiple chelate structure; and (3) relaxivity is enhanced to a greater extent when bound than when free in solution, thus improving imaging contrast at a specific target.

In addition to the improvement in image contrast, this invention offers synthetic advantages. A synthetically rigidified chemical framework (such as a fused ring or complex macrocycle) is not necessary since immobilization and rigidification occur upon binding by multilocus attachments to the target. Therefore, there are fewer limitations on the chemical framework structure. Additional benefits include:

a) Multilocus binding increases protein affinity and provides greater target specificity compared to a single interaction [Kramer, R. H. and Karpen, J. W., *Nature*, 395: pp. 710–713 (1998); Clackson, T. et al., *Proc. Natl. Acad. Sci.*, 95: pp. 10437–10442 (1998); Rao, J. et al., *Science*, 280: pp. 708–711 (1998); Mann, D. A., et al., *J. Am. Chem. Soc.*, 120: pp. 10,575–10,582 (1998); Spevak, W. et al., *J. Med. Chem.*, 39: pp. 1018–1020.(1996); Lee, R. T. et al., *Arch. Biochem. Biophys.*, 299: pp. 129–136 (1992)].

b) Multilocus binding slows the rate at which the agent dissociates from the target. Increasing the time that the agent remains bound results in an increased diagnostic utilization period.

c) Multilocus binding decreases the flexibility of the multiple chelate structure, reduces the local chelate motion, and thus improves the relaxivity at each metal center. Rigidification of the contrast agent in the bound state compared with the free molecule occurs only upon binding to produce greater imaging contrast. The free molecule induces a relatively small signal change compared with the bound form; consequently a surprisingly greater difference between the signal induced by the bound form relative to the signal induced by the free molecule can be attained. Contrast agents that are rigid in both the bound and unbound states lack this property.

d) The binding-dependent change in signal intensity is also applicable to other imaging modalities where a change in signal intensity may accompany binding, such as optical imaging. The signal intensity may increase or decrease upon binding. In some cases, decreased signal has been shown to correlate with the rigidity of the molecule [Rimet, O., Chauvet, M., Dell'Amico, M., Noat, G., and Bourdeaux, M. *Eur. J. Biochem.* (1995) 228: pp. 55–59]. In other cases, signal increases upon binding [Sudlow G., Birkett D. J., and Wade D. N. *Mol. Pharmacol.* 12: pp. 1052–61 (1976); Sudlow G., Birkett D. J., and Wade D. N. *Mol. Phar-*

*macol.* 11: pp. 824–32 (1975); Kane C. D. and Bernlohr, D. A. *Anal. Biochem.* 233: pp. 197–204; Lakowica, J. R. *Principles of Fluorescence Spectroscopy* Plenum Press, New York, N.Y. pp. 211–213 (1983)]. Multilocus binding could provide either greatly decreased signal intensity (and therefore greatly increased signal contrast) or greatly increased intensity compared to an optical contrast agent with only a single TBM. In either case, the change in signal intensity at the target site will result in improved signal contrast as a result of contrast agent binding.

The multilocus-binding contrast agents of the invention comprise IEMs, a scaffold to which multiple IEMs are attached directly or through optional linkers, and at least two separate TBMs. The TBMs may be the same or different. In some cases, the scaffold may actually comprise the IEM or a part of the IEM, for example, some chelating moieties may also serve as the scaffold or a part of the scaffold.

These multimeric/multilocus-binding compounds are unique in that the local motion of the IEMs is restricted and bound relaxivity is greatly enhanced by non-covalent binding of at least two TBMs to the target at several separate loci along the multimer structure. These interactions allow the multimer to bind the target protein in a "pseudo-cyclic" or a "zipper-like" fashion. This type of binding surprisingly decreases flexibility throughout the multimer, including the TBMS, scaffold, and individual IEMs. Thus, for IEMs that include chelates, local chelate motion is reduced and remarkably enhanced MRI signals are observed with multimers since the relaxivity is increased at each IEM. This increase distinguishes the contrast agents of the present invention from those of the prior art that bind through a single TBM and thus are not "pseudo-cyclized" or "zippered" to the targeted site. Contrast is further enhanced with multimeric/multilocus binding structures since they also produce a relatively low signal in the unbound state.

The invention has tremendous utility for all targeted MRI and optical applications, including the targeting of image-enhancing agents to biological structures, such as serum albumin and other diagnostically relevant targets, such as blood clots, particularly in those applications where multiple binding sites for the multimeric/multilocus binding contrast agent exist. These binding sites need not be identical, just in close enough proximity to be simultaneously bound by the TBMs on the contrast agent.

DETAILED DESCRIPTION OF THE INVENTION

In order that the invention herein described may be more fully understood, the following detailed description is set forth.

Commonly used chemical abbreviations that are not explicitly defined in this application may be found in The American Chemical Society Style Guide; Second Edition; American Chemical Society, Washington, D.C. (1997) or Journal of Organic Chemistry; Guidelines to Authors (Revised May 2000), Copyright© 2000 American Chemical Society also available at http://pubs.acs.org/instruct/joceah.pdf.

The publications cited herein are incorporated by reference.

For the purposes of this application, DTPA refers to a structure of any one of Formulae (II)–(V):

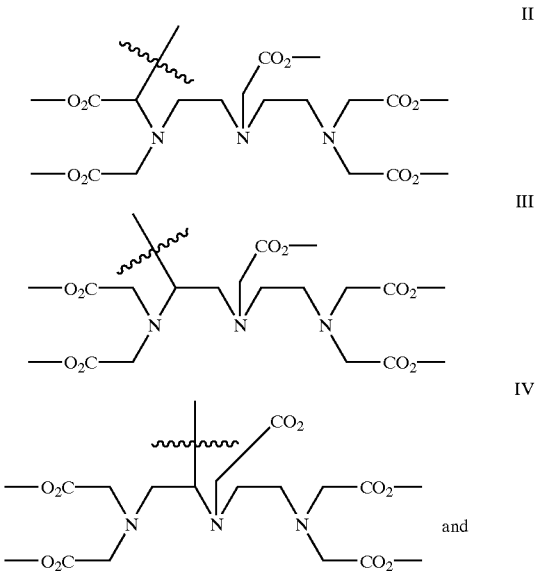

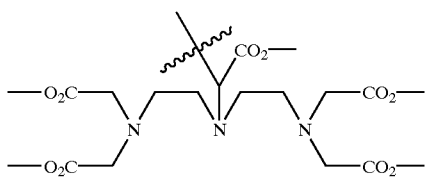

The term "specific affinity" as used herein, refers to the capability of the contrast agent to be taken up by, retained by, or bound to a particular biological component to a substantially greater degree than other components. Contrast agents which have this property are said to be "targeted" to the "target" component. Contrast agents that lack this property are said to be "non-specific" agents.

The term "relaxivity" as used herein, refers to the increase in either of the quantities $1/T_1$ or $1/T_2$ per millimolar (mM) concentration of paramagnetic ion, wherein $T_1$ is the longitudinal, or spin-lattice, relaxation time and $T_2$ is the transverse, or spin-spin, relaxation time of water protons or other imaging or spectroscopic nuclei, including protons found in molecules other than water. Relaxivity units are $mM^{-1}s^{-1}$.

The term "open coordination site" as used herein, refers to a site on a metal chelate that is generally occupied by water or solvent molecules.

The term "formation constant" for purposes herein is defined as the equilibrium constant for the reaction describing the formation of that compound.

The term "multimer" for purposes herein is defined as a contrast agent or a subunit thereof comprising two or more IEMs.

The term "multilocus" for purposes herein refers to two or more positions of covalent TBM attachment to the "scaffold" (defined below) of a contrast agent.

The term "multilocus binding" for purposes herein refers to non-covalent interactions of the two or more different TBMs with a target. These non-covalent interactions are independent from one another and may be, inter alia, hydrophobic, hydrophilic, dipole-dipole, pi-stacking, or Lewis acid-base interactions.

The term "pseudo-cyclic structure" for purposes herein refers to a contrast agent bound through non-covalent interactions to a target at two different loci through two TBMs. (see FIG. 3 which shows representative examples of multilocus binding structures).

Figure 1:
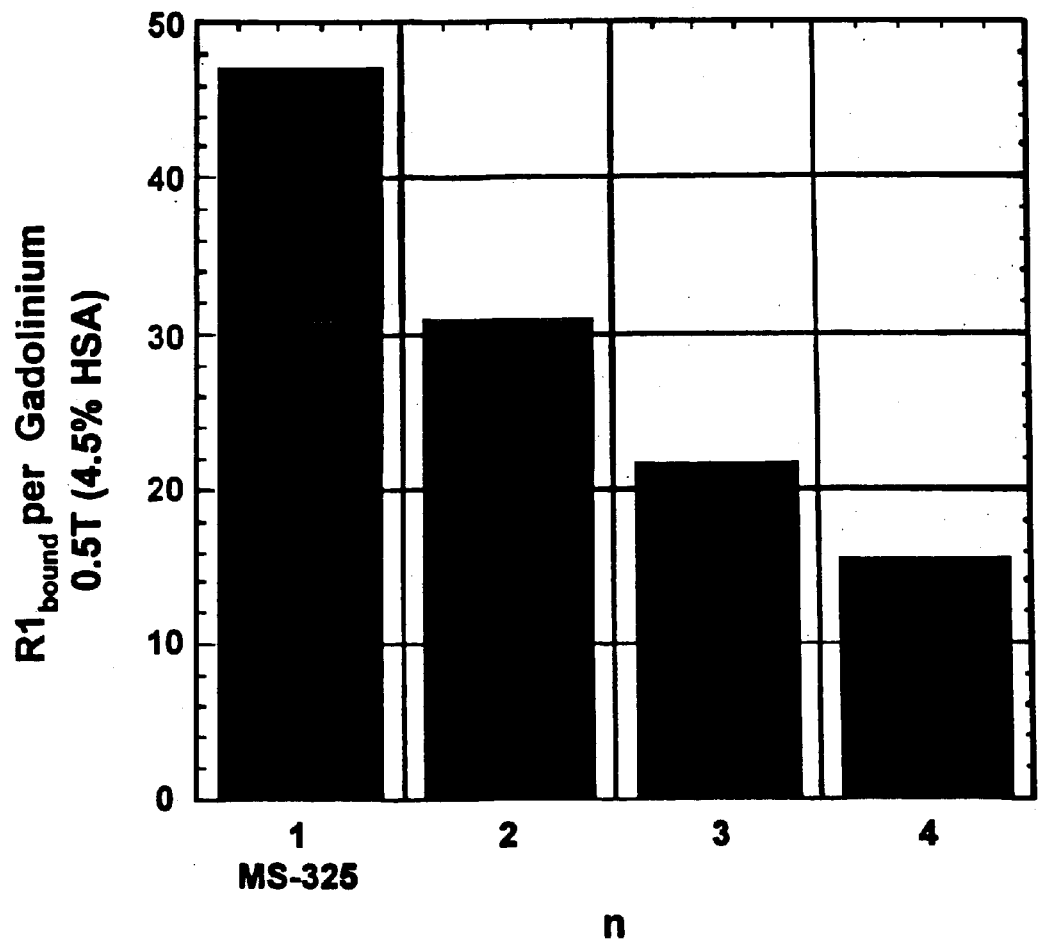
FIG. 1. Plot of bound relaxivity (per gadolinium) for a series of multimeric contrast agents containing a single diphenylcyclohexyl protein binding group. As the multimer size increases, the data indicate that the relaxivity per gadolinium decreases.
Figure 2:
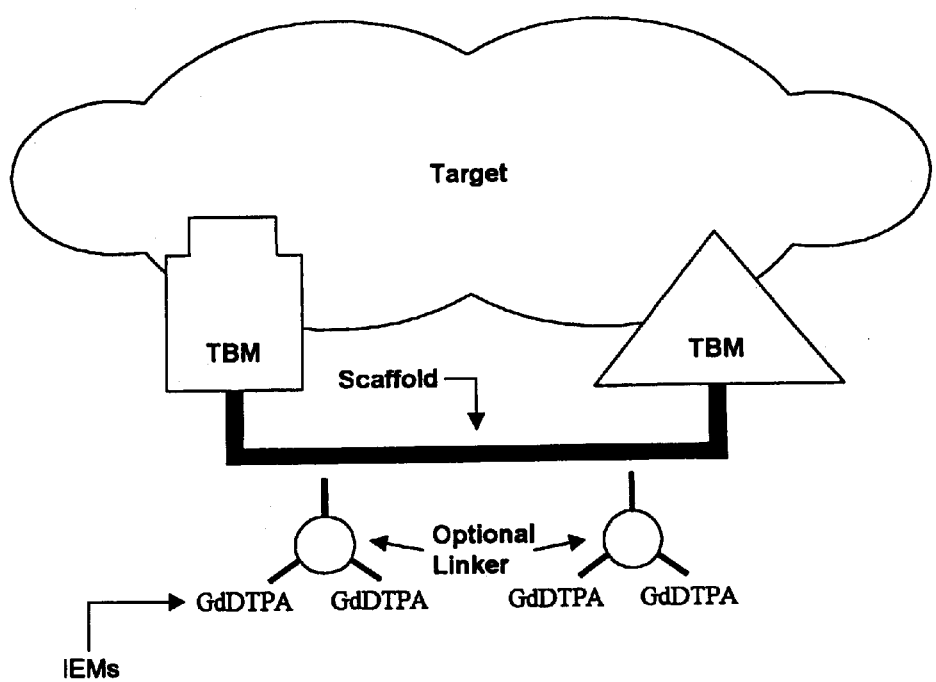
FIG. 2. Schematic drawing showing the key components of an example multimeric contrast agent bound to a target through multilocus interactions
1) Multiple separate TBMs promote binding to the target (thus giving specificity and improved affinity). The TBMs may be the same or different.
2) When bound to the target, TBMs anchor the multimer structure at several positions along the scaffold, thus rigidifying the multiple chelate structure.
3) Relaxivity is enhanced to a greater extent when bound than when free in solution, thus improving imaging contrast at a specific target.
Figure 3:
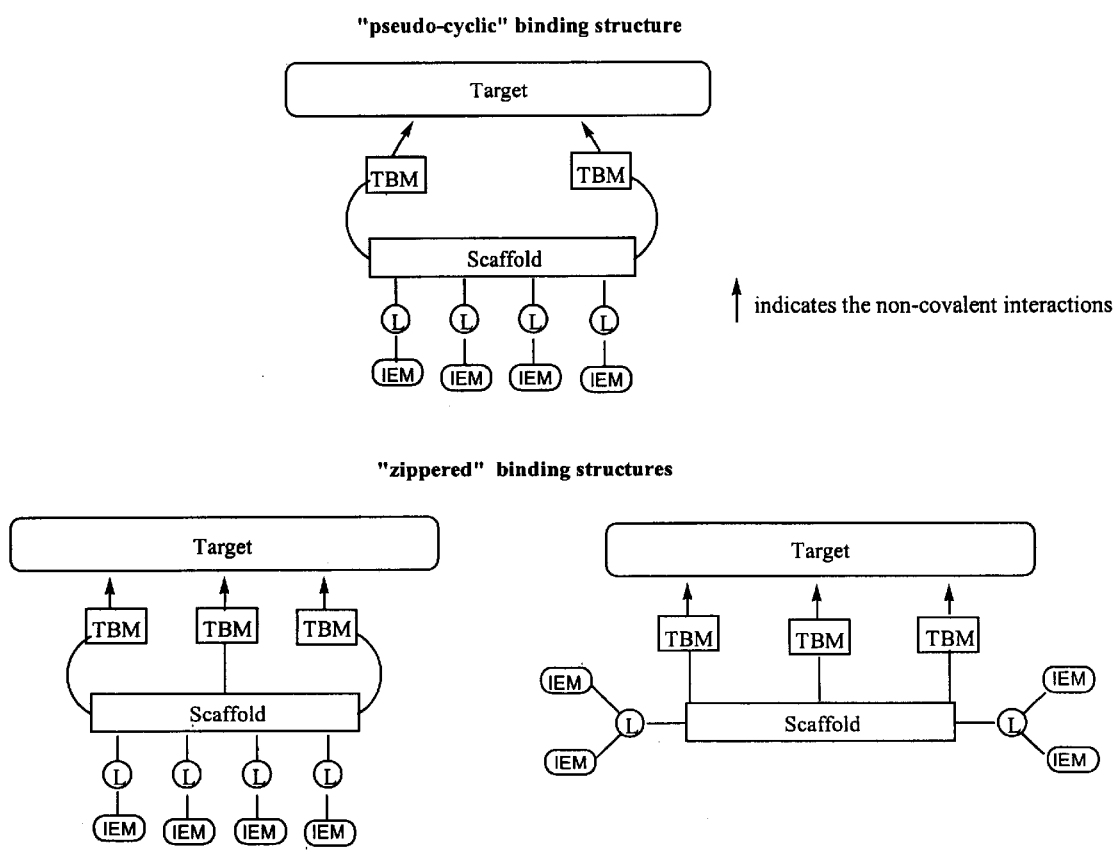
FIG. 3. Representative examples of multilocus binding structures

The term "zipper structure" for purposes herein refers to a contrast agent bound through non-covalent interactions to a target at three or more different loci through three or more TBMs (see FIG. 3).

The present invention relates to novel compounds which enhance the contrast in diagnostic imaging following a decrease in flexibility upon binding to a target. These compounds comprise:

a) two or more Image Enhancing Moieties ("IEMs");
b) two or more Target Binding Moieties ("TBMs"), providing for in vivo localization and multimer rigidification;
c) a scaffold framework for attachment of the above ("scaffold");
d) optional linkers for attachment of the IEMs to the scaffold ("linker").

Diagnostic imaging techniques contemplated for use with this invention include, but are not limited to, MRI and ultraviolet-visible-infrared light imaging.

Image Enhancing Moiety ("IEM")

According to the present invention, the IEM can be a chemical or substance which is used to provide the signal or to improve contrast during imaging. In addition, the IEM or a part of an IEM may be optionally used as a scaffold or a part of the scaffold and may possess a minor targeting function.

The IEM may comprise an organic molecule, metal ion or chelate. Many examples of IEMs have been described [Bonnemain, B. J. *Drug Target.*, 6: pp. 167–74 (1998); Swanson, D. P., et al., *Pharmaceuticals in Medical Imaging: Radiopaque Contrast Media, Radiopharmaceuticals, Enhancement Agents for Magnetic Resonance Imaging and Ultrasound*, McGraw Hill, Inc., (1990); Johnson, I. *Histochem. J.*, 30: pp. 123–40 (1998)].

A particularly useful IEM is a physiologically compatible metal chelate with one or more cyclic or acyclic organic chelating agents complexed to one or more metal ions. Metal ions preferred for optical imaging include those with atomic numbers 13, 21–31, 39–42, 44–50, or 57–83. Metal ions preferred for MRI include those with atomic numbers 21–29, 42, 44, or 57–83, and more preferably a paramagnetic form of a metal ion with atomic numbers 21–29, 42, 44, or 57–83. Particularly preferred paramagnetic metal ions are selected from the group consisting of Gd(III), Fe(III), Mn(II and III), Cr(III), Cu(II), Dy(III), Tb(III and IV), Ho(III), Er(III), Pr(III) and Eu(II and III). The most preferred is Gd(III).

If the IEM is a metal chelate, it must not dissociate to any significant degree during the imaging agent's passage through the body, including while bound to the target tissue. Significant release of free metal ions can result in toxicity, which would generally not be acceptable.

In general, the degree of toxicity of a metal chelate is related to its degree of dissociation in vivo before excretion. Toxicity generally increases with the amount of free metal ion, that is, a high formation constant is preferred to prevent toxic concentrations of free metal ions. Particularly preferred are formation constants of at least $10^{15}$ $M^{-1}$, or at least $10^{16}$ $M^{-1}$, or at least $10^{17}$ $M^{-1}$, or at least $10^{18}$ $M^{-1}$, or at least $10^{19}$ $M^{-1}$, or at least $10^{20}$ $M^{-1}$, or at least $10^{22}$ $M^{-1}$, or at least $10^{24}$ $M^{-1}$ or higher. If the kinetics of metal ion dissociation are very slow, then a complex having a lower formation constant, i.e. of at least $10^{10}$ $M^{-1}$, may be sufficient.

Toxicity is also a function of the number of open coordination sites in the complex. In general, fewer water coordination sites lowers the tendency for the chelating agent to release the paramagnetic metal. Preferably, therefore, the complex contains two, one, or zero open coordination sites. The presence of more than two open sites in general will unacceptably increase toxicity by release of the metal ion in vivo.

Relaxivities $R_1$ and $R_2$, defined as the increase in $1/T_1$ or $1/T_2$, respectively, per mM of metal ion, measure the ability of a contrast agent to enhance the relaxation rate of spectroscopic or imaging nuclei. Relaxivity units are $mM^{-1}s^{-1}$. For the most common form of clinical MRI, water proton MRI, relaxivity is higher when the paramagnetic ion bound to the chelating ligand still has one or more open coordination sites for water exchange (R. B. Lauffer, *Chemical Reviews*, 87: pp. 901–927 (1987)). However, this must be balanced with the stability of the metal chelate, which generally decreases with increasing numbers of open coordination sites, and the toxicity as mentioned above. Preferably, therefore, except for iron chelates, Fe(II) or Fe(III), the complex contains only one or two open coordination sites. For Gd(III) one or two open coordination sites is most preferred.

In order to effectively enhance MRI images, the complex must be capable of increasing the relaxation rates, or relaxivities, $1/T_1$ (longitudinal, or spin-lattice) and/or $1/T_2$ (transverse, or spin-spin) of the spectroscopic nucleus. The spectroscopic nucleus is preferably a water proton, but other common spectroscopic nuclei include $^{31}P$, $^{13}C$, $^{23}Na$, $^{19}F$ and protons found in molecules other than water. The spectroscopic nucleus may comprise the IEM, TBM, other biomolecules or injected biomarkers.

In the case of MRI contrast agents, increases in the relaxivities ($1/T_1$ or $1/T_2$) generally occur through dipole-dipole interactions between the paramagnetic ion of the contrast agent and the nuclei undergoing relaxation (e.g. hydrogen atoms in water molecules). It is known that the efficiency of this dipolar interaction (i.e. the relaxivity) is improved if the rate at which the vector defined by the two dipoles (i.e. the vector defined by the paramagnetic ion and a water hydrogen atom) rotates is slowed (R. B. Lauffer, Chemical Reviews, 87: pp. 901–927 (1987)).

The time taken for the vector to rotationally diffuse one radian is referred to as the "rotational correlation time"; the inverse of the rotational correlation time is the "rotational rate." In general, large molecules rotate more slowly in solution than smaller molecules. One method of increasing relaxivity is to form a non-covalent adduct between a small molecule contrast agent and a macromolecule. By forming an adduct, the rotational correlation time of the dipolar vector will likely be the same as that of the macromolecule. However the small molecule may still be able to rotate about one or more axes (so-called "local chelate motion"). The rotational correlation time of the dipolar vector is then a function of this local chelate motion and of the global motion of the macromolecule adduct. Non-covalent adducts of macromolecules will have rotational correlation times that are less than or equal to that of the macromolecule itself; the less local chelate motion there is, the closer the rotational correlation time of the non-covalent adduct approaches that of the macromolecule.

In the case of MRI contrast agents, increases in relaxivity generally occur through dipole-dipole interactions between the metal ion of the contrast agent and the nuclei undergoing relaxation (e.g. the water hydrogen atoms). In addition to increasing the $1/T_1$ or $1/T_2$ values of tissue nuclei via dipole-dipole interactions, MRI agents can affect two other magnetic properties that increase their use and value for clinical purposes:

1) an IEM containing a metal chelate of high magnetic susceptibility, particularly chelates of Dy, Gd, Tb, or Ho, can alter the MRI signal intensity of tissue by creating microscopic magnetic susceptibility gradients (A. Villringer et al, Magn. Reson. Med., 6: pp. 164–174 (1988)). No open coordination sites on a chelate are required for this application.

2) an IEM containing a metal (e.g. Tm or Dy) chelate can also be used to shift the resonance frequency of the spectroscopic nucleus. The spectroscopic nucleus is preferably a water proton, but other common spectroscopic nuclei include $^{31}P$, $^{13}C$, $^{23}Na$, $^{19}F$ and protons found in molecules other than water. The spectroscopic nucleus may comprise the contrast agent, the target, or water. Here, depending on the nucleus and strategy used, zero to three open coordination sites may be employed.

A variety of chelating ligands may be used as IEM moieties in various embodiments of the invention. Such chelating ligands include but are not limited to derivatives of diethylenetriamine pentaacetic acid (DTPA) and derivatives thereof; 1,4,7-triazacyclononane; 1,4,7,10-tetraazacyclododecane (Cyclen) and derivatives thereof; 1,4,7,10-tetraazacyclododecane-1,7-bis(acetic acid tert-bu-ester) (DO2A-t-bu-ester); 1,4,7,10-tetraazacyclododecane-1,4,7-tris(acetic acid, t-bu-ester) (DO3A-t-bu-ester); 1,4,7-tris(tert-butoxycarbonyl)-1,4,7-tetraazacyclododecane (DO3-t-BOC); 1,4,7,10-tetraazacyclododecane-1,4,7,10-tetraacetic acid (DOTA) and derivatives thereof; 1,4,7,10-tetraazacyclododecane-1,4,7,10-tetrakis(methylene phosphonic acid) (DOTP); 1,4,7,10-tetraazacyclododecane-1,4,7,10-a, a', a",a'''-tetrakis(methylacetic acid) (DOTMA); ethylenediamine-tetra-acetic acid (EDTA); 1,4,8,11-tetraazacyclotetradecane-1,4,8,11-tetraacetic acid (TETA); ethylenebis-(2-hydroxy-phenylglycine)(EHPG) and derivatives thereof, including 5-Cl-EHPG, 5-Br-EHPG, 5-Me-EHPG, 5-t-Bu-EHPG, and 5-sec-Bu-EHPG; benzodiethylenetriamine pentaacetic acid (benzo-DTPA) and derivatives thereof, including dibenzo-DTPA, phenyl-DTPA, diphenyl-DTPA, benzyl-DTPA, and dibenzyl DTPA; bis-2(hydroxybenzyl)-ethylene-diaminediacetic acid (HBED) and derivatives thereof; the class of macrocylcic compounds which comprise at least 3 carbon atoms, more preferably at least 6, and comprise at least two heteroatoms (O and/or N), said macrocylcic compounds may comprise one ring, or two or three rings joined together at the heteroatom ring elements, e.g., benzo-DOTA, dibenzo-DOTA and benzo-NOTA, where NOTA is 1,4-triazacyclononane-N,N',N"-triacetic acid, benzo-TETA, benzo-DOTMA, benzo-TETMA, where TETMA is 1,4,8,11-tetraazacyclo-tetradecane-1,4,8,11-(methyl tetraacetic acid); derivatives of 1,3-propylenediaminetetraacetic acid (PDTA) and triethylenetetraaminehexaacetic acid (TTHA); and derivatives of 1,5,10-N,N',N"-tris(2,3-dihydroxybenzoyl)aminomethylbenzene (MECAM).

Many suitable chelating ligands for MRI agents are known in the art. These metal chelates can also be used for other forms of biological imaging (e.g., optical imaging). In fact, a series of fluorescently detectable MRI contrast agents have recently been described [Hüber, M. M. et al., Bioconjugate Chem.,9: pp. 242–249 (1998)]. For MRI imaging, preferred IEMs include paramagnetic gadolinium chelates such as gadolinium diethylenetriaminepentaacetic acid (GdDTPA), gadolinium tetraamine 1,4,7,10-tetraazacyclododecane-N,N',N",N'''-tetraacetic acid (GdDOTA) and gadolinium 1,4,7,10-tetraazacyclododecane-1,4,7-triacetic acid (GdDO3A). It is known in the art that other metals may be substituted for Gd(III) in certain applications. A preferred chelator for use in the invention is DTPA. Examples of representative chelators and chelating groups contemplated by the present invention are described in WO 98/18496, WO 86/06605, WO 91/03200, WO 95/28179, WO 96/23526, WO 97/36619, PCT/US98/01473, PCT/US98/20182, and U.S. Pat. No. 4,899,755, all of which are herein incorporated by reference.

Target Binding Moiety ("TBM")

According to the present invention, the second component of the contrast agent is two or more Target Binding Moieties (TBMs). The TBMs of the compound (1) allow the contrast agent to bind to proteins or other targets and (2) decrease the flexibility of the molecule in the bound state. This creates an increased concentration of the imaging agent at the site to be imaged and increases the relaxivity in the bound state. For vascular blood pool imaging, serum albumin is a preferred target. Other protein targets include, but are not limited to, alpha acid glycoprotein, fibrinogen, fibrin, and collagen. For imaging clots, fibrin is a preferred target. The TBM therefore must be selected to achieve specificity and high binding affinity for the appropriate protein. Since HSA is present at high concentration in serum (approximately 0.6 mM) and binds a wide array of molecules with reasonably high affinity, it is the preferred target plasma protein for blood pool contrast agents. HSA is a particularly preferred target for cardiovascular imaging.

A wide range of lipophilic or amphiphilic TBMs will efficiently bind to various targets, including Human Serum Albumin (HSA). These include but are not limited to aromatic, and saturated or unsaturated aliphatic groups with 4–200 carbons wherein each carbon is optionally substituted with or replaced by oxygen, nitrogen, halogen, sulfur, or other atoms that can covalently bind carbon. For binding to other protein targets with high specificity, special targeting groups are often required. Targeting groups of sufficiently high affinity and specificity may be identified using modern techniques, such as combinatorial chemistry, high throughput screening, phage display, systemic evolution of ligands by exponential enrichment (SELEX) and other methods as described, for example, in U.S. Pat. Nos. 5,475,096, 5,595,877, and 5,270,163 [see Gold et al. Ann. Rev. of Biochem., 64: pp. 763–797 (1995)], herein incorporated by reference.

The extent of binding of a TBM to a target, such as HSA or fibrin, can be assessed by a variety of equilibrium binding methods. For example, binding to HSA can be measured by ultrafiltration. In a typical binding measurement using ultrafiltration, the targeting group is mixed with 4.5% weight/volume HSA in a pH 7.4 buffer. The sample is loaded into a commercially available centrifugation apparatus equipped with a 30 KDa molecular weight cutoff filter (Millipore Ultrafree MC Low Binding Regenerated Cellulose 30 KDa mol. wt. cutoff catalog #UFC3LTK00), permeable to the targeting group, but not HSA. A small portion (5–10%) of the sample volume is filtered by centrifugation at 2000×g for 20 min through the cutoff filter, and the concentration of unbound targeting group in the sample is measured in the filtrate.

For measuring binding to fibrin, a fibrin clot may be formed in a well of a microtiter plate and contacted with the targeting group. After an incubation time sufficient to establish equilibrium, the supernatant is removed by aspiration (the insoluble fibrin remains bound as a gelled clot to the bottom of the well). The concentration of unbound targeting group in the supernatant is then measured. In both methodologies, the concentration of bound targeting group is determined as the difference between the total targeting group concentration initially present and the unbound targeting group concentration following the binding assay. The bound fraction is the concentration of bound targeting group divided by the concentration of total targeting group. Preferably at least 10%, more preferably at least 50%, still more preferably at least 80%, still more preferably at least 90% of the contrast agent is bound to the desired target at physiologically relevant concentrations of drug and target. More preferably at least 92%, even more preferably at least 94%, and most preferably 96% or more of the contrast agent is bound to the target according to the ultrafiltration or microtiter plate methods.

For additional details concerning target binding moieties which comprise fibrin-binding peptides, see U.S. Provisional Patent Application No. 60/146,425 entitled BINDING MOIETIES FOR FIBRIN; identified as DYX-010.0Prv and U.S. Provisional Patent Application No. 60/146,414 filed concurrently on the same day (Jul. 29, 1999) from which the present utility application claims priority; and continuations thereof all of which are incorporated herein by reference in their entirety.

The TBMs may be very diverse depending on the nature of the target and the specific requirements of the binding. Examples of useful TBMs include drugs, lipophilic or amphiphilic organic molecules, porphyrins, receptor ligands, steroids, lipids, hormones, peptides, oligonucleotides (DNA, RNA or chemically modified versions thereof), carbohydrates or other biomolecules or substances that are known to bind with sufficiently high affinity to one or more components in the specific tissue desired to be imaged. In certain embodiments, one TBM may have higher affinity for the target than the other(s), in which case the higher affinity TBM is designated the "primary" TBM. Thus, all other TBMs with binding affinities lower than that of the primary TBM are designated "secondary."

More preferred TBMs are those that bind reversibly to proteins in plasma, interstitial space (the fluid between cells), or intracellular space. While many biomolecules or substances that bind to a specified target could be used, most useful are those that bind to proteins.

The secondary TBMs may be the same or different than the primary TBM. The number of secondary TBMs may vary from one to ten or more. The exact number of secondary TBMs required will depend on the specificity of the TBMs for the target and the affinity of the TBMs for the target. The additional binding interactions provided by the secondary TBMs must be sufficient to tether the complex and decrease the rotational correlation time at each chelation site. The resulting increased relaxivity provides adequate contrast enhancement of the image. Secondary TBM binding interactions and affinity for the target may be less specific than demanded by the primary targeting TBM, since the initial binding of the primary TBM to the target may provide the necessary specificity of target recognition. In some cases, the target may comprise dimeric binding sites, in which case two identical TBMs would be preferred.

Targets for the contrast agents described in this application are extensive and varied. The target can be any body compartment, cell, organ, or tissue or component thereof. Preferred targets are those that are of diagnostic and therapeutic relevance, i.e. those that are associated with disease states. Particularly preferred targets are those in association with body fluids, and particularly those in association with blood, plasma, lymph and fluids of the central nervous system. Other preferred targets are proteins that either exist in high concentration or have a large number of binding sites for certain ligands. Multiple binding sites provide contact for one or more secondary TBMs. Included among such target proteins are enzymes and glycoproteins.

The Scaffold for Attachment of IEMs and TBMs

Figure 4:
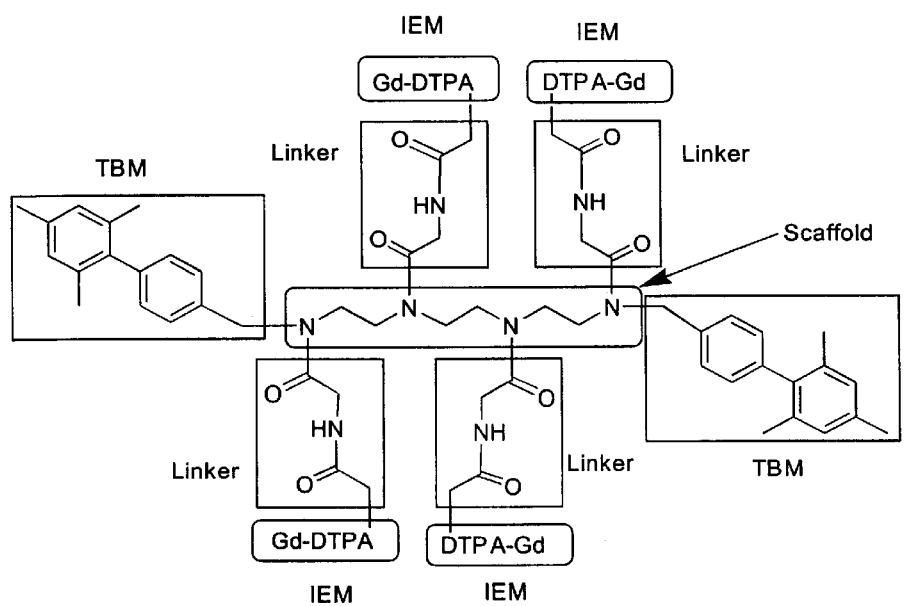
FIG. 4. An example of the multilocus binding multimer with a linear linker

The present invention provides for a third component to the multimer contrast agents, namely a chemical framework or "scaffold" structure to which the IEMs and TBMs may be attached, as depicted in FIG. 4. specifically, FIG. 4 shows an example of a multilocus binding multimer with a linear linker. The scaffold is the chemical framework between two or more TBMs to which two or more IEMs may be attached at different positions directly or through the linkers to form the multimeric/multilocus binding compounds. The novel compounds comprising these scaffold structures restrict the local chelate motion by non-covalent binding of the TBMs to a target at several (at least two) separate loci. The multimer contrast agent binds a target in a "pseudo-cyclic" or a "zipper-like" fashion, creating an interaction at two or more loci. This type of binding creates rigidity throughout the multimeric contrast agent structure, including the binding group, scaffold, and individual IEMs.

In general, scaffold structures will be highly diverse organic molecules that may include from one to ten of repeated monomeric subunits. The scaffold can be either open chained or cyclic. TBMs are covalently attached to the interior or termini of the structure. In every case, there must be at least two separate TBMs to tether the molecule to the target. The TBMs may either be the same (homogeneous) or different (heterogeneous). Heterogenous TBMs may exhibit either different or similar binding affinities for the target.

Both open chained and cyclic scaffolds also provide a supporting structure for the attachment of IEMs. The number of IEMs may vary from two to about 12. The IEMs may be interspersed with TBMs, and the IEMs may be attached either to the interior part of a linear scaffold structure or to the ends of the structure, optionally via a linker, but to at least two different positions of the structure. The IEMs may either be the same (homogeneous) or different (heterogeneous). Heterogenous IEMs may exhibit either different or similar contrast generating ability.

Within the set of open chained scaffolds, many types of structures can be synthesized using standard techniques. Particularly advantageous are scaffolds that have regularly repeated heteroatoms throughout the structure. Heteroatoms generally allow for easy attachment of IEMs or TBMs. Particularly preferred embodiments are oligomeric alkylene amine scaffolds. These oligomeric alkylene amine scaffolds may be either branched or linear. That is, the structures may have either a linear framework with regularly spaced IEMs and TBMs, or the chemical framework may branch so that groups of IEMs and/or TBMs may emanate from a single site on the scaffold. The scaffolds may also terminate in heteroatoms such as oxygen (alcohols) or nitrogen (amines). Particularly preferred embodiments of open chained scaffolds, both branched and linear, have terminal alcohols or terminal amines.

Figure 5:
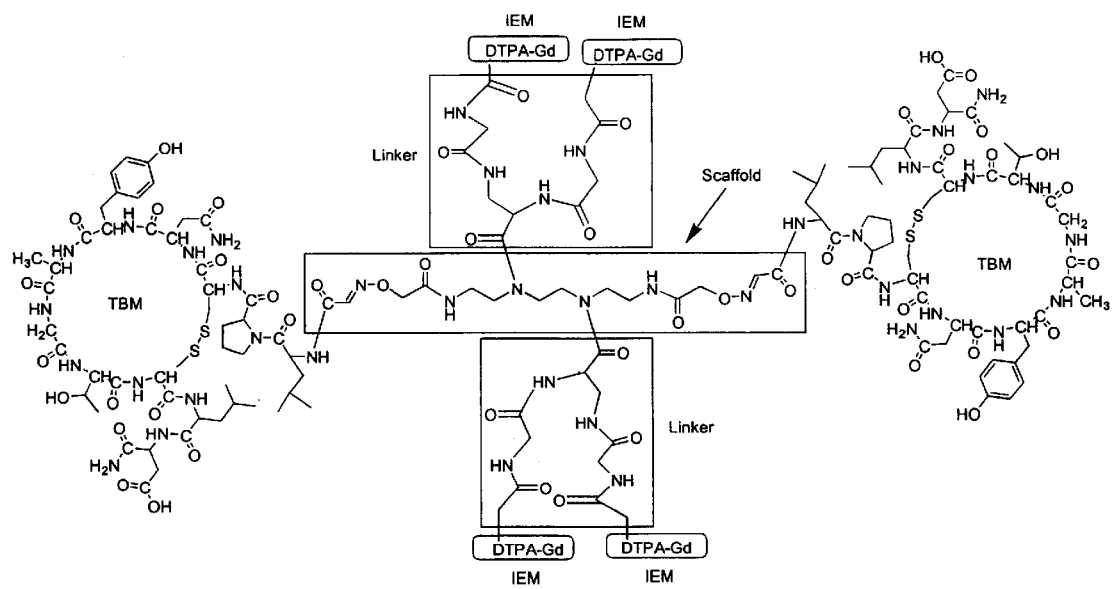
FIG. 5. An example of the multilocus binding multimer with a branched linker FIG. 6. Examples of Linear and Branched Polyamine Scaffolds FIG. 7. Examples of Oligomeric Scaffolds FIG. 8. Example of a Biodegradable Scaffold FIG. 9. Examples of Multimers Using a Part of Gadolinium Complexes as Scaffolds FIGS. 10A and 10B. Examples of Scaffolds with Cyclic Elements FIG. 11. Examples of Linkers with Multiple Connection Points FIG. 12. Compound M8-11

FIG. 4 shows an example of the multilocus binding of a multimer where the scaffold portion, IEM, TBMs, and (optional) linkers are clearly delineated. Another example of a multimer, this time with a branched linker, is illustrated in FIG. 5. Again, the scaffold portion, IEM, TBMs, and (optional) linkers are clearly delineated. In FIG. 5, the two TBMs are peptides attached to a polyamine scaffold, although these components in no way limit the scope of the invention.

A generic structure for a linear scaffold with a repeating amine sub-structure is given by Formula (VI),

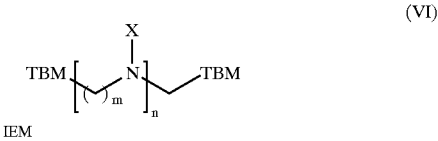

(VI)

X = L-IEM, TBM, or IEM wherein m can vary from 1 to 10, and n can vary from 2 to 10. Preferably, m is 1 to 2, 2 to 4, 4 to 6, 6 to 8, or 8 to about 10. Preferably, n is 2 to 4, 4 to 6, 6 to 8, or 8 to about 10.

A generic structure for a linear scaffold with a repeating amine sub-structure and terminal oxygens that allow the formation of ether-linked TBMs is given by Formula (VII):

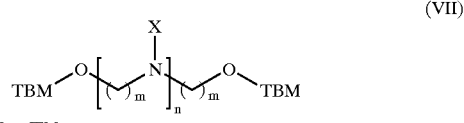

(VII)

X = L-IEM, TBM, or IEM wherein m can vary from 1 to about 10, and n can vary from 2 to 10. Preferably, m is 1 to 2, 2 to 4, 4 to 6, 6 to 8, or 8 to about 10. Preferably, n is 2 to 4, 4 to 6, 6 to 8, or 8 to about 10.

Scaffold structures are not limited to repeating substructures with amines, nor are they limited to structures containing terminal oxygens or nitrogens. The scaffold may contain any repeating substructure that allows attachment of IEMs, optionally via linkers, and TBMs. The carbon atoms comprising the scaffold may be optionally substituted with or replaced by heteroatoms selected from oxygen, nitrogen, sulfur, phosphorus, and halogens. The scaffold may also comprise substituents such as short chain hydrocarbons (1–10 carbon atoms). These hydrocarbon side chains may be optionally substituted with or replaced by heteroatoms selected from oxygen, nitrogen, sulfur, phosphorus, and halogens. Thus the scaffolds may comprise many common organic groups, for example, phosphodiesters, carbamates, sulfates, and sulfonyls. Likewise, substituents that are attached to the scaffold structure may also contain many common organic groups, for example, phosphodiesters, carbamates, sulfates, sulfonyls, and amino acids.

FIG. 6 shows some illustrative examples of linear and branched polyamine scaffolds along with corresponding examples of contrast agents comprising these scaffolds. FIG. 7 provides examples of oligomeric scaffolds along with corresponding examples of contrast agents comprising these scaffolds. Scaffolds comprising heteroatoms are one preferred embodiment of the present invention since heteroatoms allow easy attachment of IEMs and TBMs, optionally via linkers.

Figure 8:
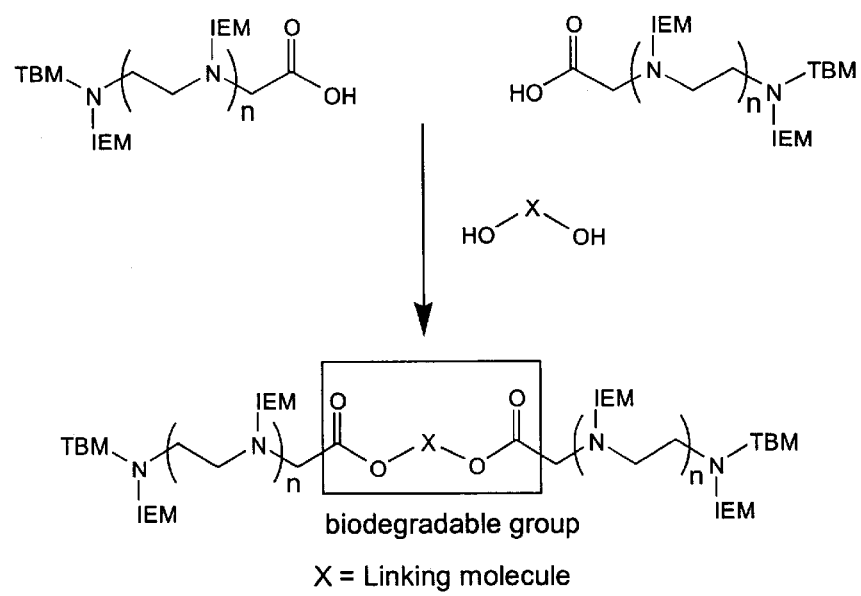

Another preferred embodiment for the scaffold is one in which the backbone of the scaffold is readily degraded in vivo. Biodegradable contrast agents have scaffold structures that can be degraded by, for example, enzymes that occur in the body of a mammal. Preferably the scaffold contains one or more biodegradable groups that can be specifically degraded by an enzyme. Particularly preferred biodegradable scaffolds are those that may be degraded by human enzymes. Because of the wide range of enzymatic activities known to exist, the exact structure of the biodegradable groups is variable. Particular preferred embodiments of the biodegradable group include, but are not limited to carbonyls, esters, diesters, phosphates, diphosphates, phosphodiesters, anhydrides, sulfonyl groups, sulfates, and carbamates. Such biodegradable scaffolds allow rapid metabolism of the multimeric contrast agent and lessens the chance of toxicity. One example of a biodegradable scaffold for a multimer is shown in FIG. 8. In this instance, the scaffold is formed from the condensation of two carboxylic acids in the presence of a molecule containing two terminal alcohols. The specific reaction conditions for such a condensation reaction are well known in the art.

Additionally, the biodegradable group may cleave upon a change in pH or temperature, or upon application of ultrasound or light energy. Such groups are well known in the prodrug literature. [Kratz, F., Beyer, U., and Schutte M. T., *Crit. Rev. Ther. Drug Carrier Syst.* 16: pp. 245–88 (1999); Dougherty, T. J., Gomer, C. J., Henderson, B. W., Jori, G., Kessel, D., Korbelik, M., Moan, J., and Peng, Q. *J. Natl. Cancer Inst.* 90: pp. 889–905 (1998); Wang, W., Jiang, J., Ballard, C. E., and Wang, B. *Curr. Pharm. Des.* 5: pp. 265–87 (1999)].

Figure 9:
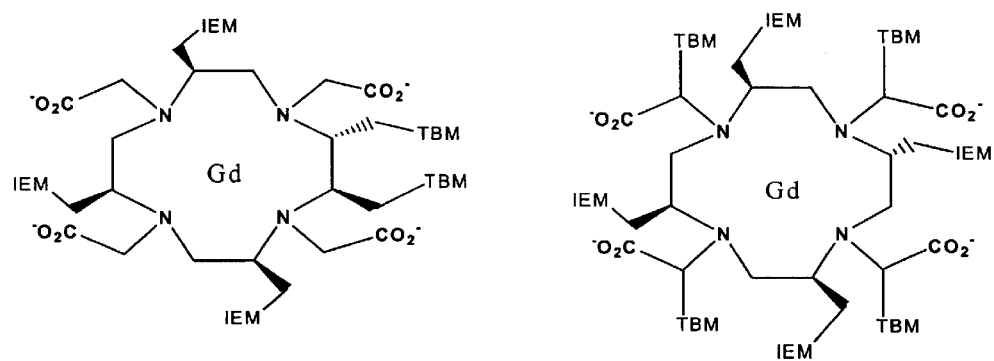

Scaffolds that comprise cyclic elements that chelate metal ions are another set of preferred embodiments of the present invention. More preferred are IEM-containing scaffolds that chelate gadolinium or provide for chelation of gadolinium within the scaffold as well as in separate IEMs that are attached to the scaffold. Examples of such scaffolds that use part of an IEM (in this case, gadolinium complexes) as part of the scaffold are shown in FIG. 9.

The classification of scaffolds into open chained and cyclic groups does not imply mutual exclusivity between the groups. A wide variety of open chained scaffolds that incorporate motion-constraining cyclic elements is contemplated. The cyclic portion of the scaffold may be a homocyclic or heterocyclic ring or rings. Thus, the rings may be highly constrained like, for example, a cyclopropyl ring, or may be a less conformationally constrained ring such as a cyclohexyl ring.

Both the open chained and cyclic portions of the scaffold may be optionally substituted with or replaced by heteroatoms selected from oxygen, nitrogen, sulfur, phosphorus, and halogens. The scaffold may also comprise substituents such as short chain hydrocarbons (1–10 carbon atoms). These hydrocarbon side chains may be optionally substituted with or replaced by heteroatoms selected from oxygen, nitrogen, sulfur, phosphorus, and halogens. Thus the scaffolds may comprise many common organic groups both in the open chained and cyclic portions of the scaffold. Some examples include, but are not limited to carbonyls, esters, diesters, phosphates, phosphodiesters, anhydrides, sulfonyl groups, sulfates, and carbamates.

The rings may also include derivatives of common biological cyclic compounds such as carbohydrates. Preferred embodiments of the cyclic elements include multiple rings systems, such as heterocyclic derivatives of decalin. Other examples include, but are not limited to, carbocyclic rings comprising from 3 to 7 atoms, wherein up to 4 atoms are optionally substituted with moieties selected from the group consisting of O, S, C(O), S(O), S(O)$_2$, and NH. The rings are optionally substituted with methyl groups and derivatives thereof, alkyl, alkenyl, or alkynyl groups comprising from 2–100 carbons, wherein up to 10 carbons are optionally substituted with heteroatoms selected from oxygen, nitrogen, sulfur, phosphorus, and halogens or are replaced by moieties selected from O, S, C(O), S(O), S(O)$_2$, and NH. Just as some scaffolds, such as amino acid-based scaffolds, may comprise TBMs, the scaffolds may likewise comprise IEMs. The IEMs can be any organic molecule, metal ion or chelate. Preferred embodiments are those with cyclic IEMs, even more preferable are cyclic IEMs that are metal chelates. Particular examples of such linear and cyclic combination scaffolds described above are shown in FIGS. 10A and 10B along with corresponding examples of contrast agents comprising these scaffolds.

Optional Linkers

The contrast agents of certain embodiments of the present invention are characterized by an optional linker through which IEMs are attached to a scaffold. The image enhancement moiety (IEM) and the target binding moiety (TBM) are described elsewhere herein. The linker moiety (L) can be any small subunit comprising 1 to 30 carbon atoms covalently connected by single or multiple bonds wherein up to 10 of the carbon atoms may be substituted with O, N, P, S, F, Cl, Br, H or I. The linker functions to connect the IEMs to the scaffold. Examples of linkers include linear or branched alkanes, alkenes, or alkynes optionally substituted with functional groups such as, carbonyl, ether, amide, amine, urea, thioether, aryl, phosphate, sulfonamide and the like. The preferred linkers of certain embodiments embody two or more functional chemical groups, one of which is attached to the scaffold and the others of which are attached to the IEMs.

The functional chemical groups may be the same or may be different. Examples of said functional groups include but are not limited to ketones, esters, amides, ethers, carbonates, sufonamides, alkanes, alkenes, alkynes, and carbamates. Examples of some preferred reagents to prepare linkers are amino acids, especially glycine, alanine, serine, homoserine, threonine, tyrosine, cysteine, aminophenylalanine, lysine, ornithine, 2,4-diaminobutyric acid, diaminopropionic acid, hydroxyproline, aspartic acid, and glutamic acid, diols, especially ethylene glycol, dihalides, especially ethylene dichloride, 2-mercaptoethanol, 2-aminoethanol, 1,2-diaminoethanol, dicarboxylic acids, especially oxalic acid, malonic acid, malic acid, succinic acid, fumaric acid, glutaric acid, and adipic acid, and other bifunctional, trifunctional and multifunctional small molecules.

Still other linkers without limitation, may be urea, acetal, ketal, double ester, carbonyl, thiourea, sulfone, thioester, ester, ether, disulfide, lactone, imine, phosphoryl, or phosphodiester linkages; substituted or unsubstituted saturated or unsaturated alkyl chains; linear, branched, or cyclic amino acid chains of a single amino acid or different amino acids (e.g., extensions of the N- or C-terminus of the fibrin binding moiety); malonic, succinic, glutaric, adipic and pimelic acids; caproic acid; simple diamines and dialcohols.

Preferably the molecular weight of the linker is well defined. The molecular weights can range in size from less than 100 to greater than 1000. Preferably the molecular weight of the linker is less than 200 and even more preferably is less than 100. In addition, it may be desirable to utilize a linker that is biodegradable in vivo to provide efficient routes of excretion for the imaging agents of the present invention. Depending on their location within the linker, such biodegradable functionalities can include ester, diester, amide, phosphoester, ether, acetal, and ketal functionalities.

Figure 11:
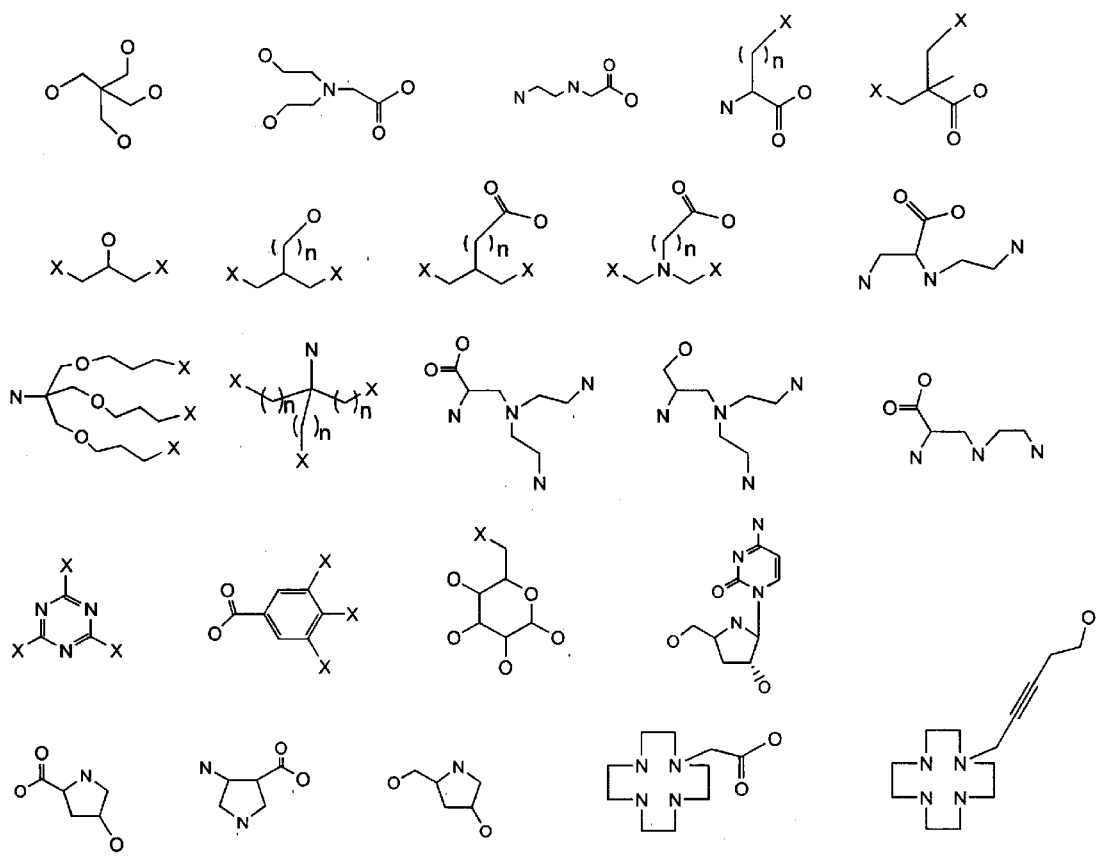

In general, known methods can be used to couple the metal chelate or other IEMs to the linker and the linker to the TBM. See, e.g., WO 95/28967, WO 98/18496, WO 98/18497. The present invention contemplates linking of the chelate at any position, provided the metal chelate retains the ability to bind the metal tightly in order to minimize toxicity. Examples of some linkers are shown in FIG. 11 with hydrogen atoms omitted for simplicity. The examples of FIG. 11 specifically show linkers with multiple connection points.

Contrast Enhancement in Conjunction with Multilocus Binding Interactions

The present invention in its different embodiments improves the average relaxivity of all the paramagnetic metal, e.g. gadolinium, centers in a target bound, multimeric chelate structure. The examples shown in Table 1 and Table 2 illustrate that target binding of a multiple IEM structure through a single TBM alone is not sufficient to improve the average bound relaxivity per Gd(III) to the same extent as observed for a comparable single IEM structure. Although binding through a single TBM slows the overall rotational correlation time of the multimer, the individual metal, e.g. gadolinium, chelates are apparently still free to rotate in a rather unencumbered fashion. This excess motion reduces the relaxivity at each metal center. Surprisingly, this is found to be true even when the multimer contains a TBM with two aromatic rings. In PCT WO 96/23526, McMurry et al. teach that the albumin-bound relaxivity of contrast agents with a single IEM is improved by the use of a plasma protein binding moiety (PPBM) comprising two or more aromatic rings in a non-planar orientation. As illustrated in Table 1, the use of such a TBM (diphenylcyclohexyl) provides excellent relaxivity enhancement for the single IEM case (MS-325), but surprisingly low albumin-bound relaxivity per IEM for the multimer analogs. In order to further improve the relaxivity of targeted multimers, the local motion of the chelating groups and chelated ion must be decreased.

This invention describes targeted multimers that exhibit high relaxivity as a result of multilocus binding interactions and the accompanying decrease in flexibility. The introduction of two or more TBMs positioned such that there is no significant decrease in relaxivity per IEM upon binding to a target has been found to remarkably improve the relaxivity so that in many cases, the relaxivity per IEM for the contrast agent in the bound state is similar to that previously observed with single IEMs (7–8 fold enhancement). The improvement in relaxivity per IEM results from the decreased flexibility of the target-bound multimer structure, including the attached IEMs. The increase in relaxivity upon binding is typically 1.5-fold or more. Preferred image resolution is the result of a relaxivity increase of at least 2 or 3 fold. More preferred increases in relaxivity are 4-fold, 5-fold, and 6-fold. Even more preferred increases in relaxivity are 7–8 fold, 9–10 fold or greater than 10 fold increases. The preferred relaxivity at 20 MHz and 37° C. is at least 10 mM$^{-1}$s$^{-1}$ per IEM, more preferably at least 15 mM$^{-1}$s$^{-1}$ per IEM, more preferably at least 20 mM$^{-1}$s$^{-1}$ per IEM, more preferably at least 25 mM$^{-1}$s$^{-1}$ per IEM, more preferably at least 30 mM$^{-1}$s$^{-1}$ per IEM, more preferably at least 35 mM$^{-1}$s$^{-1}$ per IEM, and most preferably at least 40 mM$^{-1}$s$^{-1}$ per IEM. Preferably the relaxivity of the contrast agent as a whole is greater than 60 mM$^{-1}$s$^{-1}$ at 20 MHz and 37° C.

The following data serve to illustrate the contrast enhancement that results from multilocus binding. The benefits of multiple TBMs are evident in three specific comparisons shown in Table 2. In the table, compounds of the invention comprise at least two IEMs and at least two TBMs. Compounds of the invention are compared to compounds that have only a single IEM or a single TBM. The comparison demonstrates the increased relaxivity per IEM for the compounds of the invention. For the measurements in this table, the target is Human Serum Albumin (HSA). First, the comparison of the M8-04 and M8-05 molecules demonstrates that increasing the number of IEMs while the number of TBMs remains constant results in a corresponding increase in total relaxivity. Specifically, this comparison demonstrates that IEMs can be added without a commensurate loss in relaxivity per Gd(III) ion provided that at least two TBMs are present and adequately spaced in the molecule.

Both the M8-04 and M8-05 compounds contain two TBMs, each of which contains a benzofused cyclopentyl group, a phenyl group, and an alkyl substituted phenyl group. These two TBMs are apparently sufficient to tether the molecule so that when the number of IEMs (in this case DTPA moieties) is increased from two to four, the relaxivity per Gd(III) at each IEM site remains the same (32 versus 32.7 mM$^{-1}$s$^{-1}$ at 20 MHz). Consequently, the total relaxivity for the molecule doubles in concert with the doubling of the number of IEMs (64 mM$^{-1}$s$^{-1}$ for two IEMs versus 131 mM$^{-1}$s$^{-1}$ for four IEMs).

TABLE 2

The relaxivity increase through multilocus binding: Single TBM vs. Two TBMs

| Compound # | # of TBMs | # of IEMs |
| --- | --- | --- |
| M8-04 | 2 | 2 |
| M8-05 | 2 | 4 |
| M8-06 | 1 | 4 |
| M8-07 | 1 | 4 |
| M8-08 | 2 | 4 |
| M8-09 | 1 | 1 |
| M8-10 | 1 | 3 |

Compound #  Chemical Structure

M8-04

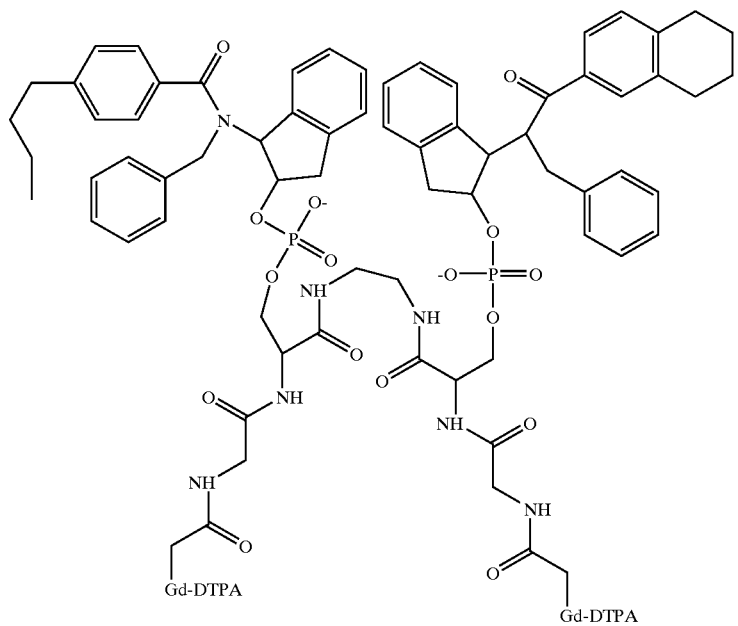

TABLE 2-continued
The relaxivity increase through multilocus binding: Single TBM vs. Two TBMs
M8-05
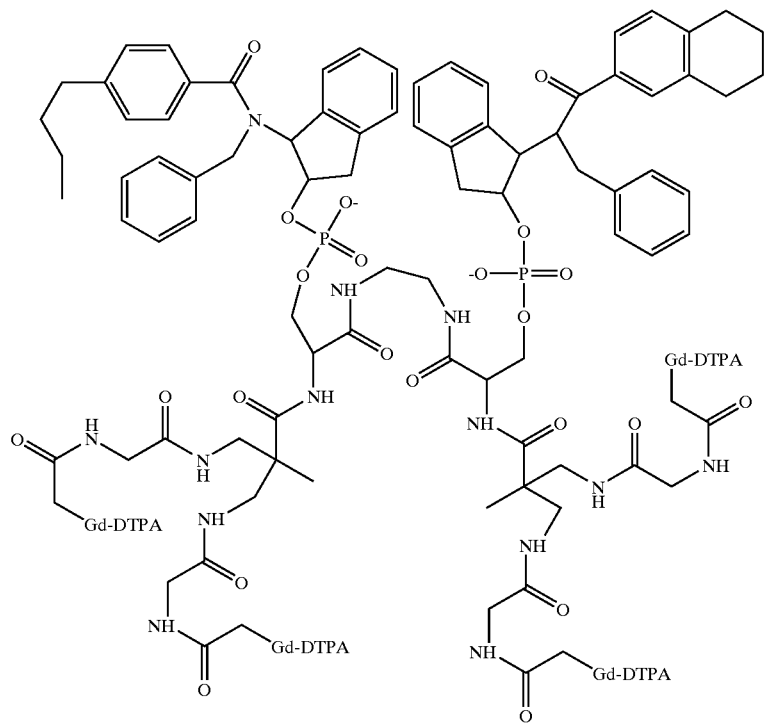
M8-06
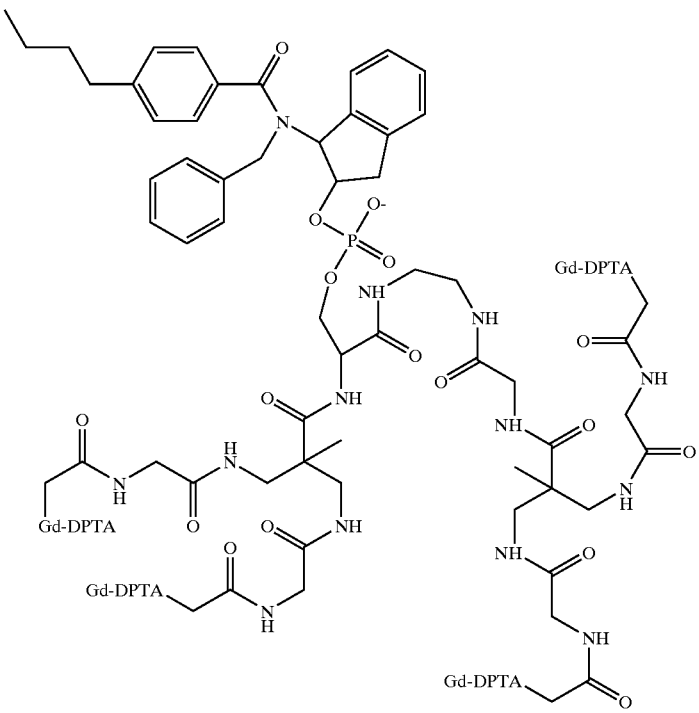

TABLE 2-continued
The relaxivity increase through multilocus binding: Single TBM vs. Two TBMs
M8-07
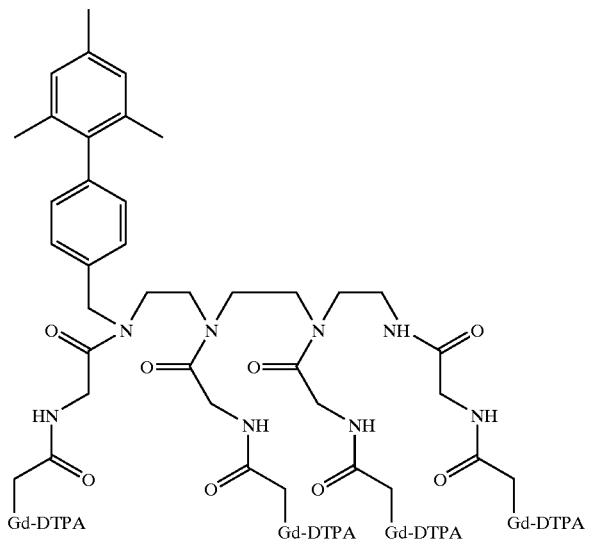
M8-08
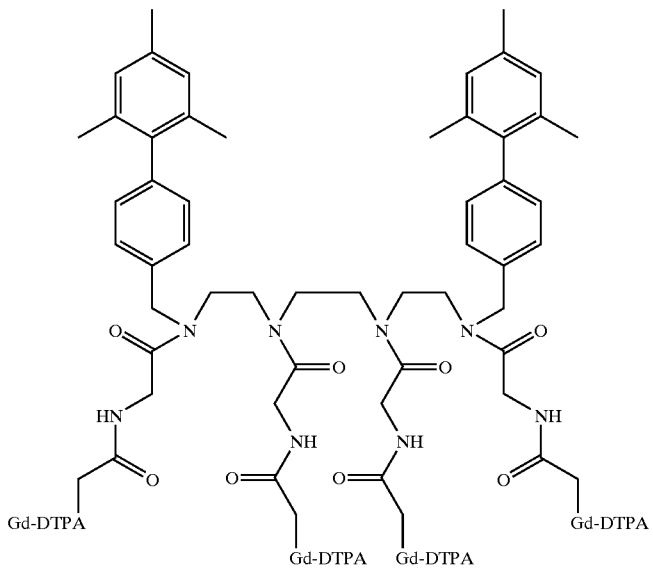
M8-09
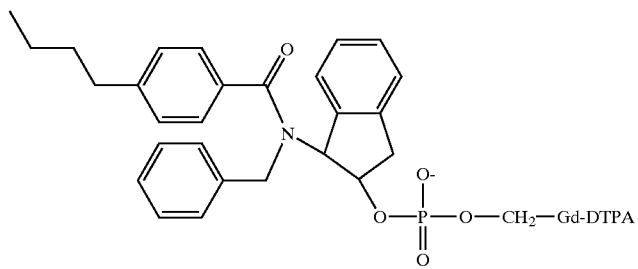

TABLE 2-continued

The relaxivity increase through multilocus binding: Single TBM vs. Two TBMs

M8-10

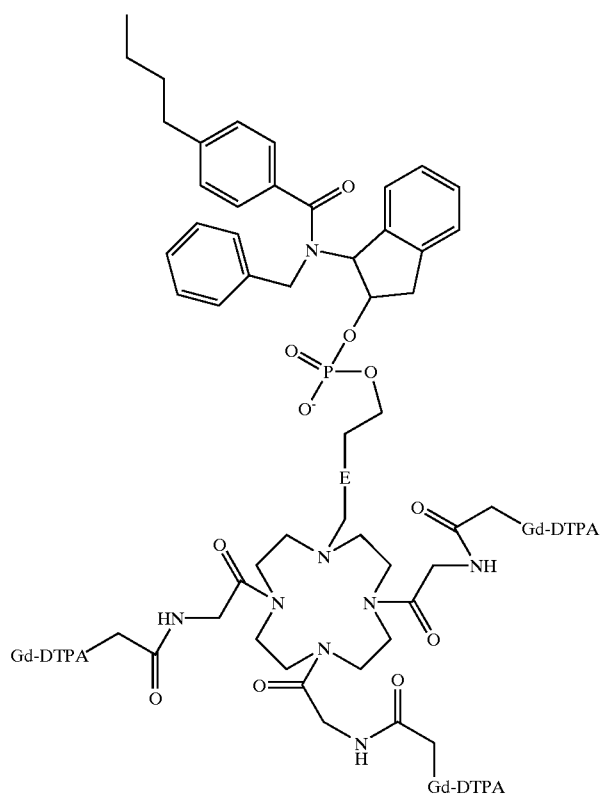

| Compound # | % Bound | $R1_{bound}/Gd^{+3}$ $mM^{-1}s^{-1}$ (20 MHz) | Total R1bound $mM^{-1}s^{-1}$ (20 MHz) |
|---|---|---|---|
| M8-04 | 99 | 32 | 64 |
| M8-05 | 97 | 32.7 | 131 |
| M8-06 | 91.3 | 27 | 108 |
| M8-07 | 64.1 | 16 | 64 |
| M8-08 | 93.7 | 44.1 | 176.5 |
| M8-09 | 99.5 | 38.7 | 38.7 |
| M8-10 | 66.1 | 25.7 | 77.1 |

Second, the comparison of the M8-06 and M8-05 molecules demonstrates that increasing the number of TBMs while keeping the number of IEMs constant results in an increase in relaxivity per IEM, providing that the TBMs are adequately spaced. In both molecules, the TBMs have the same structure and the IEM structure is the same gadolinium-chelated DTPA moiety. The M8-06 compound, however, contains only a single TBM while the M8-05 compound contains two TBMs. The two TBMs in the M8-05 compound more effectively tether the molecule because the relaxivity per gadolinium increases from 27.0 $mM^{-1}s^{-1}$ to 32.7 $mM^{-1}s^{-1}$ at 20 MHz. Thus, increasing the number of TBMs increases the relaxivity per IEM providing that the TBMs are adequately spaced.

Third, comparison of the M8-07 and the M8-08 molecules (see Table 2) again demonstrates that increasing the number of adequately spaced TBMs while keeping the number of IEMs constant results in an increase in relaxivity per IEM. In both molecules, the TBMs have the same alkyl substituted biphenyl structure, and both compounds have the same number of IEMs, and the IEM structure is the same gadolinium-DTPA moiety. The core structures (scaffolds) are also the same tetraamines for both the M8-07 and M8-08 molecules. The M8-07 compound contains a single TBM and four IEMs while the M8-08 compound contains two TBMs and four IEMs. Again, the two TBMs in the M8-08 compound more effectively tether the molecule because the bound relaxivity per gadolinium increases from 16.0 $mM^{-1}s^{-1}$ to 44.1 $mM^{-1}s^{-1}$ at 20 MHz in the presence of HSA. Consequently, the calculation reveals that the total relaxivity for the molecule more than doubles in concert with the doubling of the number of TBMs (a 2.75-fold increase from 64.0 $mM^{-1}s^{-1}$ for one TBM to 176.5 $mM^{-1}s^{-1}$ for two TBMs). On the other hand, the free relaxivities for the compounds M8-07 and M8-08 are comparable, namely 9.2 and 10.3 $mM^{-1}s^{-1}$ at 20 MHz, respectively. The ratios of $R1_{bound}$ to $R1_{free}$ for the compound M8-07 and M8-08 are 1.7 and 4.3, respectively, which indicates that the M8-08 compound will provide better contrast enhancement between target and background. Since the compound M8-08 also has increased HSA affinity and therefore greater target specificity compared to the M8-07, the contrast enhancement from this multilocus binding multimer should be even more superior to the multimer with one TBM.

Finally, the table also includes data for compounds M8-09 and M8-10. These data are included to provide typical relaxivities for molecules that contain a single TBM and multiple IEMs. Comparison of the M8-09 and M8-10 molecules also demonstrates that simple addition of IEMs to a molecule with a certain TBM does not result in a proportionate increase in total relaxivity since a three-fold increase in the number of IEMs only results in a two-fold increase in relativity.

Thus, tethering the molecule at two separate sites serves to increase the relaxivity (i.e., decrease the rotational correlation time) for both the molecule as a whole and for the local chelation regions within the contrast agent. The TBMs should be separated by a sufficient distance, however, so that they effectively decrease the flexibility of the entire molecule when the molecule binds to the target. This results in values for the average $RI_{bound}$ per IEM that do not substantially decrease upon the addition of up to four IEMs. The multilocus binding surprisingly limits flexibility throughout the entire multimeric chelate structure. Thus, for IEMs that include chelates, local chelate motion is reduced following multilocus binding. As a result, remarkably enhanced MRI signals are observed compared to the enhancement for analogous multimeric chelate compounds that bind through only a single TBM and thus are not "pseudo-cyclized" or "zippered" to the targeted site. Contrast enhancement is further increased with these multimeric/multilocus binding structures since they also produce a signal in the unbound state that is less than contrast agents that have rigid molecular structures and they have improved binding affinity for the target. In short, the presently described invention provides compounds, compositions, and their methods of use wherein the relaxivity per IEM does not decrease upon the addition of IEMs as a result of multilocus binding interactions (multiple TBMs), and consequently improves contrast.

USES

Blood pool imaging has many potential diagnostic and therapeutic benefits. Detailed images of the circulatory system can provide information that will allow early detection of, for example, aneurisms, embolisms or thromboses and other clots, and areas of restricted blood flow such as those that exist in the coronary arteries in arteriosclerosis. Other common circulatory diseases that may be more accurately diagnosed with high resolution blood pool imaging are circulatory deficiencies associated with diabetes, heart diseases, lymphedema, peripheral vascular disease, Raynaud's Phenomenon, phlebitis and other injuries to the blood vessel lining, heart murmurs, varicose veins and other diseases that result from valve disorders, and vasculitis. Also, contrast agents directed against specific targets could improve the diagnosis of diseases such as neutropenia which results from a neutrophil deficiency. In addition, MR, optical, and other forms of imaging are less invasive than current techniques that require surgical incisions and catheter insertion under general anesthesia.

MRI and optical contrast agents prepared according to the disclosures herein may be used in the same manner as conventional MRI and optical contrast agents. When imaging a thrombus, certain MR techniques and pulse sequences may be preferred to enhance the contrast of the thrombus compared to the background blood and tissues. These techniques include, but are not limited to, black blood angiography sequences that seek to make blood dark, such as fast spin echo sequences and flow-spoiled gradient echo sequences. These methods also include flow independent techniques that enhance the difference in contrast due to the $T_1$ difference between contrast-enhanced thrombus and blood and tissue, such as inversion-recovery prepared or saturation-recovery prepared sequences that will increase the contrast between thrombus and background tissues. Methods of preparation for $T_2$ techniques may also prove useful. Finally, preparations for magnetization transfer techniques may also improve contrast with agents of the invention.

The compositions may be formulated in accordance with routine procedures as a pharmaceutical composition adapted for intravenous administration to human beings or in animal model systems. Typically, compositions for intravenous administration are solutions in sterile isotonic aqueous buffer. Where necessary, the composition may also include a solubilizing agent and a local anaesthetic such as lignocaine to ease pain at the site of the injection. Generally, the ingredients will be supplied either separately or mixed together in unit dosage form, for example, as a dry lyophilized powder or water free concentrate. The composition may be stored in a hermetically sealed container such as an ampule or sachette indicating the quantity of active agent in activity units. Where the composition is administered by infusion, it can be dispensed with an infusion bottle containing sterile pharmaceutical grade "water for injection" or saline. Where the composition is to be administered by injection, an ampule of sterile water for injection or saline may be provided so that the ingredients may be mixed prior to administration.

Pharmaceutical compositions of this invention comprise the compounds of the present invention and pharmaceutically acceptable salts thereof, with any pharmaceutically acceptable ingredient, excipient, carrier, adjuvant or vehicle.

The high relaxivity multilocus contrast agent is preferably administered to the patient in the form of an injectable composition. The method of administering the MRI contrast agent is preferably parenterally, meaning intravenously, intraarterially, intrathecally, interstitially or intracavitarilly. Pharmaceutical compositions of this invention can be administered to mammals including humans in a manner similar to other diagnostic or therapeutic agents. The dosage to be administered, and the mode of administration will depend on a variety of factors including age, weight, sex, condition of the patient and genetic factors, and will ultimately be decided by medical personnel subsequent to experimental determinations of varying dosage followed by imaging as described herein. In general, dosage required for diagnostic sensitivity or therapeutic efficacy will range from about 0.001 to 50,000 $\mu$g/kg, preferably between 0.01 to 25.0 $\mu$g/kg of host body mass. The optimal dose will be determined empirically following the disclosure herein.

Synthesis and use of several high relaxivity multilocus compositions in one embodiment of the invention will be further illustrated in the following examples. The specific parameters included in the following examples are intended to illustrate the practice of the invention, and they do not in any way limit the scope of the invention. Although a number of embodiments and features have been described above, it will be understood by those skilled in the art that modifications and variations of the described embodiments and features may be made without departing from either the spirit of the invention or the scope of the appended claims. Although a number of embodiments and features have been described above, it will be understood by those skilled in the art that modifications and variations of the described embodiments and features may be made without departing from either the spirit of the invention or the scope of the appended claims.

EXAMPLES

Example 1
Method for Determining Relaxivity

The compounds of the present invention were evaluated for relaxivity using a Bruker NMS-120 Minispec NMR spectrometer operating at 0.47 Tesla (20 MHz H-1 Larmor frequency) and 37° C. $T_1$ of water protons was determined by an inversion recovery pulse sequence using the instrument's software. Relaxivity was determined in the presence of the target (typically 4.5% HSA) by preparing 4 individual samples. The first contained only 4.5% HSA in phosphate buffered saline (PBS), and the other three contained ca. 20, 30, and 40 µM Gd(III), respectively, in addition to 4.5% HSA in PBS. The samples are incubated at 37 degrees C. for at least 15 minutes to ensure temperature equilibration before the $T_1$ measurement is performed. The Gd(III) content of the samples is determined by inductively coupled plasma—mass spectrometry (ICP-MS). The relaxivity (per Gd(III) ion) is determined by plotting the relaxation rate $(1/T_1)$ in $s^{-1}$ versus the Gd(III) concentration in mM. The slope of a linear fit to the data gives the relaxivity. The relaxivity of the compounds in the absence of target is also determined in an analogous manner, except there is no target present.

The concentration of species bound to the target under these conditions is determined in a separate experiment using e.g. ultrafiltration or equilibrium dialysis. Knowledge of the amount of species bound to the target, the relaxivity in the presence of the target, and the relaxivity in the absence of the target allows the calculation of the average bound relaxivity as described herein.

Example 2
Experimental Model for Testing Fibrin Binding Contrast Agents of the Present Invention A contrast agent with high relaxivity and specificity for clot (thrombus) imaging as described in these examples can distinguish between fibrin in a clot and circulating fibrinogen. It can provide a sensitive, effective detection of thromboses at various stages of development. It can be used to diagnose the presence or absence of early and late thrombi.

One animal model that may be used is the rabbit jugular vein clot model in which the jugular vein is clamped. The vein is clamped at two locations, and the rabbit blood between the clamps is removed. Human fibrinogen, rabbit red blood cells and thrombin are added to the vein between the clamps to generate a clot containing human fibrin. The clot is typically aged for 30 minutes.

In the rabbit jugular model, a typical machine is a 1.5 Tesla using a spoiled gradient (SPGR) MRI at 36/5/30 deg). Alternatively, a 3D GRE 44/10/30 deg. method of imaging may be used with a 1.5 Tesla machine. Alternatively, IR 2000/10/700 methods may be employed with a 1.5 Tesla.

Example 3
Example Compound: Synthesis

Figure 12:
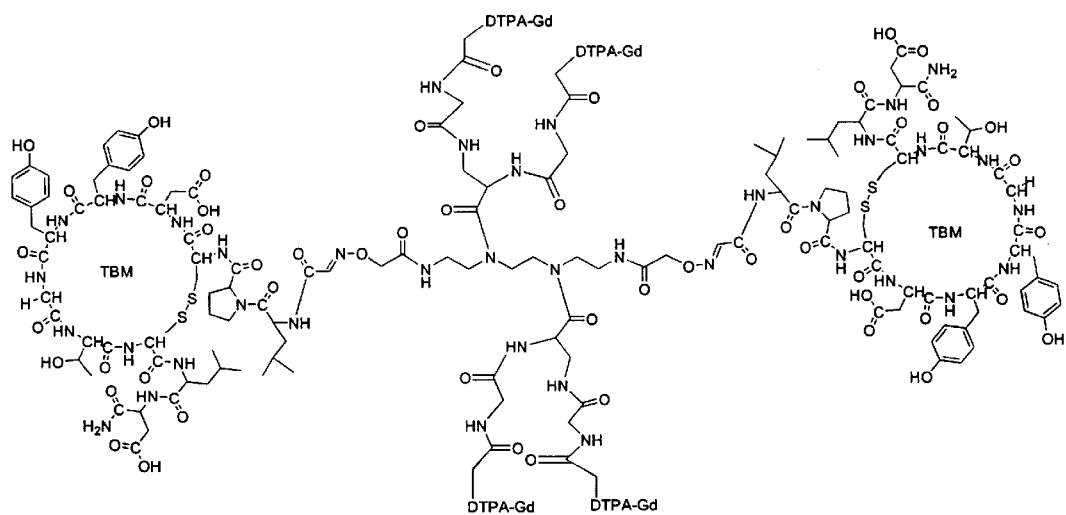

A preferred embodiment of the invention is a contrast agent for MRI imaging having a chemical structure shown in FIG. 12 and named "M8-11". The contrast agent in FIG. 12 comprises four DTPA-Gd molecules that serve as the IEMs. The IEMs are attached to an ethylene diamine scaffold through linkers that comprise a series of repeating amides. The TBMs are two peptides that exhibit high affinity for fibrin. The peptides may cyclize through formation of a disulfide bond between two cysteine residues. The TBMs are attached to the scaffold through an oxime and amide linkage.

Figure 13:
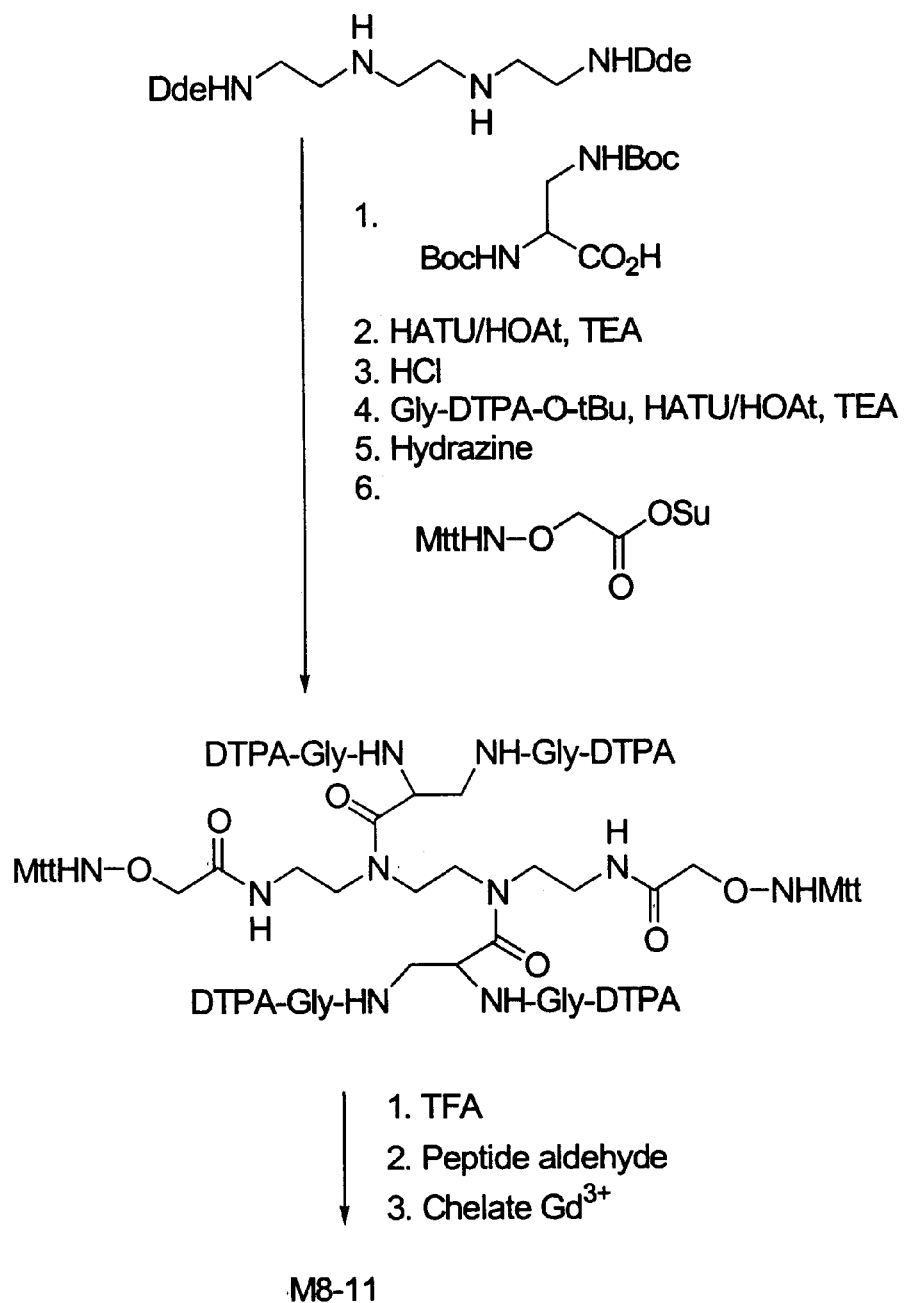
FIG. 13. Synthesis of a multimer contrast agent targeted to human fibrin

Binding of the prototype thrombus agent to the DD(E) amino acid fragment of fibrin is 51% bound at 37° C., 10 µM contrast agent, 2.5 mg/mL fibrin, 50 mM Tris, 150 mM NaCl, 2 mM $Ca^{2+}$, pH 7.4. Relaxivity for the bound compound is 101.4 $mM^{-1}s^{-1}$ measured at 20 MHz and 37° C. which is 25.4 $mM^{-1}s^{-1}$ per Gd chelate. The free contrast agent has a relaxivity of 67.7 $mM^{-1}s^{-1}$ which is 16.9 $mM^{-1}s^{-1}$ per Gd chelate. The relaxivity of the agent increases greatly upon binding. The synthesis of a thrombus peptide multimer as a prototype MR contrast agent that is targeted to human fibrin is described in FIG. 13. Although a particular peptide and contrast agent are shown (M8-11), one of skill will appreciate that other peptides may be substituted in the compound and that the peptides used in the compound need not be the same.

Experimental Section
Synthesis of DiDde-tetraamine

Tetraamine (Fluka) (1.50 mL) was reacted with Dde-OH (NovaBiochem) (4.0 g) in 30 mL EtOH. The clear pale yellow solution was refluxed for 16 h. After the completion of the reaction, the reaction mixture was concentrated in vacuo to a dry residue. The residue was dissolved in 250 mL ether and 2 N HCL solution. The pale yellow acidic aqueous layer was separated and a 50% NaOH solution was until to a pH of 12 was reached and then back extracted with EtOAc. The EtOAc layers were washed with brine, dried ($Na_2SO_4$), and filtered. The filtrate was evaporated in vacuo to yield a pale yellow lumpy solid (2.9 g) which was purified on a Flash silica column using EtOAc/MeOH (2:3)and EtOAc/ (MeOH with 1% $NH_4OH$)(2:3) to yield pure pale yellow solid as the desired product (2.3 g). $^1$H-NMR(300 MHz, $CDCl_3$): δ1.02(s,6H,), 2.34(s,4H,2), 2.56(s,), 2.79(s,2H), 2.92–2.94(t,2H), 3.48–3.54(q,2H). MS: m/z 475.2 $(M+H)^+$ Synthesis of DiDde-tetraamine di-Dpr(Boc)$_2$ Boc-Dpr(Boc)-OH.DCHA (4.85 g) was suspended in 60 mL EtOAc along with 12.0 mL of 2M $H_2SO_4$. The flask was shaken and the EtOAc layer was separated. The aqueous layer was back extracted with EtOAc. The EtOAc layers were combined, washed with brine, dried over anhydrous $MgSO_4$, and filtered. The filtrate was evaporated in vacuo and the solid obtained was dried to yield 3.23 g of the desired Boc-Dpr(Boc)-OH free acid, as white crystalline solid. $^1$H-NMR(300 MHz, DMSO-d$_6$): δ1.35 (s,18H,), 3.30 (s,2H), 3.96–3.98 (m,1H), 6.87–6.90 (d,1H).

Boc-Dpr(Boc)-OH as free acid (1.52 g) was dissolved in 15 mL DCM at 0° C. To it was added HOAt (0.68 g) and DIEA (0.35 mL) and the clear solution was allowed to stir at 0° C. The DiDde-tetraamine from above was then added to the solution, followed by the addition of HATU (1.90 g)and 2 mmol of TEA. Anhydrous DMF (5 ml) was added and the reaction was stirred for 36 h. The solvents were evaporated in vacuo and the residue was taken up in 150 mL EtOAc and washed with 1 N HCl, saturated $NaHCO_3$, brine, then dried over anhydrous $Na_2SO_4$, filtered and evaporated in vacuo to give a white solid (1.92 g). This solid was purified on Flash silica column chromatography using EtOAc (5% MeOH) to give the desired product as a white solid (1.3 g). $^1$H-NMR (300 MHz, $CDCl_3$): δ1.01(s,6H),1.35 (s,18H,), 2.34 (s,4H,),2.58 (s,3H), 3.30(s,2H),3.44–3.67 (bm,6H), 3.85–4.10 (m,1H),5.44–5.52 (d,2H),5.74(bs,1H). MS: m/z 1047.7 $(M+H)^+$ Synthesis of Di-Dde-tetraamine-diDpr.HCl salt DiDde-tetraamine-diDpr (BOC)$_2$ was dissolved in 40 mL 4 N HCl/Dioxane and stirred for 10 h. The suspension was triturated with cold ether and evaporated in vacuo to obtain copious amounts of white solid. The solid was dried under high-vac pump to yield the desired product in HCl salt form (1.09 g). MS: m/z 647.3$(M+H)^+$ Synthesis of DiDde-diDpr-tetra-GlyDTPA-OtBu Gly-DTPA penta-t-Butylester (Gly-DTPA-O-tBu)(2.37 g) was taken up in 10 mL DMF at 0° C. HOAt (0.41 g) and DIEA (0.52 mL) were added and the solution was stirred at 0° C. The Di-Dde-tetraamine-diDpr salt from above (0.39 g) was dissolved in 3 mL DMF and DIEA (0.13 mL) was added. HATU (1.14 g) was added to the mixture along with the additional DIEA (0.09 mL). The yellow-colored solution was stirred 36 h. The solvents were removed in vacuo and the residue taken up in EtOAc. The organic layer was washed with 1 N HCl, saturated $NaHCO_3$, brine, dried over anhydrous $Na_2SO_4$, filtered and evaporated in vacuo to give a pale yellow colored solid (3.15 g). The crude product was further purified on the Prep RP-HPLC [C-4, ACN/$H_2O$]. The fractions containing the desired compound were pooled and lyophilized to give a white solid (1.01 g). MS: m/z 1244.4 $(M+3H)^{3+}$; 933.9$(M+4H)^{4+}$ Synthesis of Tetraamine-tetra-CN-GlyDTPA-O-tBu DiDde-tetraamine-diDpr-tetra-GlyDTPA-O-tBu (0.38 g) was dissolved in 8 mL 2% v/v hydrazine in DMF and stirred for 10 min at room temp. The reaction mixture was concentrated in vacuo and the residue taken up in $CH_3CN$ and purified on Prep-RP-HPLC [C-4,ACN/$H_2O$]. The fractions containing the desired compound were pooled and lyophilized to give a white solid (0.25 g). MS: m/z 1702.1$(M+2H)^{2+}$; 1135.1$(M+3H)^{3+}$ Synthesis of Di-MeO-trityl-AoA-tetra-Gly-DTPA-O-tBu Tetraamine-tetra-Gly-DPTA-O-tBu (98 mg) was dissolved in 3 mL DMF at 0° C. Methoxytritylaminooxyacetic acid succinimide ester (MeO-Trt-AoA-OSu) (29 mg) was added along with TEA (9 μL) and stirred overnight, MeOH was added, the solvents were evaporated, and the residue extracted with DCM, washed with 10% aq. citric acid, brine and dried over anhydrous $MgSO_4$. The product was further purified on a Prep RP-HPLC [C-4,ACN/$H_2O$]. The fractions having the desired product, were pooled and lyophilized to give a white solid (87 mg). MS: m/z 2047.5$(M+2H)^{2+}$; 1365.3 $(M+3H)^{3+}$ Synthesis of AoA-tetra-GlyDTPA-OH Di-MeOtrityl-AoA-tetra-GlyDTPA-O-tBu (85 mg) was dissolved in 10 mL $CH_3Cl$/thioanisole/DCM/TIS (64/16/16/4) and stirred at 0° C. for 3 h. TIS is $(iPr)_3SiH$. The reaction mixture was diluted with 20 mL water and extracted with ether. The aqueous layer was further purified on a Prep RP-HPLC [C-18,ACN/$NH_4OAc$]. The product was isolated and was lyophilized to a white solid (29 mg). MS: m/z 1214.4 $(M+2H)^{2+}$; 809.5 $(M+3H)^{3+}$ Oxidation of SLPCDYYGTCLD-$NH_2$ The peptide, c[SLPCDYYGTCLD-$NH_2$], 10 mM in NaPi buffer, pH=6.8) was reacted with $NaIO_4$ (20 mM). The oxidation was quenched with ethylene glycol. The reaction purified on a C-18 Sep-Pak cartridge. The product was eluted with 80% $CH_3CN$ containing 0.1% TFA. The solvents were removed in vacuum centrifuge and the desired product alpha-N-glyoxylyl-c[LPCDYYGTCLD-$NH_2$] was lyophilized to a white powder. MS: m/z 1315.5 $(M+H)^+$ Chemoselective Ligation-Final assembly: Synthesis of M8-11

Alpha-N-glyoxylyl-c[LPCDYYGTCLD-$NH_2$] (13.2 mg) and AoA-tetraDPTA-OH (12.3 mg) were reacted in 20 mM sodium acetate buffer, pH4.6 at 22° C. The reaction was purified on a Semi-Prep RP-HPLC [C-18, $CH_3CN$/5 mm $NH_4OAc$]. This material was converted to the gadolinium complex according to standard techniques [see for example, Lauffer R. B., et al. *Radiology* 207: pp. 529–38 (1998)]. MS: m/z 1674.6 $(M+3H)^{3+}$; 1256.3 $(m+4H)^{4+}$.

Example 4

Synthesis of Contrast Agents with a Triethylenetetramine Scaffold

Using Di-Dde-tetramine-diDpr and procedures described above along with substitutions for the diamino-BOC substituted ethane linker and the Gly-DTPA-OtBu IEM, various chelates as described above may be attached to the triethylenetetramine scaffold. The chelates may be the same or different to produce a homogenous chelate contrast agent or a contrast agent with heterogenous chelates.

Example 5

Synthesis of M8-07

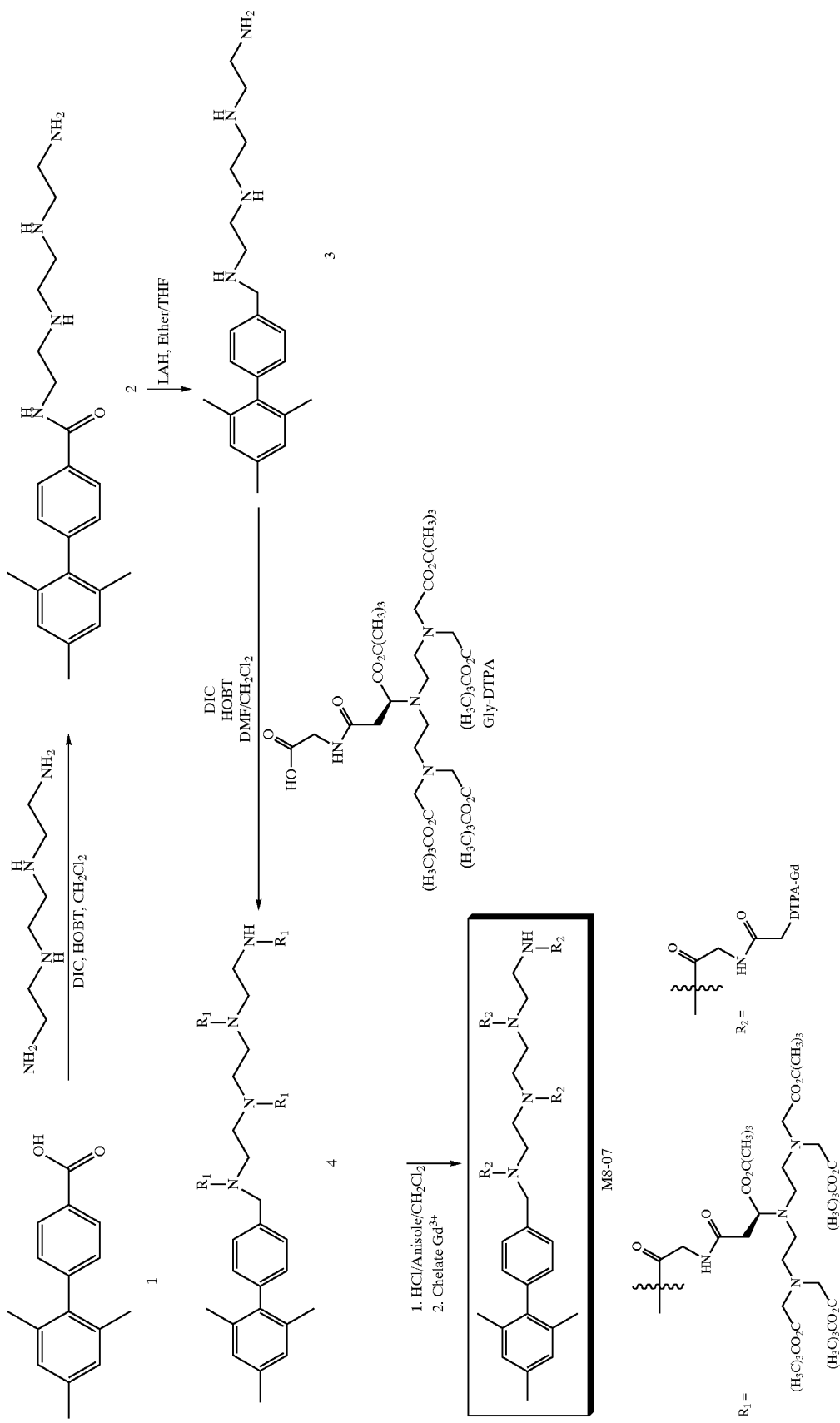

To a solution of 4-Mesitylbenzoic acid (0.7 g) and triethylenetetramine (4.26 g) in $CH_2Cl_2$ (200 mL) were added HOBt (0.89 g, 5.83 mmol) and DIC (0.74 g). The mixture was stirred at room temperature overnight. The resultant precipitate was filtered and the solvent was removed under reduced pressure to give a yellow oil. The reaction mixture was submitted to Prep-HPLC on C4 column (eluant: 0.1% $TFA/H_2O/CH_3CN$) to give the TFA salts of the monoamide as a white foam (0.63 g). LC-MS: (m/e) 369.1 ($M^+$).

To a solution of the above monoamide (0.63 g) in ether (100 mL) and THF (100 mL) was added LAH (1.30 g) slowly at room temperature. The mixture was refluxed for 2 h and then stirred at room temperature for overnight. To the mixture was added water dropwise to quench LAH. The resultant precipitate was removed by filtration and the solvent was removed at reduced pressure to give a colorless oil. The reaction mixture was submitted to Prep-HPLC on C4 column (eluant: 0.1% $TFA/H_2O/CH_3CN$) to give a TFA amine salt as a white foam (180 mg). LC-MS: (m/e) 354.4 $(M+H)^+$.

To a solution of the TFA amine salt (180 mg) and diisopropylethylamine (287 mg) in DMF (50 mL) were added a solution of Gly-DTPA-OtBu (1.88 g) in $CH_2Cl_2$ (50 mL), HOBt (370 mg) and DIC (301 mg). The mixture was stirred at room temperature for overnight. The solvent was removed at reduced pressure to give a yellow oil. The reaction mixture was submitted to Prep-HPLC on C4 column (eluant: 0.1% $TFA/H_2O/CH_3CN$) to give a crude product as a white solid (0.36 g). LC-MS: (m/e) 1719.4 $(M+2H)^{2+}$, 1147.2 $(M+3H)^{3+}$.

To a solution of this white solid (0.19 g) in $CH_2Cl_2$ (4.5 mL) and anisole (4.5 mL) was added dropwise 4.5 mL of 12 N HCl. The mixture was stirred at room temperature for 3 h. To the mixture was added 40 mL of water and washed three times with ether. The aqueous solution was lyophilized to give the crude product which was submitted to Prep-HPLC on C18 column (eluant: 100 mM $NH_4OAc/CH_3CN$) to give a white solid (50 mg). LC-MS: (m/e)1158.6 $(M+2H)^{2+}$, 772.8 $(M+3H)^{3+}$.

This material was converted to the gadolinium complex according to standard techniques [see for example, Lauffer R. B., et al. *Radiology* 207: pp. 529–38 (1998)].

Example 6

Synthesis of M8-08

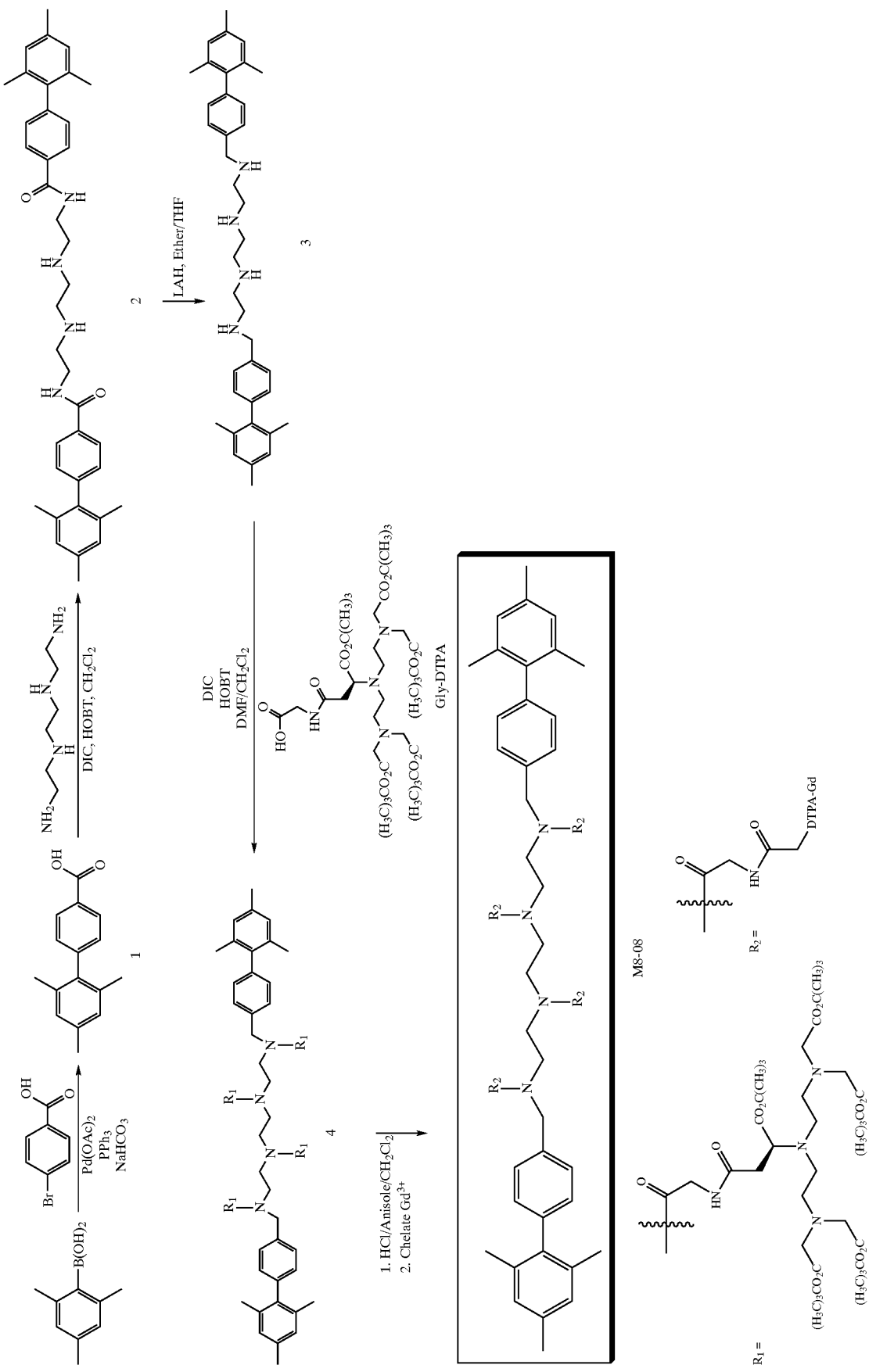

4-Mesitylbenzoic Acid

To a solution of mesitylboronic acid (10 9) and 4-bromobenzoic acid (12.9 g) in 1-propanol (150 mL) and DME (200 mL) were added triphenylphosphine (0.128 g), 2M sodium carbonate solution (37 mL) and water (30 mL). To the mixture was added palladium acetate (82 mg) under nitrogen atmosphere. The mixture was heated to reflux overnight. After the heat source was removed, 100 mL of water was added and stirred for 2.5 h while cooling to room temperature. The darkened mixture was diluted with 150 mL of ethyl acetate and the two phases were separated. The organic layer was washed several times with saturated sodium bicarbonate solution until TLC indicated that 4-bromobenzoic acid ($R_f$=0.55, eluant: $CH_2Cl_2/CH_3OH$=5) was completely removed. The solution was extracted three times with 200 mL of 1N NaOH solution. To the combined aqueous layers was added about 50 mL of 12 N HCl to pH 3. The resultant precipitate were filtered, washed with water, and dried to give 4-Mesitylbenzoic acid as a white solid (8.81g). $R_f$=0.75 (eluant: $CH_2Cl_2/CH_3OH$=5) $^1$H-NMR (300 MHz, $CDCl_3$): δ1.997 (s,6 H), 2.340 (s,3 H), 6.961 (s,2 H), 7.274 (d,J=8.1 Hz,2 H), 8.177 (d,J=8.1Hz,2 H).

To a solution of 4-Mesitylbenzoic acid (1.5 g) and triethylenetetramine (0.43 g) in $CH_2Cl_2$ (60 mL) were added HOBt (0.96 g) and DIC (0.79 g). The mixture was stirred at room temperature overnight. The resultant precipitate was filtered and dried to give a white solid (1.45 g). LC-MS: (m/e) 591.3 $(M+H)^+$.

To solution of the white solid (0.45 g) in ether (20 mL) and THF (80 mL) was added LAH (0.33 9) slowly at room temperature. The mixture was refluxed for 2 h and then stirred at room temperature overnight. To the mixture water was added dropwise to quench LAH. The resultant precipitate was removed by filtration, and the solvent was removed at reduced pressure to give a pale yellow oil. The reaction mixture was submitted to Prep-HPLC on C4 column (eluant: 0.1% $TFA/H_2O/CH_3CN$) to give the TFA salt as a white solid (140 mg). LC-MS: (m/e) 564.6 $(M+H)^+$.

To a solution of the TFA salt (50 mg) and diisopropylethylamine (38 mg) in DMF (30 mL) were added a solution of Gly-DTPA-OtBu (193 mg) in $CH_2Cl_2$ (30 mL), HOBt (37.5 mg) and DIC (31 mg). The mixture was stirred at room temperature overnight. The solvent was removed at reduced pressure to give a brown oil. The reaction mixture was submitted to Prep-HPLC on C4 column (eluant: 0.1% TFA/$H_2O/CH_3CN$) to give a crude product as a pale yellow solid. LC-MS: (m/e) 1824.2 $(M+2H)^{2+}$, 1216.3 $(M+3H)^{3+}$, 912.5 $(M+4H)^{4+}$.

To a solution of the pale yellow solid (0.58 g) in $CH_2Cl_2$ (5 mL) and anisole (5 mL) 10 mL of 12 N HCl was added dropwise. The mixture was stirred at room temperature for 3 h. To the mixture 40 mL of water was added, and the resultant mixture was washed three times with ether. The aqueous solution was lyophilized to give a crude product which was submitted to Prep-HPLC on C18 column (eluant: 100 mM $NH_4/OAcCH_3CN$) to give a white solid (11 mg). LC-MS: (m/e)1263.2 $(M+2H)^{2+}$, 842.4 $(M+3H)^{3+}$, 632.2 $(M+4H)^{4+}$.

This material was converted to the gadolinium complex according to standard techniques [see for example, Lauffer R. B., et al. *Radiology* 207: pp. 529–38 (1998)].

Example 7
General Synthesis of HSA Binding Multimers Comprising Two Identical TBMs

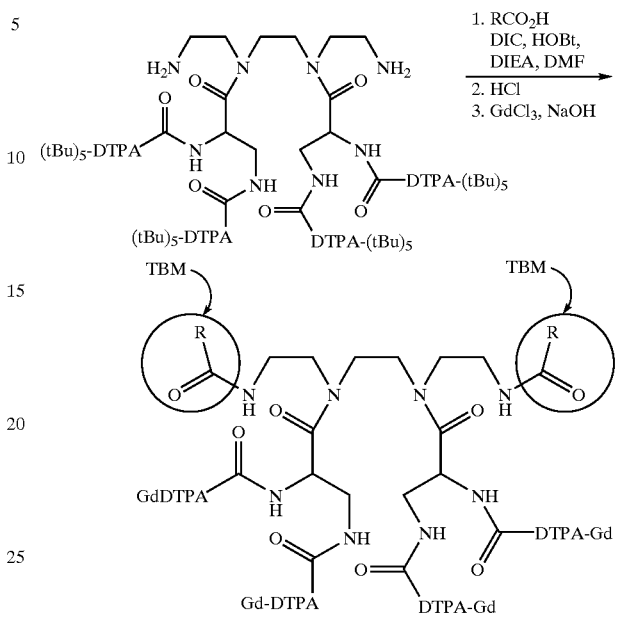

The diamine comprising four t-butyl ester protected DTPAs was dissovled in dimethylformamide (0.75 mL). $RCO_2H$ (3 eq), which represents a variety of carboxylic acids comprising TBMs, DIC (0.052 mL, 3.3 eq) and HOBt (0.051g, 3.3 eq) were added. The reaction mixture was cooled to 0° C. prior to the dropwise addition of DIEA (0.105 mL, 6 eq). The reaction mixture was stirred for a total of 8.5 h at room temperature. The reaction mixture was diluted with $CH_2Cl_2$ and was washed with 0.1N HCl, sat. $NaHCO_3$ and brine. The organic layer was dried over $Na_2SO_4$ and the residual solvent was removed in vacuo to give the t-butylester protected intermediate. The product was taken up in DCM, HCl was added at 0° C., and was stirred for 3 hours. Evaporation of the solvent gave a white solid which was reacted with $GdCl_3$ (4 equiv) and NaOH (12 equiv) to give the final product.

A list of compounds having two identical TBMs that were synthesized according to this method along with the structures of the TBMs and the mass spec data are compiled in Table 3.

TABLE 3

Multilocus Contrast Agents with two identical TBMs

| Compound # | Chemical Structure of TBM "R" in General Synthetic Scheme | Mass Spec (m/z, $[M]^{3+}$) |
|---|---|---|
| M8-12 | ![structure] | 1048.5 |

TABLE 3-continued

Multilocus Contrast Agents with two identical TBMs

| Compound # | Chemical Structure of TBM "R" in General Synthetic Scheme | Mass Spec (m/z, [M]$^{3+}$) |
|---|---|---|
| M8-13 | | 1036.9 |
| M8-14 | | 1080.9 |
| M8-15 | | 1005.0 |
| M8-16 | | 1036.8 |
| M8-17 | | 1094.1 |
| M8-18 | | 1259.1 |
| M8-19 | | 1288.51 |

Example 8
General Synthesis of HSA Binding Multimers Comprising Two Different TBMs

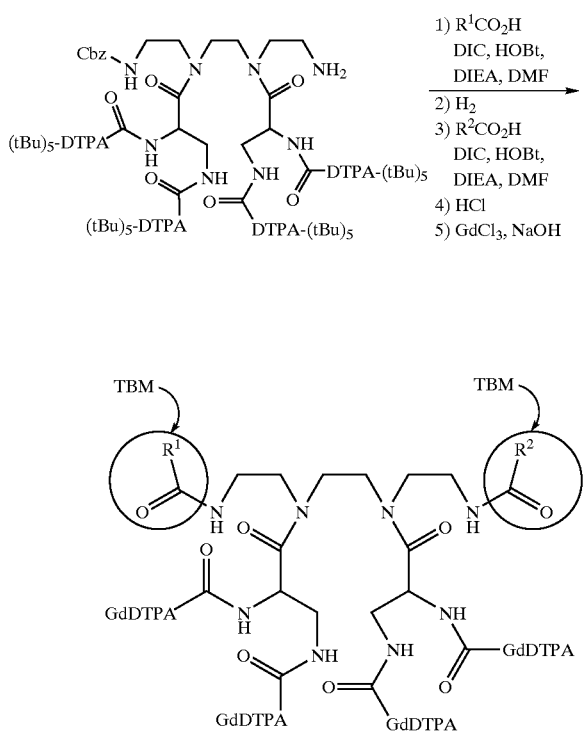

The CBz-protected monoamine comprising four t-butyl ester protected DTPAs was dissovled in dimethylformamide (0.75 mL). $R^1CO_2H$ (1.5 eq), which represents a variety of carboxylic acids comprising TBM1, DIC (0.052mL, 1.5 eq) and HOBt (0.0519, 1.5 eq) were added. The reaction mixture was cooled to 0° C. prior to the dropwise addition of DIEA (0.105 mL, 6 eq). The reaction mixture was stirred for a total of 8.5 h at room temperature.

The reaction mixture was diluted with $CH_2Cl_2$ and washed with 0.1 N HCl, sat. $NaHCO_3$ and brine. The organic layer was dried over $Na_2SO_4$ and the residual solvent removed in vacuo.

The compound was dissolved in EtOAc and hydrogenated (5% Pd-C). Following filtration of the catalyst, the product was reacted with the second carboxylic acid ($R^2CO_2H$, 1.5 equiv), which represents a variety of carboxylic acids comprising TBM2, DIC (0.052 mL, 1.5 eq) and HOBt (0.051 g, 1.5 eq). The reaction mixture was stirred for a total of 8.5 h at room temperature. The reaction mixture was diluted with $CH_2Cl_2$ and washed with 0.1 N HCl, sat. $NaHCO_3$ and brine. The organic layer was dried over $Na_2SO_4$ and the residual solvent is removed in vacuo. The product was resuspended in DCM, HCl was added at 0° C., and the reaction was stirred for 3 hours. Evaporation of the solvent gave a white solid which was reacted with $GdCl_3$ (4 equiv) and NaOH (12 equivalents) to give the final product.

A list of compounds synthesized according to this method along with the structures of TBM1 and TBM2 are compiled in Table 4. Note that "$R^1$" in the general synthetic scheme corresponds to TBM1 and "$R^2$" in the general synthetic scheme corresponds to TBM2.

TABLE 4

Multilocus Contrast Agents with two different TBMs

| Compound # | Chemical Structure of TBM1 "$R^1$" in General Synthetic Scheme | Chemical Structure of TBM2 "$R^2$" in General Synthetic Scheme |
|---|---|---|
| M8-20 | 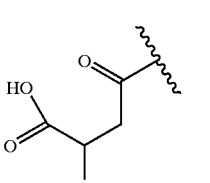 | 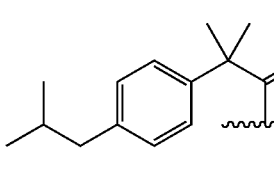 |

TABLE 4-continued

Multilocus Contrast Agents with two different TBMs

| Compound # | Chemical Structure of TBM1 "R¹" in General Synthetic Scheme | Chemical Structure of TBM2 "R²" in General Synthetic Scheme |
|---|---|---|
| M8-21 | | |
| M8-22 | | |
| M8-23 | | |

Example 9
Synthesis of M8-01
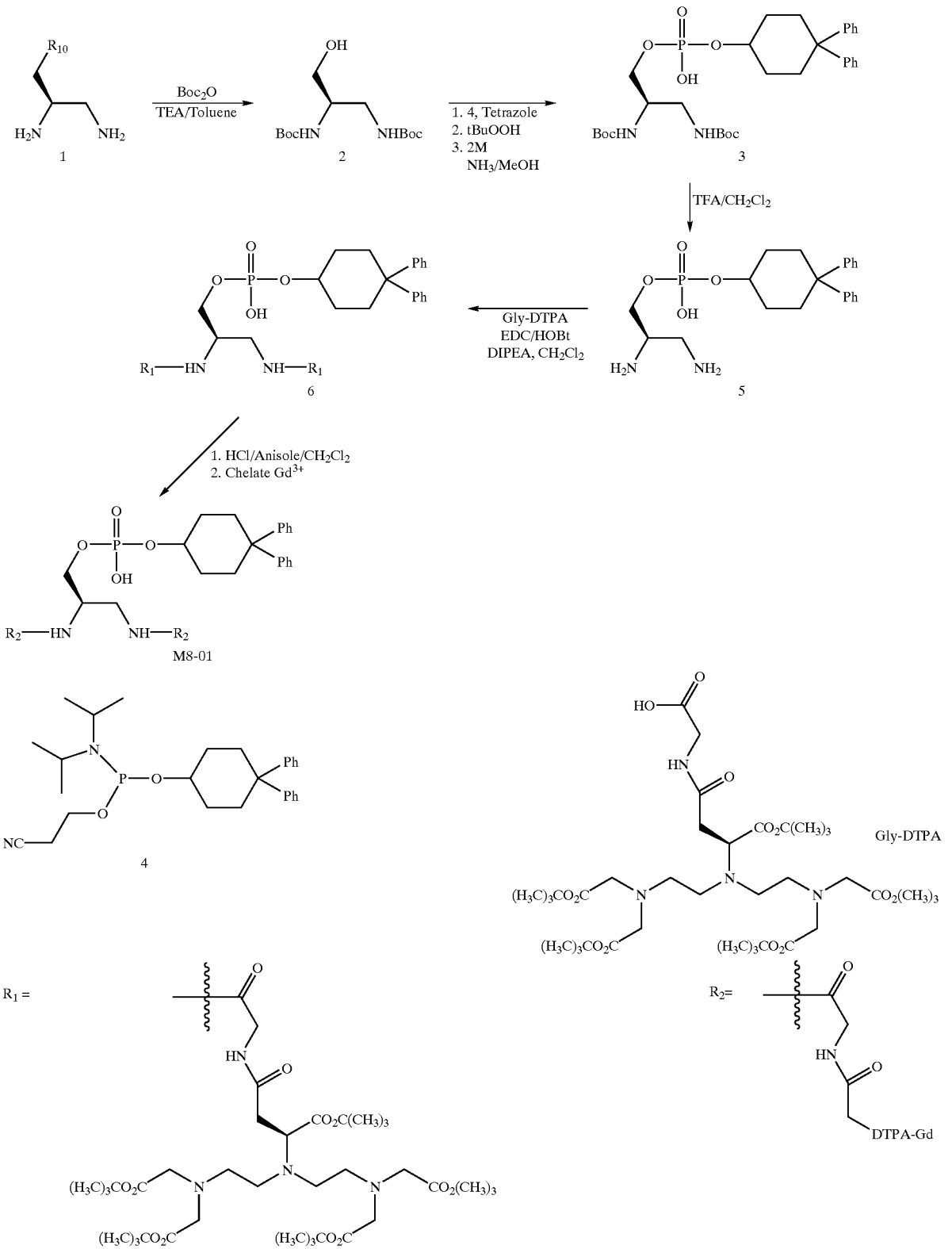
1,2-di(Boc-amino)-3-hydroxypropane (1.0 eq) and diphenylcyclohexyl phosphoramidite (1.1 eq) were dissolved in tetrahydrofuran (1.5 mL/mmol phosphoramidite) and stirred with molecular sieves for 30 min. To the mixture was added tetrazole (1.2 eq) at room temperature. The mixture was stirred for 45 min and $^{31}$p NMR indicated completion of the reaction. To the mixture was added tert-butylhydroperoxide (1.2 eq). The reaction mixture was stirred for about 1 h until $^{31}$P NMR indicated completion of the reaction. The resultant precipitate and molecular sieves were removed by filtration and then methylene chloride was added into the filtrate. The solution was washed sequentially with sodium thiosulfate solution, sodium bicarbonate solution and saturated sodium chloride, and dried over sodium sulfate, filtered and concentrated under vacuum. To the resulting pale yellow oil was added 2 M ammonia in methanol. The mixture was stirred overnight and then the solvent was removed under vacuum. The reaction mixture was purified by silica-gel column chromatography (ethylacetate/methanol eluant) to give the phosphodiester.

This phosphodiester was deprotected by stirring in trifluoroacetic acid and methylene chloride after which the mixture was lyophilized yielding the diamine-diphenylcyclohexyl-phosphodiester. This diamine was stirred overnight with 4 equivalents each of Gly-DTPA-O-tBu, EDC, and HOBt in methylene chloride to which diisopropylethylamine had been added to increase the pH. The concentrated reaction mixture was purified by preparative reverse-phase HPLC. The tert-butyl esters of the two DTPA units were cleaved by stirring in 4:1:1 hydrochloric acid:anisole:methylene chloride, and subsequently the DTPA-gadolinium chelate was formed with GdCl$_3$ in the usual way [see for example, Lauffer R. B., et al. *Radiology* 207: pp. 529–38 (1998)].

Example 10

Synthesis of M8-02

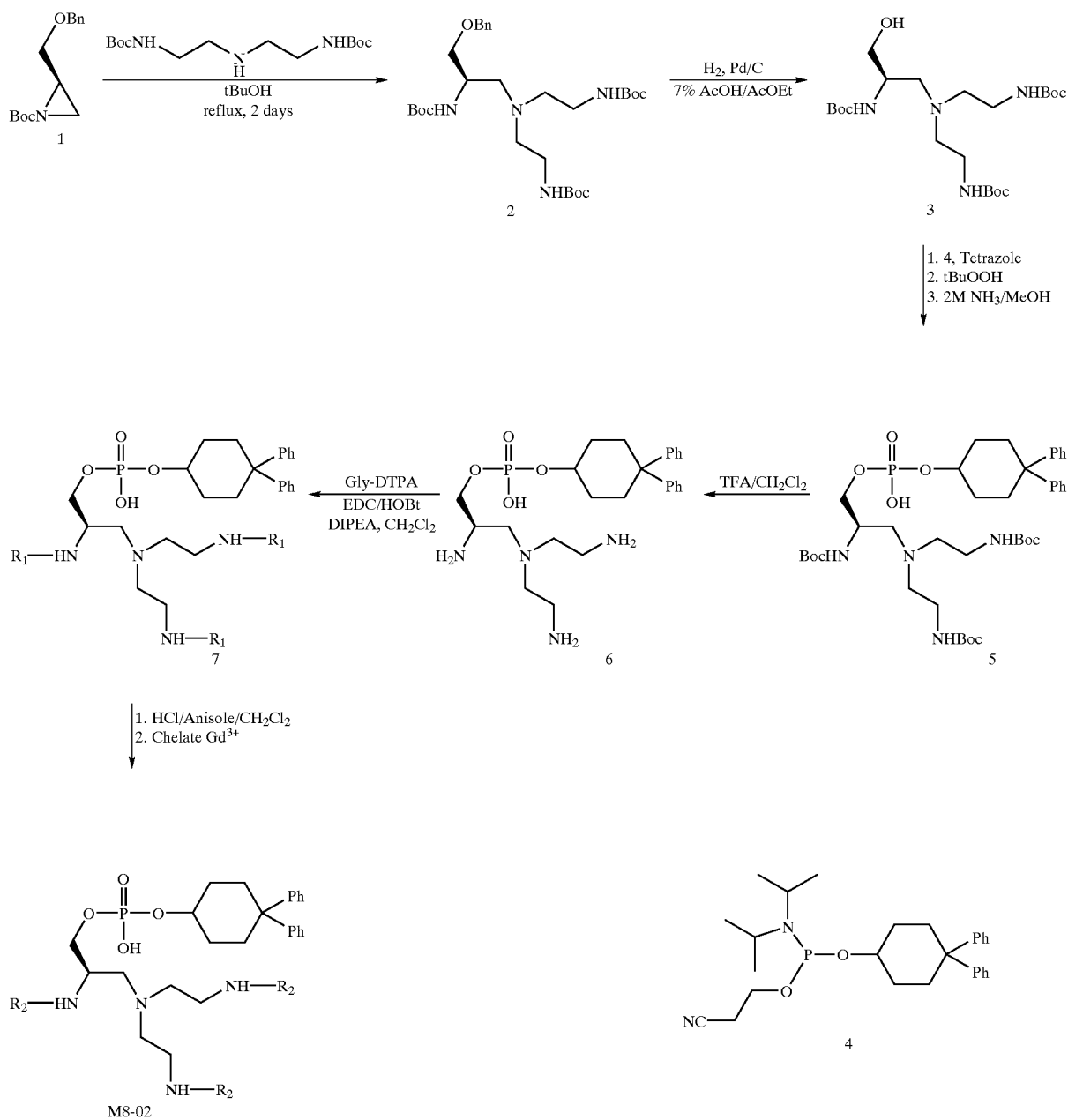

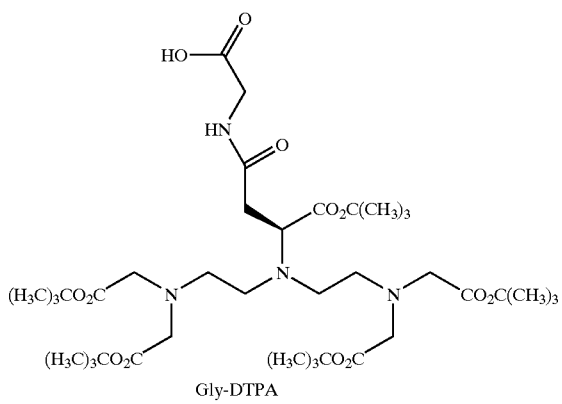

Gly-DTPA

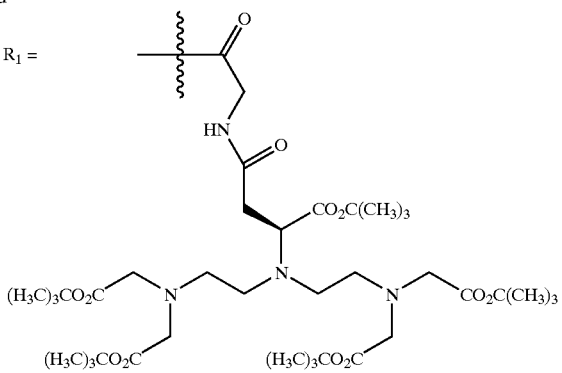

$R_1 =$

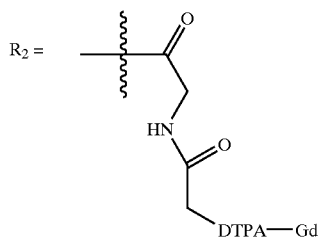

$R_2 =$

Benzyloxymethylene-N-Boc-aziridine (2.82 g), prepared from N-Boc-O-benzyl-serine, and N,N''-diBoc-diethylenetriamine (3.9 9) were stirred in refluxing tert-butanol for 2 d after which solvent was removed under vacuum, and the residue was purified by flash chromatography (methanol and methylene chloride eluant) yielding 4.54 g of material. The ratio of Boc hydrogens to aromatic hydrogens was verified by integration of the $^1$H NMR spectrum. This triBoc-protected tetraamine benzyl ether (3.8 g) was dissolved in 70 mL 7% acetic acid in ethyl acetate with 1.0 g 10% palladium on carbon. The reaction mixture was placed under an atmosphere of hydrogen at 48 psi for 16 h. Solvent was stripped from the reaction mixture under vacuum and the residue was purified by flash chromatography (methanol and methylene chloride eluant) to yield 3.6 g. The resulting alcohol and diphenylcyclohexyl phosphoramidite were reacted using the conditions stated above (tetrazole, tert-butylhydroperoxide, ammonia in methanol) to give the corresponding phosphodiester.

The three Boc groups of this phosphodiester (50 mg) were removed by stirring in 1.0 mL TFA and 1.0 mL DCM for 3 h after which the mixture was lyophilized yielding 54 mL of the triamine. This triamine was dissolved in 1.0 mL methylene chloride and was added dropwise to a solution containing 6 equivalents each of Gly-DTPA-O-tBu, EDC, and HOBt in 2.0 mL methylene chloride to which DIEA had been added to adjust the pH to 9.0. The concentrated reaction mixture was purified by preparative HPLC (C-4 column, 20 mL/min, 30:70 acetonitrile:water to 100:0 gradient over 25 min, then hold for 10 min). The molecular weight of the compound was verified by mass spectrometry. The tert-butyl esters of the DTPA subunits were cleaved to reveal the carboxylic acids by stirring in 4:1:1 hydrochloric acid:anisole:methylene chloride for 5 h after which the solution was stripped of solvent under vacuum, dissolved in water and lyophilized. The DTPA-gadolinium chelates were readily formed with GdCl$_3$ in the usual way [see for example, Lauffer R. B., et al. *Radiology* 207: pp. 529–38 (1998)].

Example 11

Synthesis of M8-03

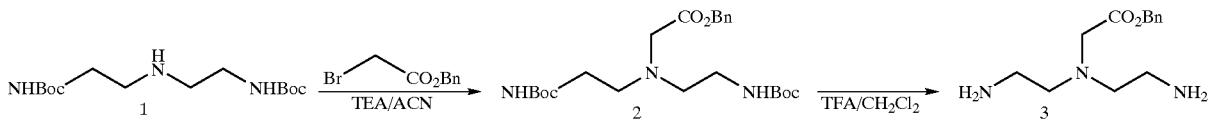

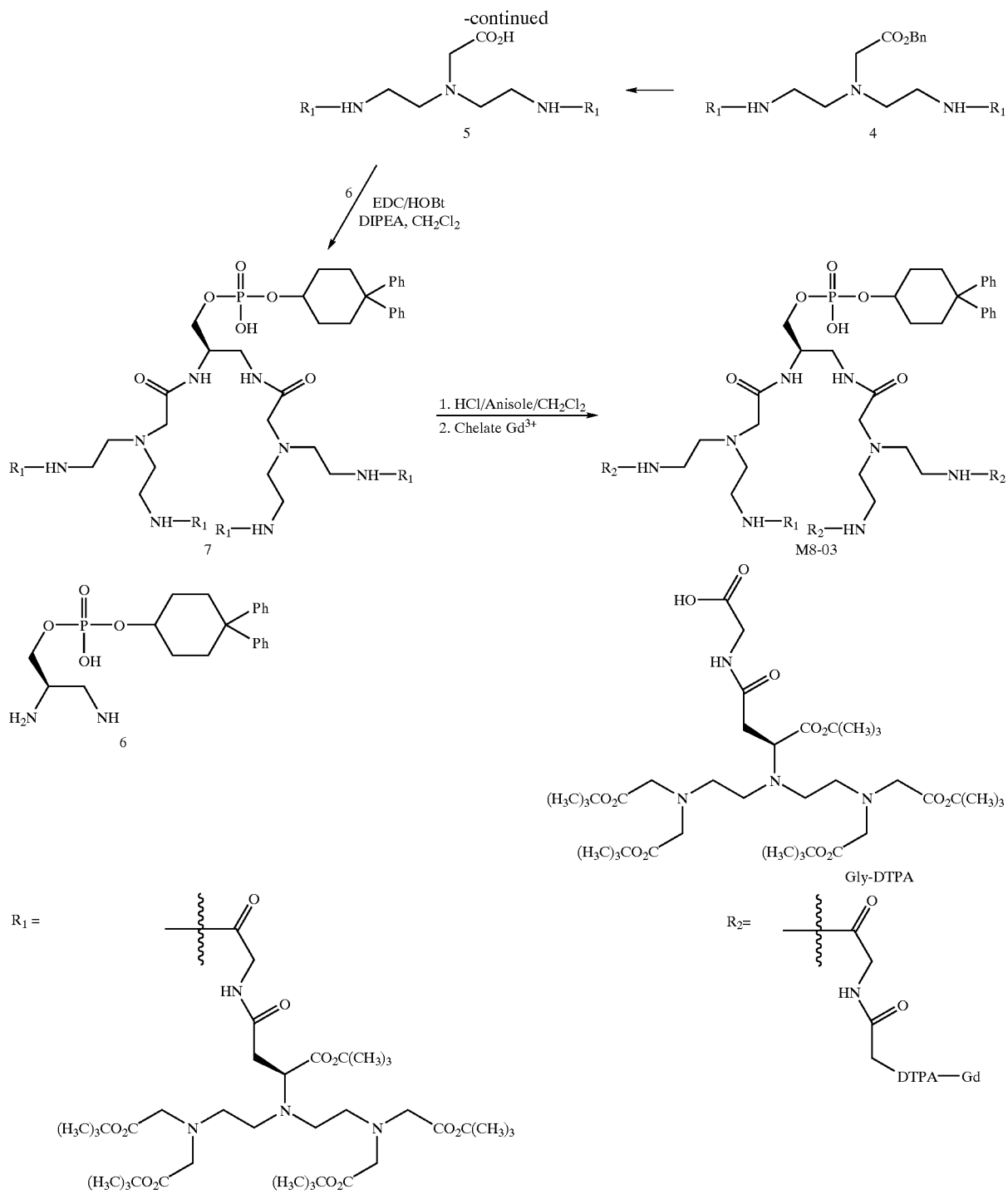

Benzylbromoacetate (11 mL) in 50 mL acetonitrile was added to N,N''-diBoc-diethylenetriamine (14 g) in 50 mL acetonitrile and 19 mL triethylamine and stirred for 2 h, after which solvent was removed under vacuum, and the residue was purified by flash chromatography (hexane/ethyl acetate eluant) to yield 11 g of material. The two Boc protecting groups of this compound were removed by stirring all of the material in a 1:1 mixture of trifluoroacetic acid and methylene chloride for 3 h, after which the solution was stripped of solvent under vacuum, partitioned between water and ether, and lyophilized to yield 9.2 g of material. Gly-DTPA-O-tBu, DIC, and HOBt (2.2 equivalents each) were stirred in N,N-dimethylformamide for 45 min and then this triamine (1.0 g), as the bis(ammonium trifluoroacetate), was dissolved in N,N-dimethylformamide and added to the reaction vessel, and the pH was adjusted to 9.0 by the addition of diisopropylethylamine.

After stirring for 12 hours, the solution was diluted with water and extracted with ethyl acetate which was sequentially washed with aqueous solutions of citric acid, saturated sodium bicarbonate, and saturates sodium chloride. The ethyl acetate solution was concentrated under vacuum and subject to flash chromatography (hexane/ethyl acetate eluant) to yield 845 mg of material confirmed to be the tetramer by mass spectrometry. The benzyl group was removed by hydrogenation of 800 mg of this material dissolved in 10 mL hexane, 9 mL methanol, and 1 mL triethylamine with 20% palladium on carbon under an atmosphere of hydrogen for 3 h after which the solution was filtered through Celite and concentrated under vacuum. This carboxylic acid (750 mg) was stirred in methylene chloride with EDC and HOBt (1.2 equivalents each) for 30 min and the diamine-diphenylcyclohexyl-phosphodiester, described above in the synthesis of M8-01, (80 mg) was dissolved in methylene chloride and added to the carboxylic acid solution and the pH was adjusted to 9.0 by the addition of diisopropylethyl amine. After several hours, the mixture was concentrated and purified by preparative HPLC (C-4 column, 20 mL/min, 30:70 acetonitrile:water to 100:0 gradient over 25 min, then hold for 10 min) to yield 150 mg of material, the molecular weight of which was verified by mass spectrometry. The tert-butyl esters of the DTPA subunits were cleaved to reveal the carboxylic acids by stirring in 4:1:1 hydrochloric acid:anisole:methylene chloride for 5 h after which the solution was stripped of solvent under vacuum, dissolved in water and lyophilized (yielding 90 mg). The DTPA-gadolinium chelates were readily formed with $GdCl_3$ in the usual way [see for example, Lauffer R. B., et al. *Radiology* 207: pp. 529–38 (1998)].

Example 12
Synthesis of M8-09

The mixture was stirred overnight. The solution was washed with water and extracted twice with a 0.1 N HCl solution, and the pH of the combined aqueous layer was raised to 8 and the aqueous layer was extracted 4 times with $CH_2Cl_2$. The combined organic layer was washed with saturated sodium chloride, dried over sodium sulfate, filtered and concentrated to give 1-benzylamino-2-indanol (15.62 g), the molecular weight of which was confirmed by mass spectrometry (m/e=239.95 for $M^+$). To a solution of 1-benzylamino-2-indanol (10.5 g) and triethylamine (9.2 mL) in methylene chloride (250 mL) was added dropwise 4-butylbenzoyl chloride (9.1 mL). The mixture was stirred 4 h and then concentrated under vacuum.

The residue was dissolved in ethyl acetate and was washed with water, dried over sodium sulfate, filtered, concentrated under vacuum, and purified by a flash chromatography (hexane/ethyl acetate eluant) to give 1-para-butylbenzoyl-1-benzylamino-2-indanol (12.7 g): $^1$H NMR ($CDCl_3$) δ0.93 (t, 3 H), 1.24–1.4 (m, 2 H), 1.5–1.65 (m, 2 H), 2.6 (t, 2 H), 2.8 (broad d, 1 H), 3.07 (dd, 1 H), 4.52 (m, 1 H), 4.65 (m, 2 H), 5.13 (m, 1 H), 7.09–7.32 (m, 11 H), 7.38–7.62 (m, 2 H). 1-para-Butylbenzoyl-1-benzylamino-2-indanol (1.26 g) and DTPA phosphoramidite (2.99 g) were dissolved in tetrahydrofuran (5 mL) and stirred with molecular sieves for 30 min, after which was added tetrazole (265 mg), and the mixture was stirred for 45 min.

$^{31}$P NMR indicated completion of the reaction, and to the mixture was added tert-butylhydroperoxide (0.433 mL), and the reaction mixture was stirred for 1 h until $^{31}$P NMR indicated completion of the reaction. The resultant precipi-

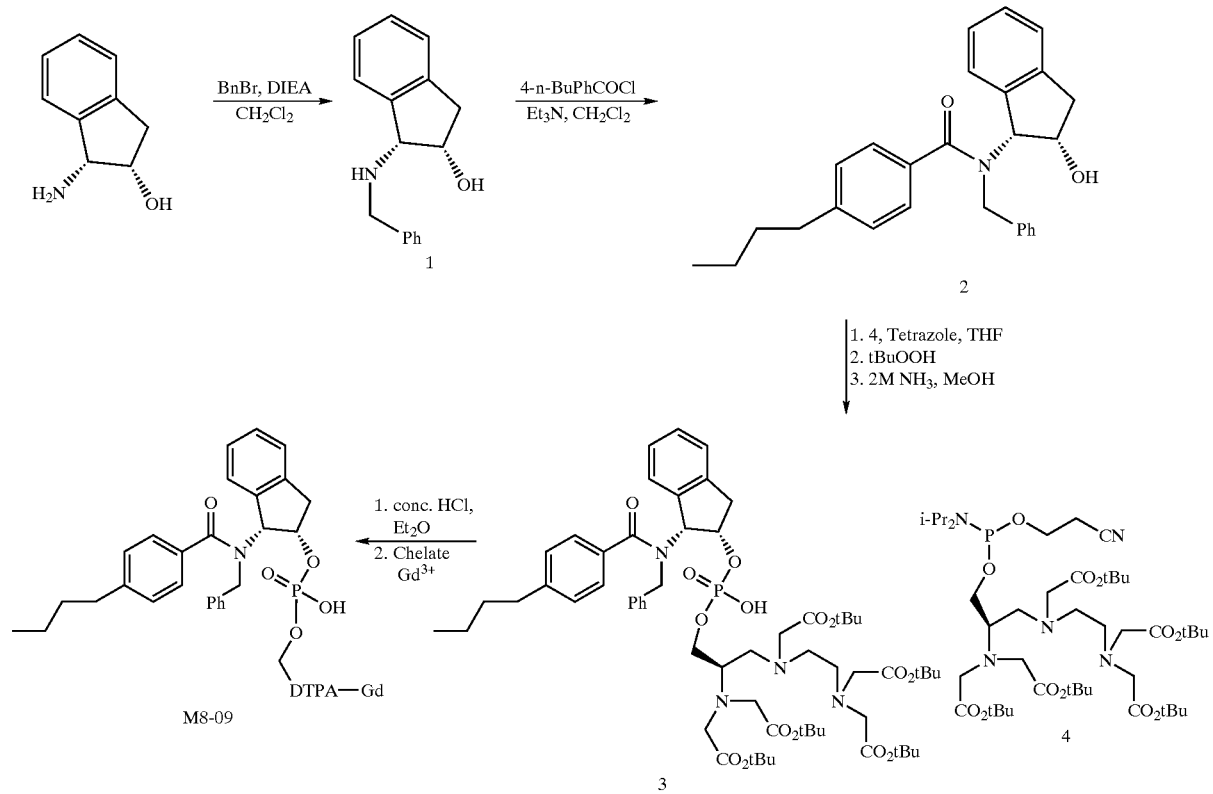

To a suspension of (1R-2S)-(+)-cis-1-Amino-2-indanol (15 g) in methylene chloride (90 mL) were added diisopropylethylamine (35 mL) and then benzylbromide (17.2 g).

tate and molecular sieves were removed by filtration and then methylene chloride was added into the filtrate. The solution was washed sequentially with sodium thiosulfate solution, sodium bicarbonate solution and saturated sodium chloride, and dried over sodium sulfate, filtered and concentrated under vacuum. To the resulting pale yellow oil was added 2M ammonia in methanol. The mixture was stirred overnight and then the solvent was removed at reduced pressure. The reaction mixture was purified by a flash chromatography (ethyl acetate/methanol eluant) to give the phosphodiester adduct as white solid $^{31}$P NMR (THF-d$^8$) δ –0.28; LC-MS (m/e) 1165.75 (M+H)$^+$.

The tert-butyl esters of the DTPA subunits were cleaved to reveal the carboxylic acids by dissolving in methylene chloride and treating with 12 N hydrochloric acid. After several hours, the pH was adjusted to 1.5 by addition of 5N sodium hydroxide aqueous solution, and the resulting white precipitate was filtered and was washed twice with hydrochloric acid solution (pH=1.5). The precipitate was lyophilized for 48 h to give the product as a fine white powder: LC-MS (m/e) 885.15 (M$^+$). The DTPA-gadolinium chelates were readily formed with GdCl$_3$ in the usual way [see for example, Lauffer R. B., et al. *Radiology* 207: pp. 529–38 (1998)].

Example 13

Synthesis of M8-10

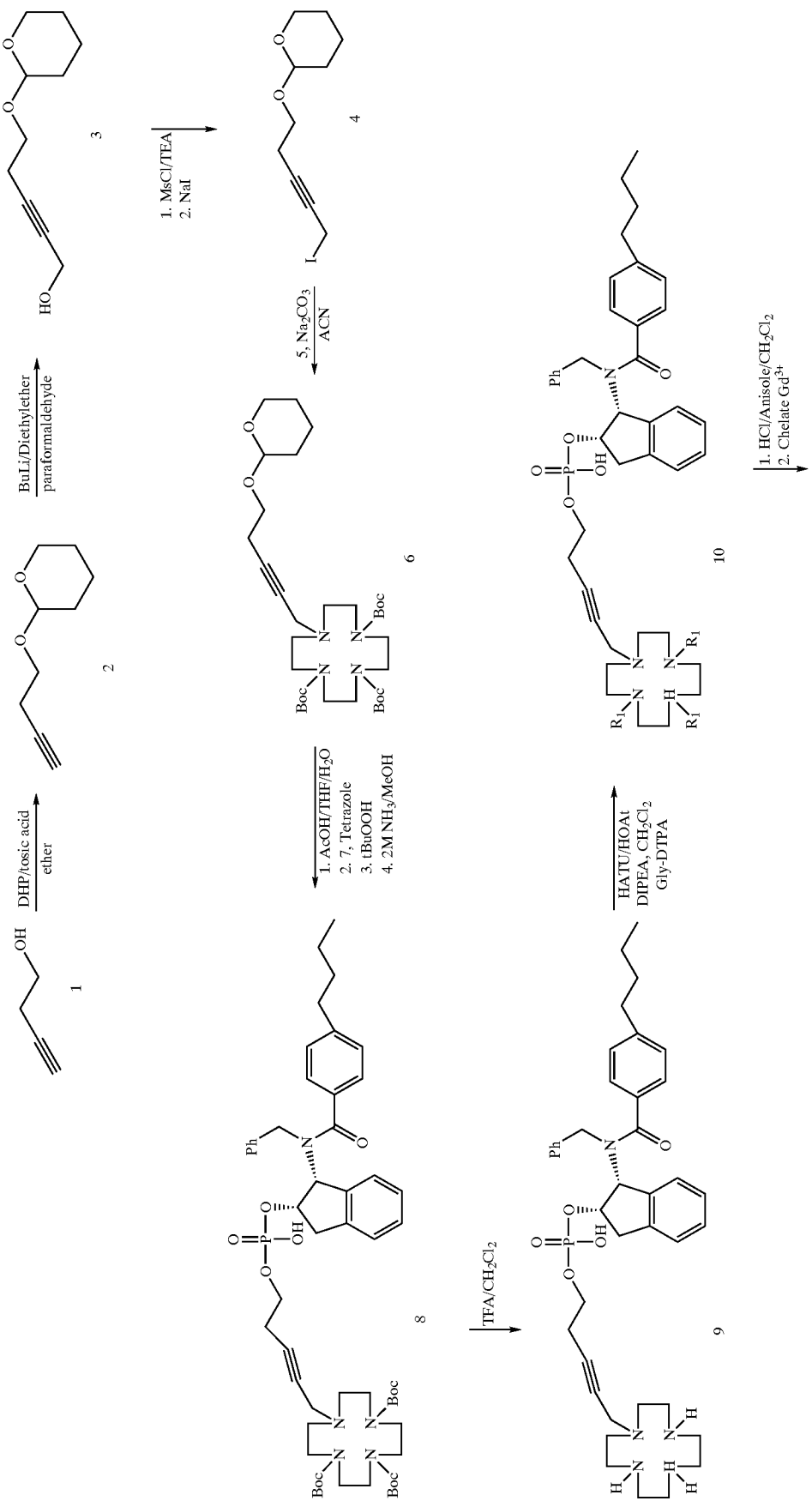

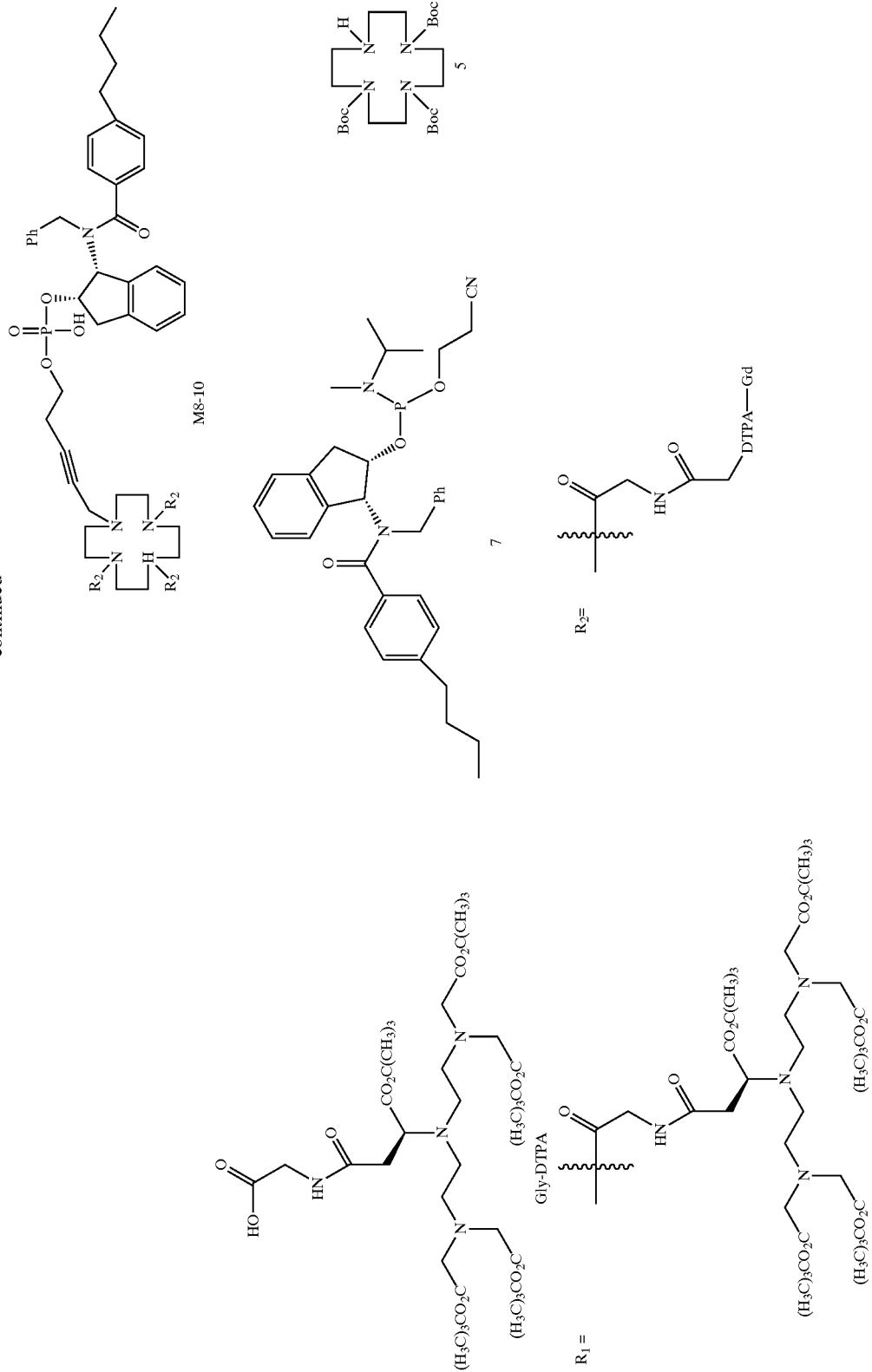

3-Butyne-1-ol (10 g) was stirred in ether (250 mL) with 3,4-dihydropyran (12 g) and tosic acid (20 mg) for 12 h, after which the solution was concentrated under vacuum and the residue was partitioned between ethyl acetate and water. The organic solution was washed with saturated aqueous sodium chloride, dried over sodium sulfate, and concentrated to a the DHP-protected alcohol (18.7 g) which was used without further characterization or purification. The DHP-alcohol (18.7 g) was dissolved in ether (65 mL) and cooled to −75° C. after which butyl lithium (50.5 mL of a 2.0 M solution) was added dropwise while maintaining the temperature after which paraformaldehyde (3.5 g) was added. After 4 h, the solution was allowed to warm to room temperature and water (100 mL) was added. The aqueous layer was discarded and the organic layer was concentrated under vacuum to an oil which was purified by flash chromatography (ethyl acetate/hexane eluant) to yield 5-THP-2-pentyn-1,5-ol (13 g) the structure of which was confirmed by $^1$H NMR.

The alkynol (2.0 g) was converted first to the mesylate (882 mg mesyl chloride, 1.6 mL triethylamine, methylene chloride) and then to the iodide (6.2 g sodium iodide, anhydrous acetone) by the conventional method. This iodoalkyne (1.2 g) was stirred with triBoc-cyclen (200 mg) and sodium carbonate (200 mg) in 8 mL acetonitrile for 1.5 h after which the mixture was stripped of solvent by concentration under vacuum and purified by flash chromatography (ethyl acetate/hexane eluant) and the identity of the adduct (240 mg) was verified by $^1$H NMR and LC-MS. The adduct (240 mg) was subsequently THP-deprotected by stirring in 4:2:1 acetic acid:tetrahydrofuran:water (12 mL) at 40° C. for 6 h after which the reaction was diluted with water and ethyl acetate and the organic layer was extracted sequentially with saturated aqueous sodium bicarbonate and sodium chloride, dried over sodium sulfate, and concentrated to the alcohol (250 mg). A phosphodiester of this alcohol and 1-para-butylbenzoyl-1-benzylamino-2-indanol was synthesized by the standard phosphoramidite chemistry described in the synthesis of M8-01 above (tetrazole, tert-butylhyrdoperoxide, ammonia/methanol).

The three Boc protecting groups on the cyclen were removed by treatment with acid (trifluoroacetic acid in methylene chloride), and the three resulting amines were converted to the amides with Gly-DTPA-O-tBu using standard methods (HATU/HOAt, diisopropylethyl amine, methylene chloride) as described above. The tert-butyl esters of the DTPA subunits were cleaved to reveal the carboxylic acids by stirring in 4:1:1 hydrochloric acid:anisole:methylene chloride for 5 h after which the solution was stripped of solvent under vacuum, dissolved in water and lyophilized. The DTPA-gadolinium chelates were readily formed with GdCl$_3$ in the usual way [see for example, Lauffer R. B., et al. *Radiology* 207: pp. 529–38 (1998)].

Example 14

Synthesis of M8-06

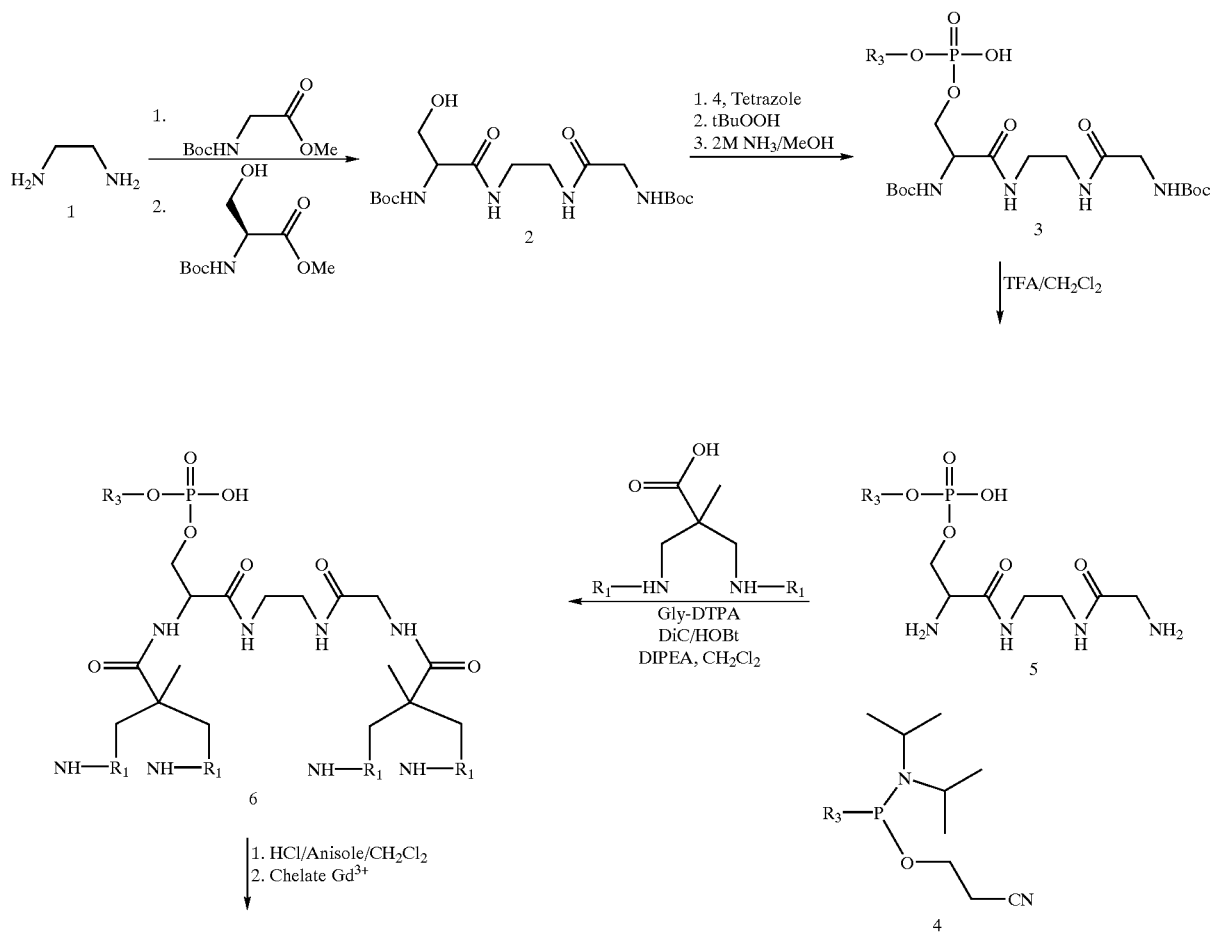

-continued

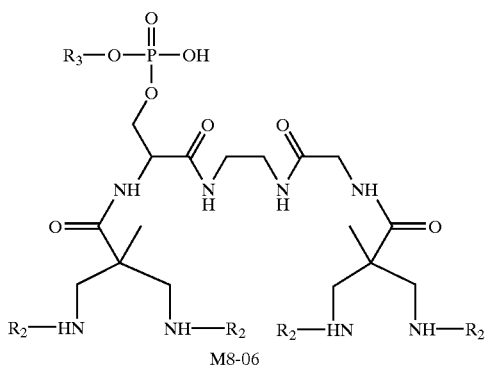
M8-06

$R_3 =$ 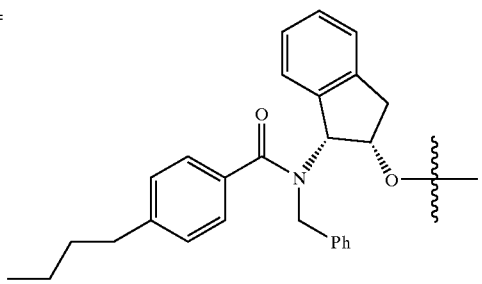

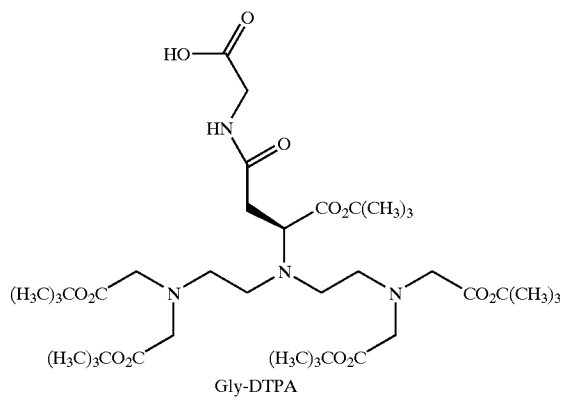
Gly-DTPA $R_1 =$ 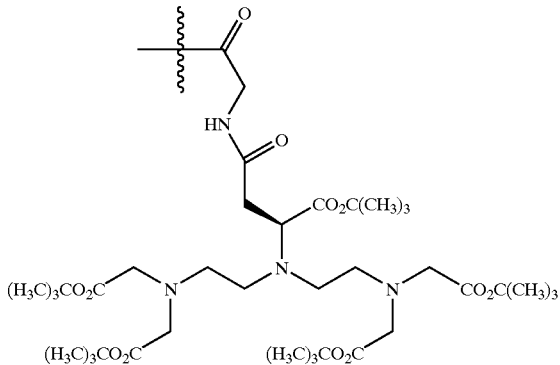

$R_2 =$ 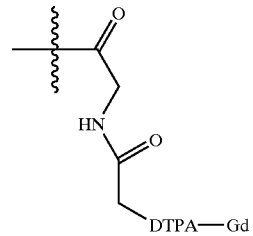

Ethylene diamine was reacted sequentially with N-Boc-glycine methyl ester and N-Boc-serine methyl ester to form the diamide. The free alcohol and 1-para-butylbenzoyl-1-benzylamino-2-indanol were converted to the phosphodiester by the method (tetrazole, tert-butylhydroperoxide, ammonia/methanol) discussed above. Benzyl-(3-amino-2-aminomethyl-2-methyl)propanoate and two equivalents of Gly-DTPA-O-tBu were reacted using the conditions described above (DIC/HOBt, diisopropylethylamine, methylene chloride) to form the corresponding diamide. Two equivalents of this diamide were reacted with the ethylene diamine derivative to form a tetramer. The tert-butyl esters of the DTPA subunits were cleaved to reveal the carboxylic acids by stirring in 4:1:1 hydrochloric acid:anisole:methylene chloride for 5 h after which the solution was stripped of solvent under vacuum, dissolved in water and lyophilized. The DTPA-gadolinium chelates were readily formed with $GdCl_3$ in the usual way [see for example, Lauffer R. B., et al. *Radiology* 207: pp. 529–38 (1998)].

Example 15
Synthesis of M8-04
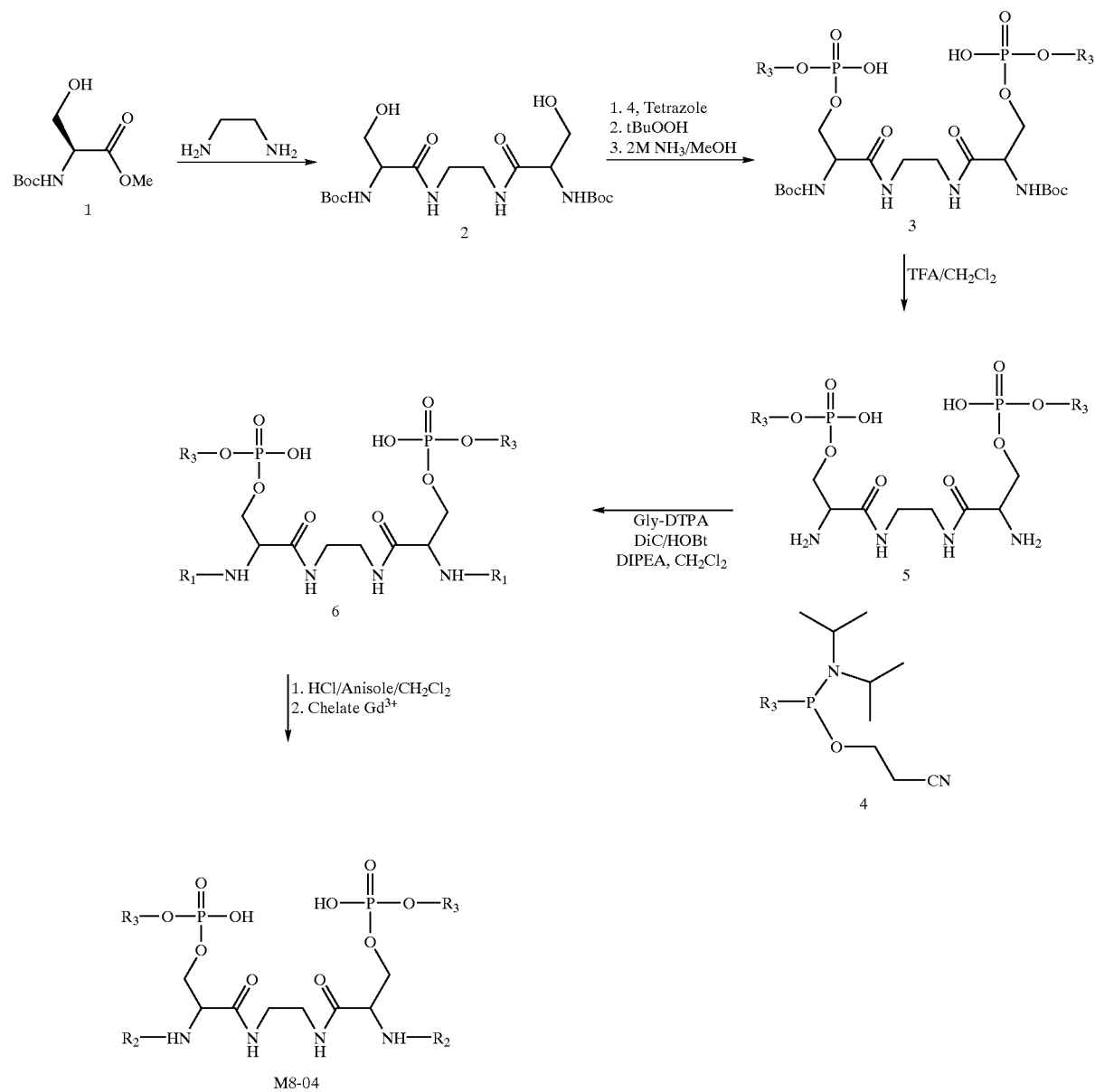
R₃ =
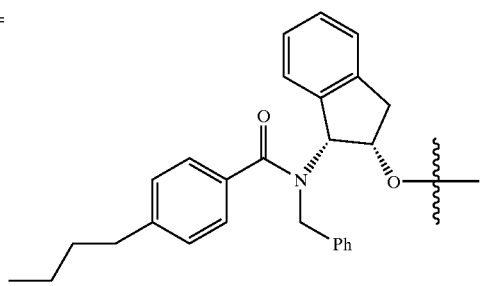
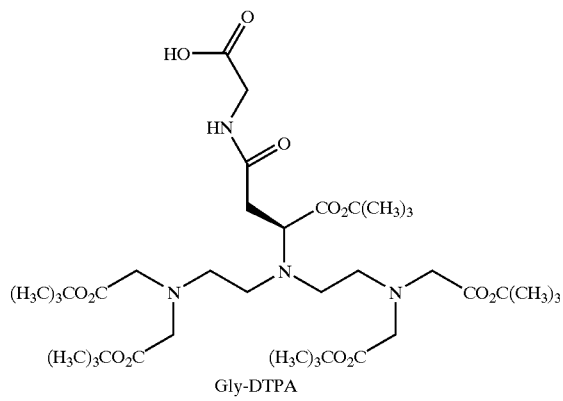
Gly-DTPA

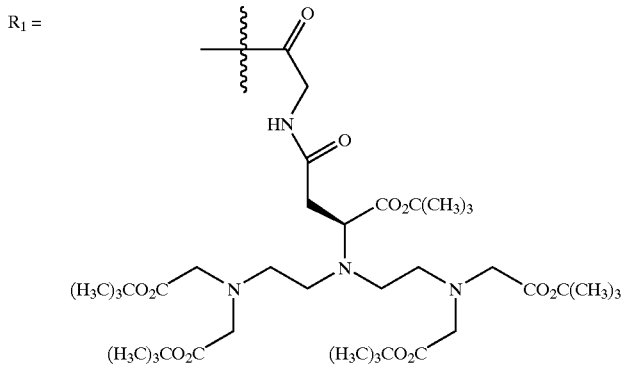
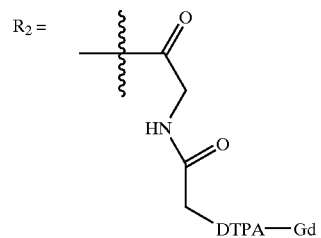
Ethylene diamine and 2 equivalents of N-Boc-serine methyl ester were reacted to form the diamide. The diamide was further reacted to form the diphosphate derivative as depicted above. The TBMs were attached and deprotected according to the synthetic scheme shown and using the methods discussed above in Example 14.
Example 16
Synthesis of M8-05
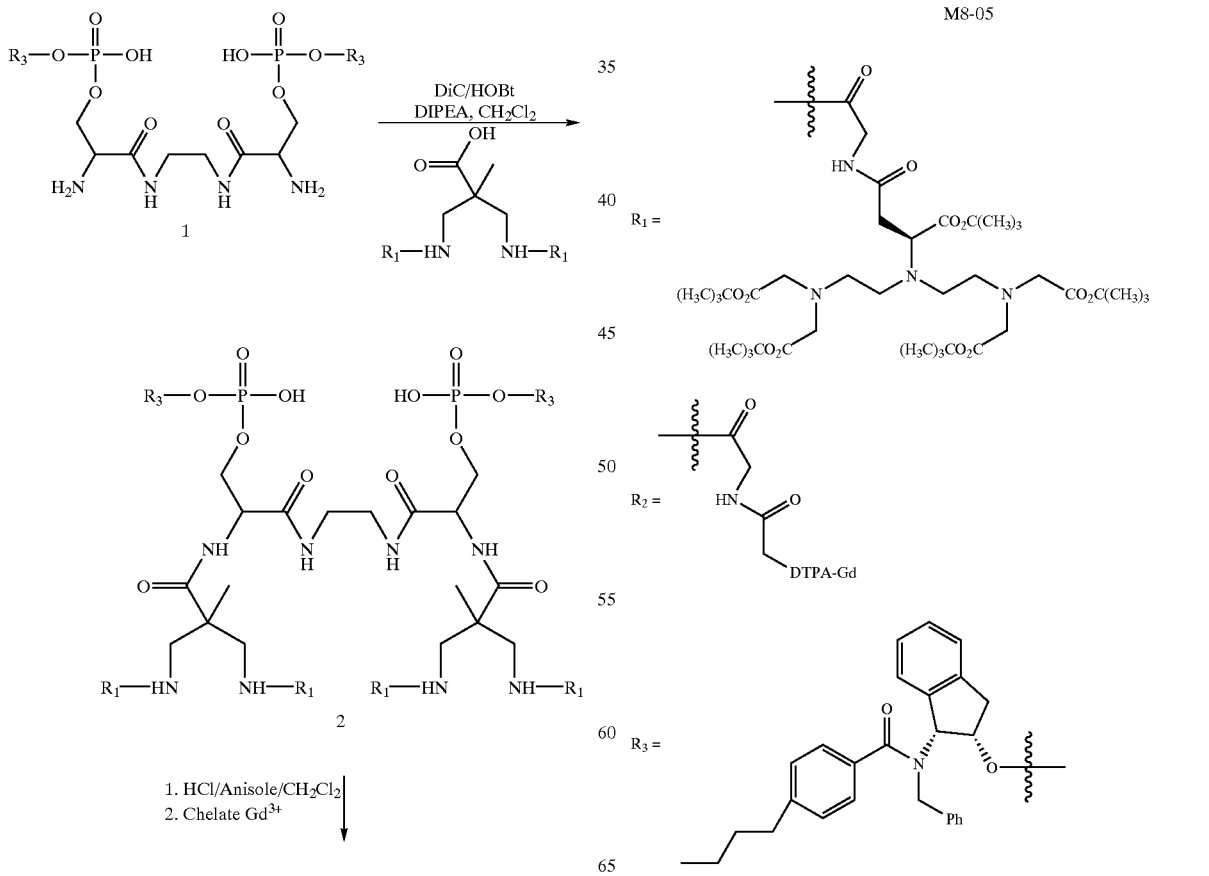

The diphosphate derivative of the diamide used as the starting material in this synthesis is identical to an intermediate in the synthesis of M8–04 shown in Example 15. The TBMs were attached and deprotected according to the synthetic scheme shown and using the methods discussed above in Example 14.

Example 17
Binding of M8-11 as measured by the Rabbit Jugular Model

Figure 14:
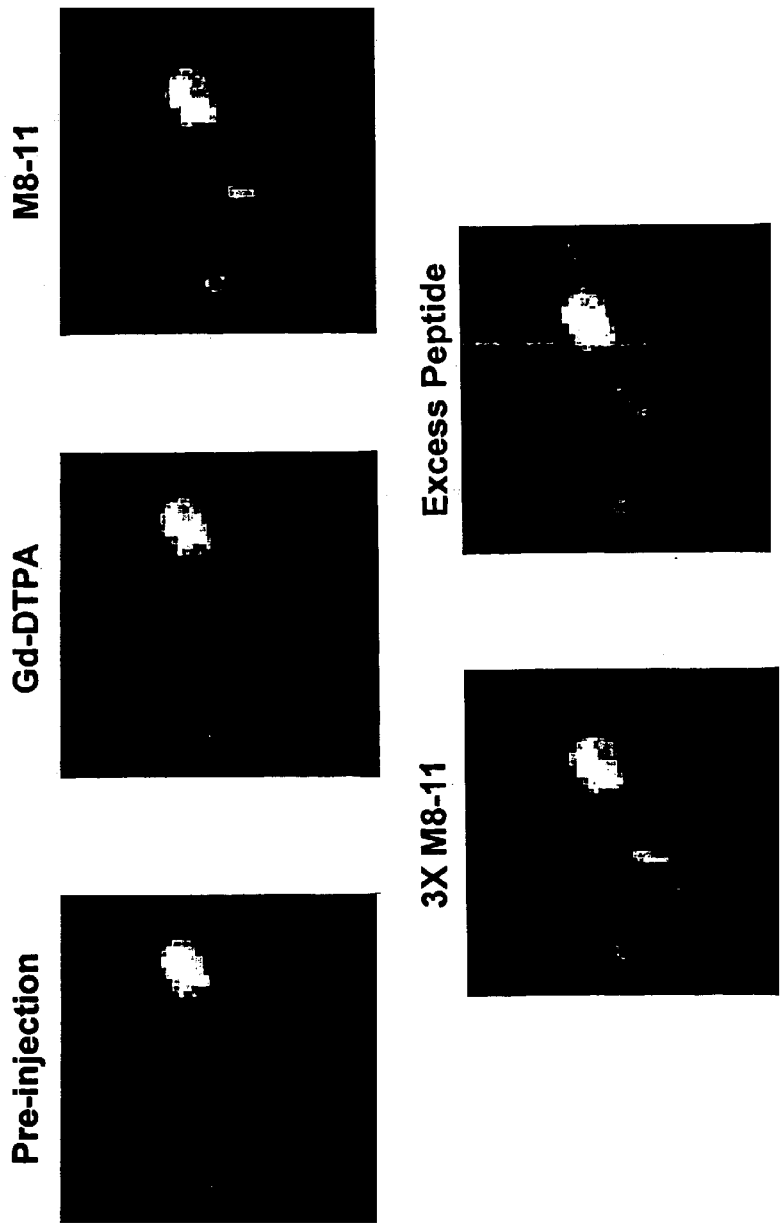
FIG. 14. Dynamic Imaging of Specific Fibrin Targeting

FIG. 14 is a reproduction of a color photograph of the images obtained in an experiment using the assay given in Example 1. The experiment shows the images at preinjection, injection with a control untargeted Gd-DTPA compound, injection with M8-11 given in Example 3, injection with three times the dose of M8-11, and injection with excess peptide (in single letter amino acid format) of sequence LPCDYYGTCLD, which competes for the target with the TBM of the contrast agent. The clot is specifically imaged by M8-11, since a contrast agent lacking the TBM does not bind and since the binding is reversed in the presence of excess peptide.

Example 18
Near Infrared Optical Imaging Agent

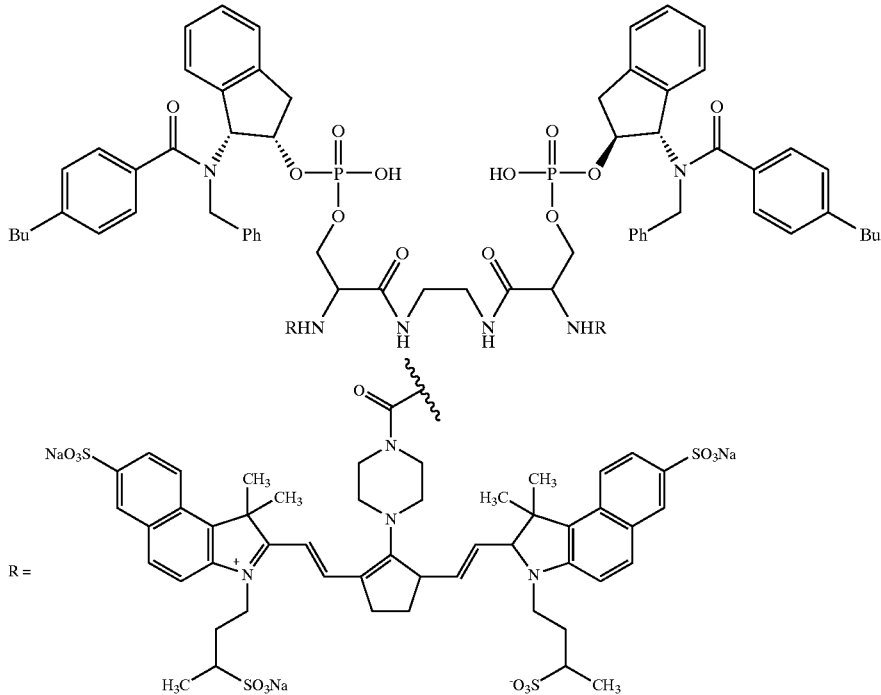

M8-24

The near infrared fluorescent imaging agent M8-24 contains an IEM suitable for optical imaging ("R"). The agent is prepared from the corresponding carboxylic acid derivative of the fluorescent dye (as disclosed in WO 2000/16810). The carboxylic acid derivative is attached to the diphosphate derivative of the diamide according to the conditions for the synthetic step shown in Example 13. In Example 13, the analogous step is the attachment of the Gly-DTPA TBM to the diphosphate derivative of the diamide to form M8-04. This albumin-targeted infrared contrast agent is used, for example, in ophthalmologic angiography and in the diagnosis of cancers of the skin. The optical contrast agent shown above may be used for any of the uses listed for MRI blood pool agents. Furthermore, one of skill will appreciate that the IEMs of such an optical imaging agent may be varied by substituting a different carboxylic acid derivative of a dye. The agent may therefore be tailored to conform to specific experimental criteria, such as a particular excitation wavelength.

We claim:

1. A method for MR imaging of a protein target in an animal or human subject, said method comprising the steps of:

a) administering an MRI contrast agent to said animal or human subject, wherein said MRI contrast agent is capable of binding to said protein target, and wherein the relaxivity of said MRI contrast agent increases upon binding to said protein target, said MRI contrast agent having the structure:

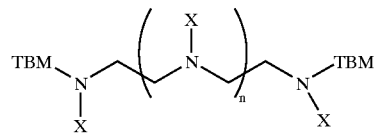

wherein:
TBM indicates a Target Binding Moiety having affinity for said protein target;
n is an integer from 0 to 8 inclusive;

X is independently selected from the group consisting of H, IEM, L-IEM, and L-(IEM)$_2$, provided that at least two of X are independently IEM, L-IEM, or L-(IEM)$_2$; and wherein each of said IEMs independently comprises a complex between:
(1) a chelating agent selected from the group consisting of DTPA, DOTA, and DOTMA, and
(2) one or more paramagnetic metal ions selected from the group consisting of Gd(III), Fe(III), Mn(II), Mn(III), Cr(III), Cu(II), Dy(III), Tb(III), Tb(IV), Ho(III), Er(III), Pr(III), Eu(II), and Eu(III);

b) allowing said MRI contrast agent to bind to said protein target; and c) imaging a region of said subject's body in which said protein target is located.

2. The method according to claim 1, wherein said target protein is selected from the group consisting of alpha-acid glycoprotein, HSA, fibrin, fibrinogen, and collagen.

3. The method according to claim 2, wherein said target protein is HSA or fibrin.

4. The method according to claim 1, wherein said chelating agent is selected from the group consisting of:

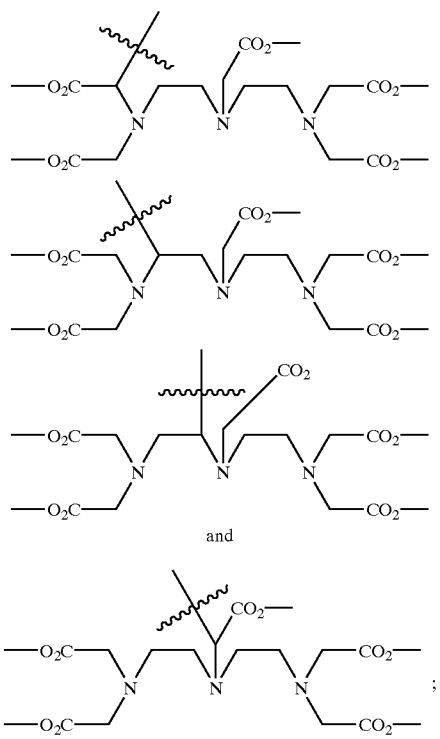

wherein said paramagnetic metal ion is Gd(III); and wherein the wavy symbol indicates the attachment of the chelating agent to the remainder of the MRI contrast agent.

5. The method according to claim 1, wherein said linker L has a molecular weight of less than 200 and comprises two or more functional chemical groups.

6. The method according to claim 1, wherein said linker L is selected from the group consisting of:

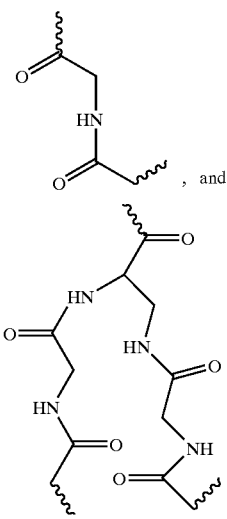

wherein the wavy symbol indicates the attachment of the linker to the remainder of the MRI contrast agent.

7. The method according to claim 2, wherein said protein target is HSA and wherein at least one of said TBMs comprises one or more chemical moieties selected from the group consisting of aryl rings, cyclohexyl rings, benzofused cyclopentyl groups, and linear and branched alkyl chains of 1 to 4 carbon atoms, wherein said moieties are optionally substituted with one or more halogen atoms.

8. The method according to claim 5, wherein said TBMs are selected from the group consisting of:

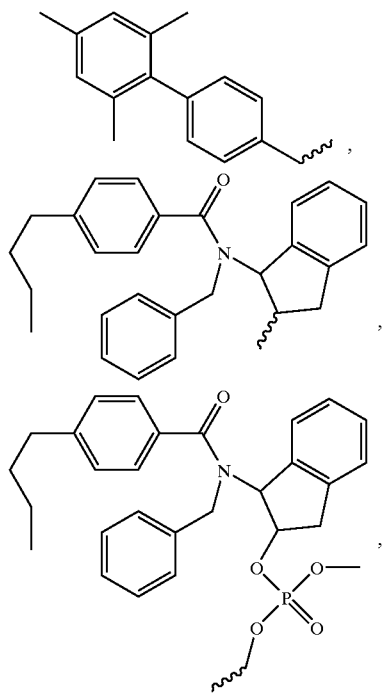

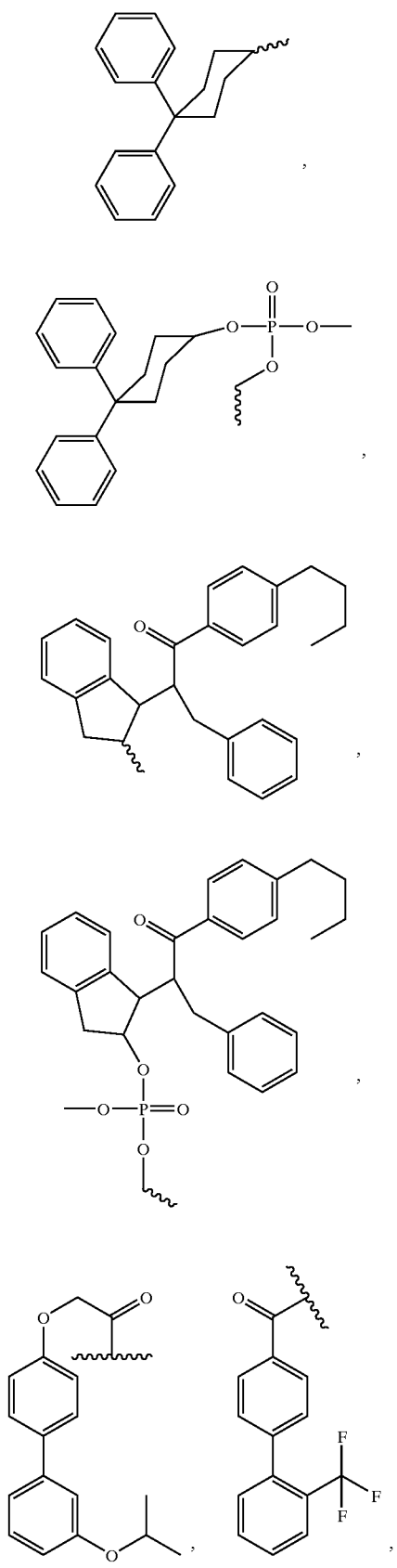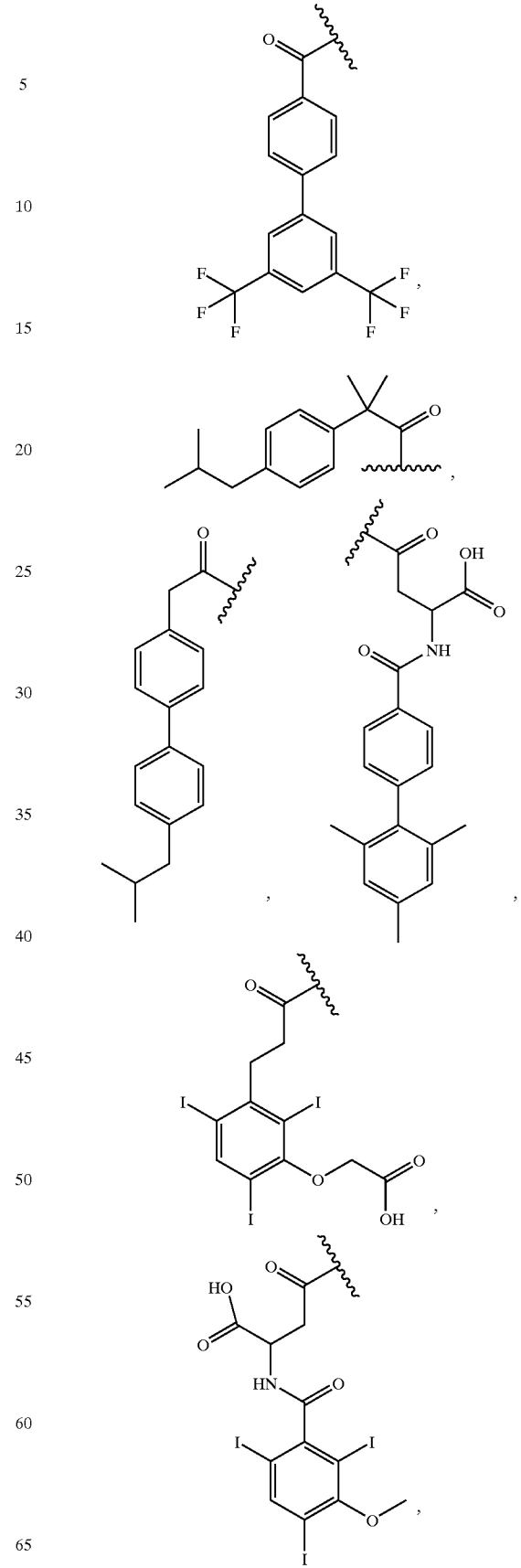

and

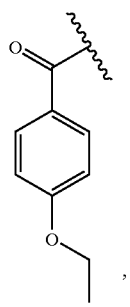

wherein the wavy symbol indicates the attachment of the TBM to the remainder of the MRI contrast agent.

9. The method according to claim 2, wherein said target is fibrin and wherein at least one of said TBMs is a peptide having an affinity for fibrin.

10. The method according to claim 9, wherein said peptide is cyclic.

11. The method according to claim 1, wherein n=0.

12. The method according to claim 1, wherein n=2.

13. The method according to claim 1, wherein n=4.

14. The method according to claim 1, wherein said MRI contrast agent has a structure selected from the group consisting of:

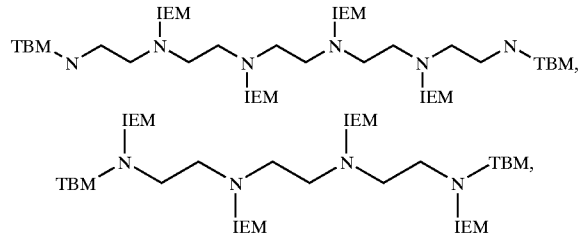

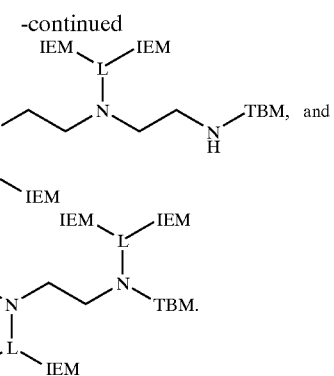

15. The method according to claim 1, wherein said MRI contrast agent has the structure:

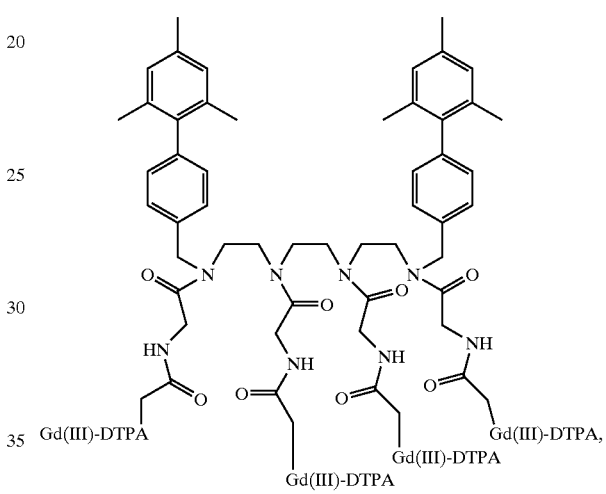

wherein Gd(III)-DTPA is a complex between the chelating agent DTPA and the paramagnetic metal ion Gd(III).

* * * * *

UNITED STATES PATENT AND TRADEMARK OFFICE
CERTIFICATE OF CORRECTION

PATENT NO. : 6,652,835 B1
DATED : November 25, 2003
INVENTOR(S) : Randall B. Lauffer et al.

It is certified that error appears in the above-identified patent and that said Letters Patent is hereby corrected as shown below:

<u>Title page,</u>
Item [75], Inventors, please add -- Shrikumar Nair --

Signed and Sealed this

Fourth Day of May, 2004

JON W. DUDAS
*Acting Director of the United States Patent and Trademark Office*